US011873317B2

(12) United States Patent
Magnani et al.

(10) Patent No.: US 11,873,317 B2
(45) Date of Patent: Jan. 16, 2024

(54) GALECTIN-3 INHIBITING C-GLYCOSIDES

(71) Applicant: GLYCOMIMETICS, INC., Rockville, MD (US)

(72) Inventors: John L. Magnani, Gaithersburg, MD (US); John M. Peterson, Slate Hill, NY (US); Arun K. Sarkar, North Potomac, MD (US); Yusufbhai U. Vohra, Germantown, MD (US); Indranath Ghosh, Olney, MD (US); Jason Nogueira, Germantown, MD (US)

(73) Assignee: GLYCOMIMETICS, INC., Rockville, MD (US)

( * ) Notice: Subject to any disclaimer, the term of this patent is extended or adjusted under 35 U.S.C. 154(b) by 245 days.

(21) Appl. No.: 17/418,590

(22) PCT Filed: Dec. 26, 2019

(86) PCT No.: PCT/US2019/068597
§ 371 (c)(1),
(2) Date: Jun. 25, 2021

(87) PCT Pub. No.: WO2020/139960
PCT Pub. Date: Jul. 2, 2020

(65) Prior Publication Data
US 2022/0073555 A1 Mar. 10, 2022

Related U.S. Application Data

(60) Provisional application No. 62/927,192, filed on Oct. 29, 2019, provisional application No. 62/785,588, filed on Dec. 27, 2018.

(51) Int. Cl.
C07H 19/056 (2006.01)
C07H 19/06 (2006.01)
C07H 19/24 (2006.01)
A61K 31/7056 (2006.01)

(52) U.S. Cl.
CPC ....... *C07H 19/056* (2013.01); *A61K 31/7056* (2013.01); *C07H 19/06* (2013.01); *C07H 19/24* (2013.01)

(58) Field of Classification Search
None
See application file for complete search history.

(56) References Cited

U.S. PATENT DOCUMENTS

| 5,474,986 | A | 12/1995 | Magnusson et al. |
| 7,230,096 | B2 | 6/2007 | Nilsson et al. |
| 7,638,623 | B2 | 12/2009 | Nilsson et al. |
| 7,700,763 | B2 | 4/2010 | Leffler et al. |
| 7,772,192 | B2 | 8/2010 | Esko |
| 7,781,411 | B2 | 8/2010 | Hueter et al. |
| 8,697,862 | B2 | 4/2014 | Nilsson |
| 8,703,720 | B2 | 4/2014 | Leffler et al. |
| 9,243,021 | B2 | 1/2016 | Sethi et al. |
| 9,580,456 | B2 | 2/2017 | Nilsson et al. |
| 9,624,255 | B2 | 4/2017 | Hecht et al. |
| 2007/0037775 | A1 | 2/2007 | Magnani et al. |
| 2009/0176717 | A1 | 7/2009 | Magnani |
| 2009/0214439 | A1 | 8/2009 | Kumar et al. |
| 2010/0022620 | A1 | 1/2010 | Crispin et al. |
| 2014/0011765 | A1 | 1/2014 | Nilsson |
| 2015/0320782 | A1 | 11/2015 | Panjwani et al. |
| 2016/0096861 | A1 | 4/2016 | Sethi et al. |
| 2017/0095496 | A1 | 4/2017 | Deierborg et al. |

FOREIGN PATENT DOCUMENTS

| DE | 19643764 | | 4/1998 |
| EP | 0943623 | A1 | 9/1999 |
| EP | 1751172 | B1 | 7/2014 |
| EP | 2297174 | B1 | 7/2015 |
| EP | 2807176 | B1 | 12/2015 |
| EP | 2679595 | B1 | 12/2016 |
| GB | 2511137 | | 8/2014 |
| WO | WO 92/16640 | | 10/1992 |
| WO | WO 94/00596 | | 1/1994 |
| WO | WO 95/00527 | | 1/1995 |
| WO | WO 98/28315 | | 7/1998 |
| WO | WO 99/43337 | | 9/1999 |
| WO | WO 00/035945 | | 6/2000 |
| WO | WO 02/057284 | | 7/2002 |
| WO | WO 03/066647 | | 8/2003 |
| WO | WO 03/093286 | | 11/2003 |
| WO | WO 05/000860 | | 1/2005 |
| WO | WO 05/061523 | | 7/2005 |
| WO | WO 05/113569 | | 12/2005 |

(Continued)

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596 (Year: 1996).*
Dahlquist et al., "3-Substituted 1-Naphthamidomethyl-C-Galacyosyls Interact with Two Unique Sub-Sites for High-Affinity and High-Selectivity Inhibition of Galectin-3," Molecules, vol. 24, No. 24, Dec. 12, 2019, p. 4554.

(Continued)

*Primary Examiner* — Traviss C McIntosh, III

(74) *Attorney, Agent, or Firm* — FINNEGAN, HENDERSON, FARABOW, GARRETT & DUNNER LLP

(57) ABSTRACT

Compounds, compositions, and methods for treatment and/or prevention of at least one disease, disorder, and/or condition by inhibiting binding of galectin-3 to ligands are disclosed. For example, inhibitors of galectin-3 are described and pharmaceutical compositions comprising at least one such agent is described.

61 Claims, 7 Drawing Sheets

(56) References Cited

FOREIGN PATENT DOCUMENTS

| WO | WO 08/012555 | 1/2008 | |
|---|---|---|---|
| WO | WO 08/104486 | 9/2008 | |
| WO | WO 09/001097 | 12/2008 | |
| WO | WO 09/126737 | 10/2009 | |
| WO | WO 09/139719 | 11/2009 | |
| WO | WO 10/040710 | 4/2010 | |
| WO | WO 11/002673 | 1/2011 | |
| WO | WO 11/019419 | 2/2011 | |
| WO | WO 11/129314 | 10/2011 | |
| WO | WO 13/170985 | 11/2013 | |
| WO | WO 13/182206 | 12/2013 | |
| WO | WO 14/027203 | 2/2014 | |
| WO | WO 14/065661 | 5/2014 | |
| WO | WO 14/067986 | 5/2014 | |
| WO | WO 14/078655 | 5/2014 | |
| WO | WO 14/153009 | 9/2014 | |
| WO | WO 14/177771 | 11/2014 | |
| WO | WO 15/173373 | 11/2015 | |
| WO | WO 15/197082 | 12/2015 | |
| WO | WO 16/005311 | 1/2016 | |
| WO | WO 16/044846 | 3/2016 | |
| WO | WO 16/113335 | 7/2016 | |
| WO | WO 16/120403 | 8/2016 | |
| WO | WO 16/180483 | 11/2016 | |
| WO | WO 17/019770 | 2/2017 | |
| WO | WO 17/080973 | 5/2017 | |
| WO | WO 18/011094 | 1/2018 | |
| WO | WO-2018011094 A1 * | 1/2018 | ......... A61K 31/7056 |
| WO | WO 18/209276 | 11/2018 | |
| WO | WO 19/067702 | 4/2019 | |
| WO | WO 19/075045 | 4/2019 | |
| WO | WO 19/133878 | 7/2019 | |
| WO | WO 20/139960 | 7/2020 | |
| WO | WO 20/139962 | 7/2020 | |
| WO | WO 20/219417 | 10/2020 | |
| WO | WO 21/086816 | 5/2021 | |

OTHER PUBLICATIONS

Kumar et al., "Structure and Energetics of Ligand-Fluorine Interactions with Galectin-3 Backbone and Side-Chain Amides: Insight into Solvation Effects and Multipolar Interactions," ChemMedChem, vol. 14, No. 16, Jul. 11, 2019, pp. 1528-1536.
Peterson et al., "Systematic Tuning of Fluoro-galectin-3 Interactions Provides Thiodiagalactoside Derivatives with Single-Digit nM Affinity and High Selectivity," Journal of Medicinal Chemistry, vol. 61, No. 3, Jan. 11, 2018, pp. 1164-1175.
"Abbott's Galectin-3 Test Provides Doctors in Europe with New Tool for Assessing the Prognosis of Chronic Heart Failure Patients," Apr. 10, 2013.
Astorgues-Xerri et al., "Unraveling galectin-1 as a novel therapeutic target for cancer," Cancer Treatment Reviews, 40(2014), 307-319.
Atmanene et al., "Biophysical and structural characterization of mono/di-arylated lactosamine derivatives interaction with human galectin-3," Biochemical and Biophysical Research Communications xxx (2017), 1-6.
Barondes et al., "Galectins," The Journal of Biological Chemistry, vol. 269, No. 33, Issue of Aug. 19, p. 20807-20810, 1994.
Barton et al., "Tandem Nucleophilic and Radical Chemistry in the Rplacement of the Hydroxyl Group by a Carbon-Carbon Bond. A Concise Synthesis of Showdomycin," J. Am. Chem. Soc., 1990, 112, 891-892.
Besler et al., "Plasma and Cardiac Galectin-3 in Patients With Heart Failure Reflects Both Inflammation and Fibrosis—Implications for Its Use as a Biomarker." Downloaded on Sep. 12, 2017.
Blanchard et al., Galectin-3 inhibitors: a patent review (2008-present), Expert Opin. Ther. Patents, (2014), 24(10), pp. 1-13.
Blidner et al., "'Sweetening' Pregnancy: Galectins at the Fetomaternal Interface," Am. J Reprod Immunol, 2013; 69:369-382.

Bum-Erdene et al., "Investigation into the Feasibility of Thioditaloside as a Novel Scaffold for Galectin-3-Specific Inhibitors," ChemBioChem, 2013, 14, 1331-1342.
Cagnoni et al., "Design and Synthesis of Hydrolytically Stable Multivalent Ligands Bearing Thiodigalactoside Analogues for Peanut Lectin and Human Galectin-3 Binding," The Journal of Organic Chemistry, 2014.
Camby et al., "Galectin-1: a small protein with major functions," Glycobiology, vol. 16, No. 11, pp. 137R-157R, 2006.
Campo et al., "Design, synthesis and the effect of 1,2,3-triazole sialylmimetic neoglycoconjugates on *Trypanosoma cruzi* and its cell surface *trans*-sialidase," Bioorganic & Medicinal Chemistry, 20(2012), 145-156.
Capalbo et al., "Predictive Biomarkers for Checkpoint Inhibitor-Based Immunotherapy: The Galectin-3 Signature in NSCLCs," Int. J. Mol. Sci., 2019, 20, 1607.
Cedeno-Laurent et al., "Galectin-1 research in T cell immunity: Past, present and future," Clinical Immunology, (2012), 142, 107-116.
Chauhan et al., "A Novel Carbohydrate-Based Therapeutic GCS-100 Overcomes Bortezomib Resistance and Enhances Dexamethasone-Induced Apoptosis in Mulitple Myeloma Cells," Cancer Res, 2005, 65:18), Sep. 15, 2005, pp. 8350-8358.
Cheng et al., "Highter bone marrow *LGALS3* expression is an independent unfavorable prognostic factor for overall survival in patients with acute myeloid leukemia," Blood, Apr. 18, 2013, vol. 121, No. 16, pp. 3172-3181.
Collins et al., "Taloside Inhibitors of Galectin-1 and Galectin-3," Chem Biol Drug Des, 2012, 79:339-346.
Coxon et al., "Boat conformations Synthesis, NMR spectroscopy, and molecular dynamics of methyl 4,6-O-benzylidene-3-deoxy-3-phthalimido-α-D-altropyranoside derivatives," Carbohydrate Research, 331 (2001), 461-467.
Crich et al., "Direct Stereocontrolled Syntesis of 3-Amino-3-deoxy-β-Mannopyranoside: Importance of the Nitrogen Protecting on Tereoselectivity," J. Org. Chem, Jul. 6, 2007, 72(14): 5183-5192.
Cui et al., "Novel and Efficient Synthesis of Iminocoumarins via Copper-Catalyzed Multicomponent Reaction," Organic Letters, 2006, vol. 8, No. 20, 4517-4520.
Cumpstey et al., "$C_2$-Symmetrical Thiodigalactoside Bis-Benzamido Derivatives as High-Affinity Inhibitors of Galectin-3: Effienient Lectin Inhibition through Double-Arginine-Interactions," Angew. Chem. Int. Ed., 2005, 44, 5110-5112.
Demotte et al., "A Galectin-3 Ligand Corrects the Impaired Function of Human CD4 and CD8 Tumor-Infiltrating Lymphocytes and Favors Tumor Rejection in Mice," Cancer Res., 70(19), Oct. 1, 2010, pp. 7476-7488.
Deroo et al., "The role of galectin-3 and galectin-3-binging protein in venous thrombosis," Blood, Mar. 12, 2015, vol. 125, No. 11, 1813-1821.
Desmedt et al., "Galectin-3 in Renal Pathology: More Than Just an Innocent Bystander?," Am. J. Nephrol., 2016, 43:305-317.
Diaz et al., "Do galectins play a role in venous thrombosis? a review," Thrombosis Research, 125(2010), 373-376.
Dube-Delarosbil et al., "The emerging role of galectins in high-fatality cancers," Cell. Mol. Life Sci., (2018), 75:1215-1226.
Duckworth et al., "Galectins in the Blood Circulation: Potential Therapeutic Targets of Cancer Metastasis," in Galectins and Disease Implications for Targeted Therapeutics, ACS Symposium Series, American Chemical Society, Washington, DC, 2012.
English Abstract for DE 19643764, Apr. 2, 1998.
Garcia et al., "New Synthetic "Tricks." One-Pot Preparation of N-Substituted Phthalimides From Azides and Phthalic Anhydride," Tetrahedron Letters, vol. 27, No. 5, pp. 639-640, 1986.
Giguere et al., "Synthesis of stable and selective nhibitors of human galectin-1 and -3" Bioorganic & Medicinal Chemistry, 16(2008), 7811-723.
Giordano et al., "Galectins in hematological malignancies," Hematology, vol. 20, No. 4, Jul. 2013, 327-335.
Girard et al., "Clinical Trials and Applications of Galectin Antagonists," Trends in Glycoscience and Glycotechnology, vol. 30, No. 172, (Jan.-May 2018,. p. SE21-SE220.

(56) References Cited

OTHER PUBLICATIONS

Glinskii et al., "Mechanical Entrapment Is Insufficient and Intercellular Adhesion Is Essential for Metastatic Cell Arrest in Distant Organs," Neoplasia, vol. 7, No. 5 May 2005, pp. 522-527.
Greenwald et al., "Galectin-3-Mediated Xenoactivation of Human Monocytes," Transplantation, vol. 87, No. 1, Jan. 15, 2009, 44-51.
Guha et al., "Cod glycopeptide with picomolar affinity to galetin-3 suppresses T-cell apoptosis and prostate cancer metastasis," PNAS, Mar. 26, 2013, vol. 110, No. 13, 5052-5057.
Gunther et al., "Supporting Information for: Synthesis of 1,2,3-Triazol-Linked Glycoconjugates of N-(2-Aminoethyl)-Glycine. Building Blocks for the Construction of Combinatorial Glycopeptide Libraries," Journal of Synthetic Organic Chemistry (2014).
He et al., "Design, synthesis and evaluation of lactoside-derived galectin-3 inhibitors," Journal of Carbohydrate Chemistry, 2019, vol. 38, No. 3, 151-166.
Herrera-Rivero et al., "Dysregulation of TLR5 and TAM Ligands in the Alzheimer's Brain as Contributors to Disease Progression," Molecular Neurobiology, (2019), 56:6539-6550.
Huang et al., "Galectin-1 Upregulates CXCR4 to Promote Tumor Progression and Poor Outcome in Kidney Cancer," J Am Soc Nephrol, 25:1486-1495, 2014.
Ilmer et al., "Cell surface galectin-3 defines a subset of chemoresistant gastrointestinal tumor-inititating cancer cells with heightened stem cell characteristics," Cell Death and Disease, (2016)7, e2337, pp. 1-9.
International Search Report dated Apr. 23, 2020, for Application No. PCT/US2019/068597.
Ito et al., "Thiodigalactoside inhibits murine cancers by concurrently blocking effects of galectin-1 on immune dysregulation, angiogenesis and protection against oxidative stress," Angiogenesis, (2011), 14:293-307.
Jeftic et al., "Galectin-3 Ablation Enhances Liver Steatosis, but Attenuates Inflammation and IL-33-Dependent Fibrosis in Obsesogenic Mouse Model of Nonalcoholic Steatohepatitis," Mol Med, 21:453-465, 2015.
Kang et al., "Galectin-3 in patients with coronary heart disease and atrial fibrillation," Clinica Chimica Acta, 478(2018), 166-170.
Kassou et al., "Ring Contraction vs Fragmentation in the Intramolecular Reactions of 3-O-(Trifluoromethanesulfonyl)pyranosides. Efficient Synthesis of Branched-Chain Furanosides," J. Org. Chem., 1995, 60, 4353-4358.
Kato et al., "Targeting Galectin-3 to reverse integrin β3/KRAS-mediated tumor progression," Poster 105th Annual Meeting of the American Association for Cancer Research, Apr. 5-9, 2014.
Kayet et al., "1,5-Disubstituted 1,2,3-Triazolylation at C1, C2, C3, C4, and C6 of Pyranosides: A Metal-Free Route to Triazolylated Monosaccharides and Triazole-Linked Disaccharides," J. Org. Chem., 2013, 78, 9865-9875.
Klyosov et al., "Galectins in Disease and Potential Therapeutic Approaches," in Galectins and Disease Implications for Targeted Therapeutics, ACS Symposium Series, American Chemical Society: Washington, DC, 2012.
Kulkarni et al., "Exosomes Derived from HIV-1 Infected DCs Mediate Viral trans-Infection via Fibronectin and Galectin-3," Scientific Reports, 7:14787, 1-14, Nov. 1, 2017.
Lee et al., "Cooperative Interaction between Interleukin 10 and Galectin-3 against Liver Ischemia-Reperfusion Injury," Chemical Cancer Research, vol. 8, 217-220, Jan. 2002
Leffler et al., "Introduction to galectins," Glycoconj. J., 2002, 19(7-9), 433-440.
Leffler et al., "Low-Molecular Weight Inhibitors of Galectins in Galectins and Disease Implications for Targeted Therapeutics," ACS Symposium Series, American Chemical Society: Washington, DC 2012.
Levroney et al., "Novel Innate Immune Functions for Galectin-1: Galectin-1 Inhibits Cell Fusion by Nipah Virus Envelope Glycoproteins Proinflammatory Cytokines," The Journal of Immunology, 413-420 (2005).

Li et al., "Synthesis of allyl 4-O-{3-deoxy-3-[4-benzylaminocarbonyl-1H-(1,2,3)-triazol-1-yl]-β-D-glucopyranoside as a potential inhibitor of galectin-3,": Journal of Chinese Pharmaceutical Sciences, 17(2008), 209-214.
Li et al., "Hematopoietic-Derived Galectin-3 Causes Cellular and Systemic Insulin Resistance," Cell, Nov. 3, 2016, 167, 973-984.
Liu et al., "Galectins as Modulators of Tumour Progression," Nature, vol. 5, Jan. 2005, 29-41.
MacKinnon et al., "Regulation of Transforming Growth Factor-β1-driven Lung Fibrosis by Galectin-3," American Journal of Respitory and Critical Care Medicine, vol. 185, 2012, 537-546.
MacKinnon et al., "Design, Synthesis, and Applications of Galectin Modulators in Human Health," Top Med. Chem., Springer-Verlag Berlin Heidelberg, 2014.
Magnani et al., "Glycomimetic Drugs—A New Source of Therapeutic Opportunities," Discovery Medicine, vol. 8, No. 43, pp. 247-252, Dec. 2009.
Marco-Contelles et al., "N-Azole Substituted Carbohydrates. Synthesis and Transformations of 1-3'-Deoxy-1',2':5',6'-di-O-isoprophylidene-α-D-glucofuranos-3'yl)-Azole Derivatives," Tetrahedron, 55(1999), 10511-10526.
Markowska et al., "Galectin-3 is an important mediator of VEGF- and bFGFmediated angiogenic response," J. Exp. Med., vol. 207, No. 9, 2010, 1981-1993.
Markowska et al., "Glycobiology of ocular angiogenesis," Glycobiology, Vo. 24, No. 12, pp. 1275-1282, 2014.
Mendonca et al., "Lack of Galectin-3 attentuates neuroinflammation and protects the retina and optic nerve of diabetic mice," Brain Research, 1700(2018), 126-137.
Mirandola et al., "Targeting Galectin-3 Unveils the Complexity of Multiple Myeloma: A Sweet Context," in Galectins and Disease Implications for Targeted Therapeutics, ACS Symposium Series, American Chemical Society, 2012.
Moura et al., "Different expression patterns of *LGALS1* and *LGALS3* in polycythemia vera, essential thrombocythemia and primary myelofibrosis," J Clin Pathol, 2016, 69:926-929.
Nagae et al., "Structural Analysis of the Human Galectin-9-N-terminal Carbohydrate Recognition Domain Reveals Unexpected Properties that Differ from the Mouse Orthologue," J. Mol. Biol., (2008), 375, 119-135.
Nemr et al., "α- and β-hydrogen eliminations in the reactions of some 3-O-triflylglycosides with ᵗBuOK and pyridine," Carbohydrate Research, 303(1997), 267-281.
Newlaczyl et al., "Galectin-3—A jack-of-all-trades in cancer," Cancer Letters, 313, 2011, 123-128.
Oberg et al., "Copper-Free Huisgen 1,3-Dipolar Cycloaddition to 3-Benzotriazolo-3-Deoxy-β-D-Galactopyranoside: Cyclization of a Galactopyranoside Azide and Benzyne," Trends in Carbohydrate Research, vol. 2, No. 2, (2010), 1-4.
Otero et al., "Synthesis of new iso-C-nucleoside analogues from 2-(methyl2-O-benzl-4,6-O-benzylidene-3-deoxy-α-D-altropyranosid-3-yl)ethanal," Carbohydrate Research, 340(2005), 547-555.
Ouellet et al., "Galectin-1 Acts as a Soluble Host Factor That Promotes HIV-1 Infectivity through Stabilization of Virus Attachment to Host Cells," The Journal of Immunology, 2005, 174:4120-41261.
Peacock et al., "Emergency Department Use of Galectin-3," Critical Pathways in Cardiology, vol. 13, No. 2, Jun. 2014, 73-77.
Prescher et al., "Supporting Information for: Discovery of multifold modified sialosides as *human* CD22/Siglec-2 ligands with nanomolar activity on B-cells," ACS Chem Biol., Jul. 18, 2014;9(7):1444-1450I.
Pugliese et al., "Galectin-3 in diabetic patients," Clin Chem Lab Med, 2014, 52(10), 1413-1423.
Rabinovich et al., "Synthetic Lactulose amines: novel class of anticancer agents that induce tumor-cell apoptosis and inhibit galectin-mediated homotypic cell aggregation and endothelial cell morphogenesis," Glycobology, vol. 16, No. 3, pp. 210-220, 2006.
Rabinovich et al., "Galectins and microenvironmental niches during hematopoiesis," Current Opinion in Hematology, 2011, 18:443-451.
Rabinovich et al., "Shaping the Immune Landscape in Cancer by Galectin-Driven Regulatory Pathways," J Mol Biol, (2016), 428, 3266-3281.

(56) References Cited

OTHER PUBLICATIONS

Rajput et al., "Synthesis and evaluation of iminooumaryl and coumaryl derivatized glycosides as galectin antagonists," Bioorganic & Medicinal Chemistry Letters, 24(2014), 3516-3520.

Rajput et al., "A Selective Galactose-Coumarin-Derived Galectin-3 Inhibitor Demonstrates Involvement of Galectin-3-glycan Interactions in a Pulmonary Fibrosis Model," J. Med. Chem., 2016, 59, 8141-8147.

Raymond et al., "Translational Rational for the Clinical Development of OTX-008: A Novel Drug That Inhibits Galectin-1 Expression in Human Cancer Models," in Galectins and Disease Implications for Targeted Therapeutics, ACS Symposium Series, American Chemical Society 2012.

Ruvolo et al., "Role of MSC-derived galectin 3 in the AML microenvironment," Molecular Cell Research, 1865, (2018), 959-969.

Salameh et al., "3-(1,2,3-Triazol-1-yl)-1-thio-galactosides as small, efficient, and hydrolytically stable inhibitors of galectin-3" Bioorganic & Medicinal Chemistry Letters, 15, (2005), 3344-3346.

Salameh et al., "1*H*-1,2,3-Triazol-1-yl thiodigalactoside derivatives as high affinity inhibitors," Bioorg. Med. Chem., 18, (2010), 5367-5378.

Salatino et al., "Fine-Tuning Antitumor Responses Through the Control of Galectin-Glycan Interactions: An Overview," Suppression and Regulation of Immune Responses, Methods in Molecular Biology, vol. 677, Maria Cristina Cuturi and Igacio Anegon (eds.), Springer Science+Business Media, LLC, 2011.

Salomonsson et al., "Monovalent Interactions of Galectin-1," Biochemistry, 2010, 49, 9518-9532.

Seetharaman et al., "X-ray Crystal Structure of the Human Galectin-3 Carbohydrate Recognition Domain at 2.1-Å Resolution," The Journal of Biological Chemistry, vol. 273, No. 21, Issue of May 22, pp. 13047-135052, 1998.

Seguin et al., "An integrin $\beta_3$-KRAS-RalB complex drives tumour stemness and resistance to EGFR inhibition," Nature Cell Biology, 2014, 1-14.

Smith et al., "Synthetic Approaches to Nogalamycin-Related Anthracyclines. Approach to a Western Synthon," J. Org. Chem., 1987, 52, 3566-3573.

Song et al., "Overexpressed Galectin-3 in Pancreatic Cancer Induces Cell Proliferation and Invasion by Binding Ras and Activation Ras Signaling," Plos One, Aug. 2012, vol. 7, Issue 8, e42699.

Stannard et al., "Galectin inhibitory disaccharides promote tumour immunity in breast cancer model," Cancer Letters, 299, (2010), 95-110.

Streetly et al., "GCS-100, a novel galectin-3 antagonist, modulates MCL1, NOXA, and cell cycle to induce myeloma cell death," Blood, May 13, 2010, vol. 115, No. 19, 3939-3948.

Taniguchi et al., "Serum Levels of Galectin-3: Possible Association with Fibrosis, Aberrant Angiogenesis, and Immune Activation in Patients with Systemic Sclerosis," The Journal of Rheumatology, 2012: 39:3, 539-544.

Tejler et al., "Synthesis of galactose-mimicking 1*H*-(1,2,3-triazol-1-yl)-mannosides as selective galectin-3 and 9N inhibitors," Carbohydrate Research, 342(2007), 1869-1875.

Tejler et al., "Fragment-based development of trizole-substituted *O*-galactosyl aldoximimes with fragment-induced faffinity and selectivity for galectin-3," Org. Biomol. Chem., 2009, 7, 3982-3990.

Van Den Brule et al., "Expression of galectins in cancer: A critical review," Glycoconjuctat Jouranl, 19, 537-542, 2004.

Van Der Velde et al., "Galectin-3 and sST2 in prediction of left ventricular ejection fraction after myocardial infarction," Clinica Chimica Acta, 452, (2016), 50-57.

Van Hattum et al., "Tuning the preference of thiodigalactoside- and lactosamine-based ligands to galectin-3 over galectin-1," J. Med. Chem., 2013, 56, 1350-1354.

Van Scherpenzeel et al., "Synthesis and Evaluation of New Thiodigalactoside-Based Chemical Probes to Label Galectin-3," ChemBioChem, 2009, 10, 1724-1733.

Wagdy et al., "Subclinical myocardial injury during vaso-occlusive crisis in pediatric sickle cell disease," European Journal of Pediatrics, (2018), 177:1745-1752.

Walker et al., "Investigating carbohydrate based ligands for galectin-3 with docking and molecular dynamics studies," Jouranl of Molecular Graphics and Modelling, 71, (2017), 211-217.

Wang et al., "Design and synthesis of glycoprotein-based multivalent glycol-ligands for influenza hemagglutinin and human galectin-3," Bioorganic & Medicinal Chemistry, 21, (2013), 2037-2044.

Wang et al., "Galectin-3 promotes HIV-1 budding via association with Alix and Gag p6," Glycobiology, vol. 24, No. 11, pp. 1022-1035, 2014.

Wiecikowski et al., "Ligand-free method to produce the anti-angiogenic recombinant Galectin-3 carbohydrate recognition domain," Protein Expression and Purification, 144, (2018), 19-24.

Yu et al., "Genetic and Pharmacological Inhibition of Galectin-3 Prevents Cardiac Remodeling by Interfering With Myocardial Fibrogenesis," Circ. Heart Fail., Jan. 2013, 107-117.

Zhang et al., "RN1, a novel galectin-3 inhibitor, inhibits pancreatic cancer cell growth in vitro and in vivo via blocking galectin-3 associated signaling pathways," Oncogene, (2017) 36, 1297-1308.

Zhao et al., "Circulating Galectin-3 Promotes Metastasis by Modifying MUC1 Localization on Cancer Cell Surface," Ca⊗ncer Res, 2009, 69:(17), Sep. 1, 2009, 6799-6806.

Zhao et al., "Galectin-3 Mediates Tumor Cell-Stroma Interactions by Activation Pancreatic Stellate Cells to Produce Cytokins via Integrin Signaling," Gastroenterology, 2018, 154:1524-1537.

Zhu et al., "The Tim-3 ligand galectin-9 negatively regulates T helper type 1 immunity," Nature Immunology, vol. 6, No. 12, Dec. 2005, 1245-1252.

Zhuang et al., "Structure determination of a Galectin-3-carbohydrate complex using paramagnetism-based NMR constraints," Protein Science, 2008, 17:1220-1231.

Zuberi et al., "Critical Role for Galectin-3 in Airway Inflammation and Bronchial Hyperresponsiveness in a Murine Model of Asthma," American Journal of Pathology, vol. 165, No. 6, Dec. 2004, 2045-2053.

Zucchetti et al., "Pharmacokinetics and antineoplastic activity of galectin-1-targeting OTX008 in combination with sunitinib," Cancer Chemother Pharmacol, (2013), 72:879-887.

\* cited by examiner

Synthesis of Compounds 13 and 14 (Esters and Acids)

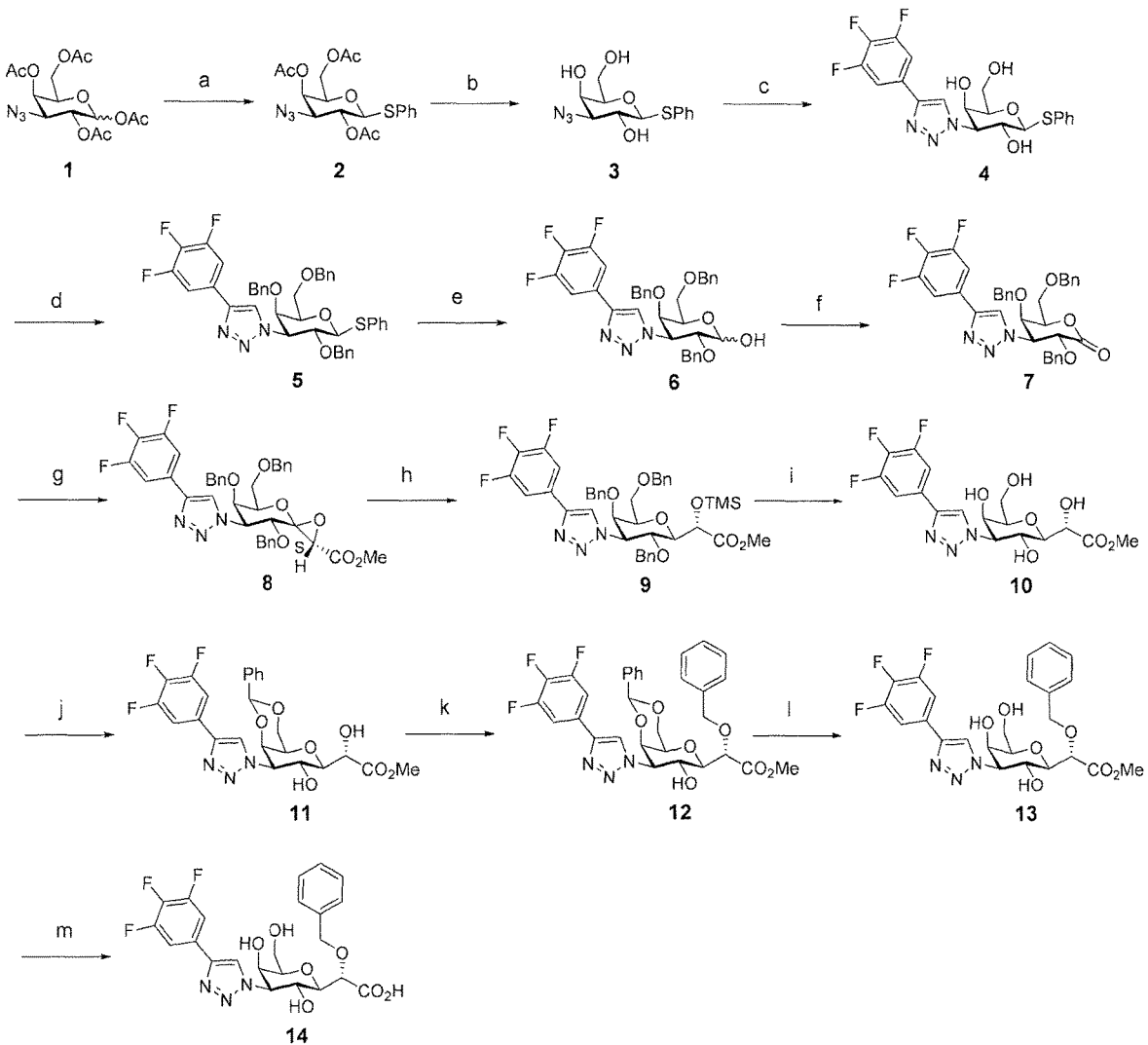

a) PhSH, BF$_3$OEt$_2$, DCM, 0°C, 65%; b) NaOMe, MeOH, rt; c) 3,4,5-trifluorophenyl-1-acetylene, CuSO$_4$, THPTA, sodium ascorbate, MeOH, water, rt, 100% for 2 steps; d) NaH, BnBr, DMF, 0°C to rt, 94%; e) trichloroisocyanuric acid, acetone, water, rt, 95%; f) Dess-Martin periodinane, DCM, 0°C to rt, 52%; g) methyl bromoacetate, LiHMDS, THF, -78°C, 64%; h) Bu$_3$SnH, TMSOTf, DCM, 0°C to rt, 48%; i) Et$_3$SiH, Pd(OH)$_2$/C, MeOH, 0°C to rt, 73%; j) PhCH(OMe)$_2$, CSA, CH$_3$CN, 80%; k) BnBr, NaH, DMF, 0°C to rt, 21%; l) CSA, MeOH, reflux, 80%; m) NaOH, MeOH, H$_2$O, rt, 90%

FIG. 1

Synthesis of Compound 16 (Preparation of Amides: Procedure A)

a) i. MeNH₂, THF, 76°C; ii. CSA, MeOH, 76°C, 68% for 2 steps

Synthesis of Compound 24 (Preparation of Amides: Procedure B)

a) MeNH₂, THF, 76°C, 88%; b) 4-F-BnBr, NaH, DMF, 0°C to rt, 47%; c) CSA, MeOH, 78°C, 66%

Synthesis of Compounds 40 and 41 (Preparation of Ethers)

a) CH₃I, NaH, DMF, rt; b) CSA, MeOH, 78°C, 66%

Synthesis of Compound 48 (Preparation of Sulfides)

a) TBSCl, imidazole, DMF, 0°C; b) Ac₂O, pyridine, rt; c) TBAF, THF, rt; d) SOBr₂, DCM, 0°C; e) NaH, benzylthiol, DMF;
f) i. MeNH₂, THF, reflux, ii. CSA, MeOH, reflux Synthesis of Compound 49 a) Ac₂O, pyridine; b) i. TMSI, DCM, 0°C, ii. dimethylmalonate, NaHMDS, 15-c-5, THF, rt; c) NaH, phenethyl bromide, DMF; d) i. NaOH, H₂O, MeOH, ii. HOAc, 100°C; e) H₂, Pd/C, MeOH; f) MeNH₂, HATU, DMF

GALECTIN-3 INHIBITING C-GLYCOSIDES

This application is a national stage filing under 35 U.S.C. § 371 of International Application No. PCT/US2019/068597, filed Dec. 26, 2019, which claims the benefit under 35 U.S.C. § 119(e) to U.S. Provisional Application No. 62/927,192, filed Oct. 29, 2019, and U.S. Provisional Application No. 62/785,588, filed Dec. 27, 2018, which applications are incorporated by reference herein in their entirety.

Compounds, compositions, and methods for treating and/or preventing at least one disease, disorder, and/or condition associated with galectin-3 activity including, for example, inflammatory diseases, fibrosis, and cancers, are disclosed herein.

When a tissue is infected or damaged, the inflammatory process directs leukocytes and other immune system components to the site of infection or injury. Within this process, leukocytes play an important role in the engulfment and digestion of microorganisms. The recruitment of leukocytes to infected or damaged tissue is critical for mounting an effective immune defense.

Galectins are proteins with a characteristic carbohydrate recognition domain (CRD) (Barondes, S H., Cooper, D. N. W., Gitt, M. A., and Leffler, H. (1994). Galectins. Structure and function of a large family of animal lectins. *J. Biol. Chem.* 2-69:2.0807-20810 Leffler, H., Carlsson, S., Hedlund, M., Qlan, Y, and Poirier, F. (2004) Introduction to galectins. *Glycoconj. J.* 19: 433-440). Galectin subunits can contain either one or two CRDs within a single peptide chain. The mono-CRDs galectins can occur as monomers or dimers in vertebrates. Galectin-3 is a monomer in solution but may aggregate and become multimeric upon encounter with ligands. Galectins are synthesized as cytosolic proteins. Evidence suggests roles for galectins in inflammation, fibrosis, cancer, and other disorders (see, e.g., U.S. Pat. No. 7,638,623).

A pro-inflammatory role of galectin-3 is indicated by its induction in cells at inflammatory sites, effects on immune cells, and decrease of the inflammatory response shown in animal models. Inflammation is a protective response of the body to invading organisms and tissue injury. However, if unbalanced, frequently it is also destructive and occurs as part of the pathology in many diseases. Because of this, there is great medical interest in pharmacological modulation of galectin-3 mediated inflammation.

Immunohistochemical studies show changed expression of certain galectins in cancer. Direct evidence for a role of galectin-3 in cancer comes from mouse models. In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion.

Both natural and synthetic modulators of galectin-3 have been identified. However, natural compounds that have been identified as galectin-3 ligands are not suitable for use as active components in pharmaceutical compositions, because they have been reported to have low activity and specificity for galectins and galectin-3. As natural products they are difficult to produce as well-characterized drugs and are susceptible to acidic hydrolysis in the stomach and to enzymatic degradation. In addition, previously identified natural galectin-3 modulators are large and hydrophilic in nature, and are not readily absorbed from the gastrointestinal tract following oral administration.

Accordingly, there is a need in the art for inhibitors of galectin-3 mediated function. The present disclosure may fulfill one or more of these needs and/or may provide other advantages.

Compounds, compositions, and methods for treating and/or preventing (i.e., reducing the likelihood of occurrence or reoccurrence) at least one disease, disorder, and/or condition in which inhibiting binding of galectin-3 to one or more ligands may play a role are disclosed.

Disclosed is at least one compound chosen from compounds of Formula (I):

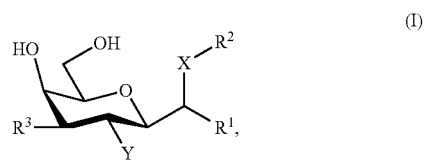

prodrugs of compounds of Formula (I), and pharmaceutically acceptable salts of any of the foregoing, wherein $R^1$, $R^2$, $R^3$, X, and Y are defined herein.

As used herein, "compound of Formula (I)" includes compounds of Formula (I), pharmaceutically acceptable salts of compounds of Formula (I), prodrugs of compounds of Formula (I), and pharmaceutically acceptable salts of prodrugs of compounds of Formula (I).

In some embodiments, compositions comprising at least one compound of Formula (I) and optionally at least one additional pharmaceutically acceptable ingredient are presented. In some embodiments, the compositions are pharmaceutical compositions.

In some embodiments, a method for treatment and/or prevention of at least one disease, disorder, and/or condition where inhibition of galectin-3 mediated functions is useful is disclosed, the method comprising administering to a subject in need thereof an effective amount of at least one compound of Formula (I) and/or a pharmaceutical composition comprising at least one compound of Formula (I).

In the following description, certain specific details are set forth in order to provide a thorough understanding of various embodiments. However, one skilled in the art will understand that the disclosed embodiments may be practiced without these details. In other instances, well-known structures have not been shown or described in detail to avoid unnecessarily obscuring descriptions of the embodiments. These and other embodiments will become apparent upon reference to the following detailed description and attached drawings.

BRIEF DESCRIPTION OF THE DRAWINGS

FIG. 1 is a diagram illustrating the synthesis of Compounds 13 and 14.

Figure 2A:
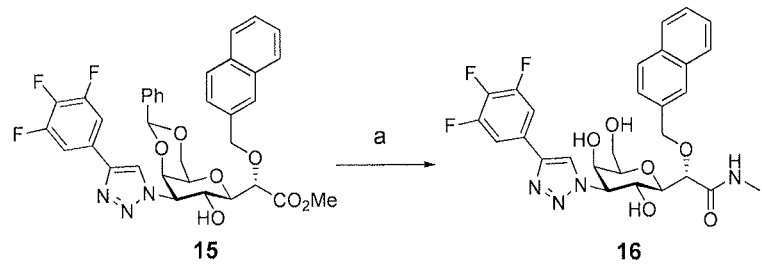
FIG. 2A is a diagram illustrating the synthesis of Compound 16.

Disclosed herein are inhibitors of galectin-3, pharmaceutical compositions comprising the same, and methods for inhibiting galectin-3 mediated functions using the same. The compounds and compositions of the present disclosure may be useful for treating and/or preventing at least one disease, disorder, and/or condition that is treatable by inhibiting binding of galectin-3 to one or more ligands.

In some embodiments, disclosed is at least one compound chosen from compounds of Formula (I):

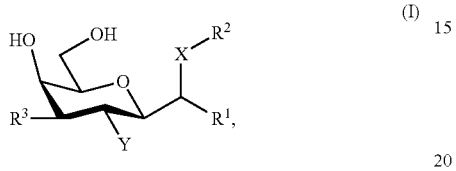

(I)

prodrugs of compounds of Formula (I), and pharmaceutically acceptable salts of any of the foregoing,
wherein
$R^1$ is chosen from —CN, —CH$_2$CN, and —C(=O)Q groups, wherein Q is chosen from —OZ$^1$, —NHOH, —NHOCH$_3$, —NHCN, and —NZ$^1$Z$^2$ groups, wherein $Z^1$ and $Z^2$, which may be identical or different, are independently chosen from H, C$_{1-8}$ alkyl, C$_{2-12}$ heterocyclyl, C$_{6-18}$ aryl, and C$_{1-3}$ heteroaryl groups, wherein the C$_{2-12}$ heterocyclyl, C$_{6-18}$ aryl, and C$_{1-13}$ heteroaryl groups are optionally substituted with one or more groups independently chosen from halo, C$_{1-8}$ alkyl, C$_{1-8}$ hydroxyalkyl, C$_{1-8}$ haloalkyl, C$_{6-18}$ aryl, —OT$^1$, —C(=O)OT$^1$, —C(=O)) NT$^1$T$^2$, —CN, —ST$^1$, S(O)T$^1$, and —SO$_2$T$^1$ groups, wherein T$^1$ and T$^2$, which may be identical or different, are independently chosen from H, C$_{1-8}$ alkyl, and C$_{1-8}$ haloalkyl groups, or T$^1$ and T$^2$ join together along with the nitrogen atom to which they are attached to form a ring, or Z$^1$ and Z$^2$ join together along With the nitrogen atom to which they are attached to form a ring;
$R^2$ is chosen from H, C$_{1-8}$ alkyl, C$_{2-8}$ alkenyl, C$_{2-8}$ alkynyl, C$_{1-8}$ haloalkyl, C$_{2-8}$ haloalkenyl, C$_{2-8}$ haloalkynyl, C$_{4-16}$ cycloalkylalkyl, C$_{6-18}$ aryl, C$_{1-13}$ heteroaryl, C$_{7-19}$ arylalkyl, and C$_{2-14}$ heteroarylalkyl groups, wherein the C$_{1-8}$ alkyl, C$_{2-8}$ alkenyl, C$_{2-8}$ alkynyl, C$_{1-8}$ haloalkyl, C$_{2-8}$ haloalkenyl, C$_{2-8}$ haloalkynyl, C$_{4-16}$ cycloalkylalkyl, C$_{6-18}$ aryl, C$_{1-13}$ heteroaryl, C$_{7-9}$ arylalkyl, and C$_{2-14}$ heteroarylalkyl groups are optionally substituted with one or more groups independently chosen from halo, C$_{1-8}$ alkyl, C$_{1-8}$ hydroxyalkyl, C$_{1-8}$ haloalkyl, C$_{6-18}$ aryl, —OZ$^3$, —C(=O)OZ$^3$, —C(=O)NZ$^3$Z$^4$, and —SO$_2$Z$^3$, groups, wherein Z$^3$ and Z$^4$, which may be identical or different, are independently chosen from H, C$_{1-8}$ alkyl, and C$_{1-8}$ haloalkyl groups, or Z$^3$ and Z$^4$ join together along with the nitrogen atom to which they are attached to form a ring;
$R^3$ is chosen from C$_{6-18}$ aryl and C$_{1-13}$ heteroaryl groups, wherein the C$_{6-18}$ aryl and C$_{1-13}$ heteroaryl groups are optionally substituted with one or more groups independently chosen from R$^4$, C$_{1-8}$ alkyl, C$_{1-8}$ haloalkyl, —C(=O)OZ$^5$, and —C(O)NZ$^5$Z$^6$ groups, wherein R$^4$ is independently chosen from C$_{6-18}$ aryl groups optionally substituted with one or more groups independently chosen from halo, C$_{1-8}$ alkyl —OZ$^7$, —C(=O)OZ$^7$, and —C(=O)NZ$^7$Z$^8$ groups, wherein Z$^5$, Z$^6$, Z$^7$ and Z$^8$, which may be identical or different, are independently chosen from H and C$_{1-8}$ alkyl groups, or Z$^5$ and Z$^6$ join together along with the nitrogen atom to which they are attached to form a ring and/or Z$^7$ and Z$^8$ join together along with the nitrogen atom to which they are attached to form a ring;
X is chosen from —O—, —S—, —C—, and —N(R$^5$)—, wherein R$^5$ is chosen from H, C$_{1-8}$ alkyl, C$^{2-8}$ alkenyl, C$_{2-8}$ alkynyl, C$_{1-8}$ haloalkyl, C$_{2-8}$ haloalkenyl, and C$_{2-8}$ haloalkynyl groups;
Y is chosen from H, halo, and —OZ$^9$ groups, wherein Z$^9$ is chosen from H and C$_{1-8}$ alkyl groups; and
wherein each of Z$^1$, Z$^2$, Z$^3$, Z$^4$, Z$^5$, Z$^6$, Z$^7$, Z$^8$, Z$^9$, T$^1$, and T$^2$ is optionally substituted with one or more groups independently chosen from halo and —OR$^6$ groups, wherein R$^6$ is independently chosen from H and C$_{1-8}$ alkyl groups.

In some embodiments, the compound of Formula I is chosen from compounds of Formula (IA):

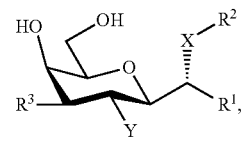

prodrugs of Formula (IA), and pharmaceutically acceptable salts of any of the foregoing.

In some embodiments, the compound of Formula I is chosen from compounds of Formula (IA).

In some embodiments, the compound of Formula I is chosen from compounds of Formula (IB):

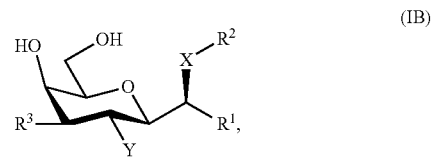

(IB)

prodrugs of Formula (IA), and pharmaceutically acceptable salts of any of the foregoing.

In some embodiments, the compound of Formula I is chosen from compounds of Formula (IB).

In some embodiments, R$^1$ is chosen from —CN, —CH$_2$CN, and —C(=O)Q groups, wherein Q is chosen from —OZ$^1$, —NHOH, —NHOCH$_3$, —NHCN, and —NZ$^1$Z$^2$ groups, wherein Z$^1$ and Z$^2$, which may be identical or different, are independently chosen from H and C$_{1-8}$ alkyl groups, or Z$^1$ and Z$^2$ join together along with the nitrogen atom to which they are attached to form a ring.

In some embodiments, R$^1$ is chosen from —C(=O)Q groups, wherein Q is chosen from —OZ$^1$, —NHOH, —NHOCH$_3$, —NHCN, and —NZ$^1$Z$^2$ groups, wherein Z$^1$ and Z$^2$, which may be identical or different, are independently chosen from H and C$_{1-8}$ alkyl groups, or Z$^1$ and Z$^2$ join together along with the nitrogen atom to which they are attached to form a ring.

In some embodiments, R$^1$ is chosen from —C(=O)Q groups, wherein Q is chosen from —OZ$^1$ and —NZ$^1$Z$^2$ groups. In some embodiments, R$^1$ is chosen from —C(=O)Q groups, wherein Q is chosen from —OZ groups. In some embodiments, $R^1$ is chosen from —(C(=O)Q groups, wherein Q is chosen from —$NZ^1Z^2$ groups.

In some embodiments, $R^1$ is chosen from —C(=O)Q groups, wherein Q is chosen from —$NZ^1Z^2$ groups, wherein $Z^1$ and $Z^2$, which may be identical or different, are independently chosen from H, $C_{1-8}$ alkyl, $C_{2-12}$ heterocyclyl, $C_{6-18}$ aryl, and $C_{1-13}$ heteroaryl groups.

In some embodiments, $R^1$ is chosen from —C(=O)Q groups, wherein Q is chosen from —$NZ^1Z^2$ groups, wherein $Z^1$ and $Z^2$, which may be identical or different, are independently chosen from H and $C_{1-8}$ alkyl groups.

In some embodiments, $R^1$ is chosen from —C(=O)Q groups, wherein Q is chosen from —$NZ^1Z^2$ groups, wherein $Z^1$ and $Z^2$, which may be identical or different, are independently chosen from H, $C_{2-12}$ heterocyclyl, $C_{6-18}$ aryl, and $C_{1-13}$ heteroaryl groups.

In some embodiments, $R^1$ is chosen from —C(=O)Q groups, wherein Q is chosen from —$NZ^1Z^2$ groups, wherein $Z^1$ and $Z^2$, which may be identical or different, are independently chosen from H and $C_{2-12}$ heterocyclyl groups.

In some embodiments, $R^1$ is chosen from —C(=O)Q groups, wherein Q is chosen from —$NZ^1Z^2$ groups, wherein $Z^1$ and $Z^2$, which may be identical or different, are independently chosen from H and $C_{6-18}$ aryl groups.

In some embodiments, $R^1$ is chosen from —C(=O)Q groups, wherein Q is chosen from —$NZ^1Z^2$ groups, wherein $Z^1$ and $Z^2$, which may be identical or different, are independently chosen from H and $C_{1-13}$ heteroaryl groups.

In some embodiments, at least one of $Z^1$ and $Z^2$ is H. In some embodiments, each of $Z^1$ and $Z^2$ is H. In some embodiments, only one of $Z^1$ and $Z^2$ is H. In some embodiments, at least one of $Z^1$ and $Z^2$, which may be identical or different, is independently chosen from $C_{1-8}$ alkyl, $C_{2-12}$ heterocyclyl, $C_{6-18}$ aryl, and $C_{1-13}$ heteroaryl groups. In some embodiments, $Z^1$ is H and $Z^2$ is chosen from $C_{1-8}$ alkyl, $C_{2-12}$ heterocyclyl, $C_{6-18}$ aryl, and $C_{1-13}$ heteroaryl groups. In some embodiments, $Z^1$ is H and $Z^2$ is chosen from $C_{1-8}$ alkyl groups. In some embodiments, $Z^1$ is H and $Z^2$ is chosen from $C_{2-12}$ heterocyclyl groups. In some embodiments, $Z^1$ is H and $Z^2$ is chosen from $C_{6-18}$ aryl groups. In some embodiments, $Z^1$ is H and $Z^2$ is chosen from $C_{1-13}$ heteroaryl groups.

In some embodiments, at least one of $Z^1$ and $Z^2$, which may be identical or different, is independently chosen from $C_{1-8}$ alkyl groups. In some embodiments, each of $Z^1$ and $Z^2$, which may be identical or different, is independently chosen from $C_{1-8}$ alkyl groups. In some embodiments, only one of $Z^1$ and $Z^2$ is chosen from $C_{1-8}$ alkyl groups. In some embodiments, at least one of $Z^1$ and $Z^2$, which may be identical or different, is independently chosen from $C_{1-6}$ alkyl groups. In some embodiments, each of $Z^1$ and $Z^2$, which may be identical or different, is independently chosen from $C_{1-6}$ alkyl groups. In some embodiments, only one of $Z^1$ and $Z^2$ is chosen from $C_{1-6}$ alkyl groups. In some embodiments, at least one of $Z^1$ and $Z^2$, which may be identical or different, is independently chosen from $C_{1-4}$ alkyl groups. In some embodiments, each of $Z^1$ and $Z^2$, which may be identical or different, is independently chosen from $C_{1-4}$ alkyl groups. In some embodiments, only one of $Z^1$ and $Z^2$ is chosen from $C_{1-4}$ alkyl groups. In some embodiments, at least one of $Z^1$ and $Z^2$, which may be identical or different, is independently chosen from methyl, ethyl, propyl, and butyl groups. In some embodiments, each of $Z^1$ and $Z^2$, which may be identical or different, is independently chosen from methyl, ethyl, propyl, and butyl groups. In some embodiments, only one of $Z^1$ and $Z^2$ is chosen from methyl, ethyl, propyl, and butyl groups. In some embodiments, $Z^1$ is H and $Z^2$ is chosen from methyl, ethyl, propyl, and butyl groups In some embodiments, at least one of $Z^1$ and $Z^2$, which may be identical or different, is independently chosen from $C_{2-12}$ heterocyclyl groups. In some embodiments, at least one of $Z^1$ and $Z^2$, which may be identical or different, is independently chosen from $C_{2-8}$ heterocyclyl groups. In some embodiments, at least one of $Z^1$ and $Z^2$, which may be identical or different, is independently chosen from $C_{4-6}$ heterocyclyl groups.

In some embodiments, at least one of $Z^1$ and $Z^2$, which may be identical or different, is independently chosen from $C_{6-18}$ aryl groups. In some embodiments, at least one of $Z^1$ and $Z^2$, which may be identical or different, is independently chosen from $C_{6-12}$ aryl groups. In some embodiments, at least one of $Z^1$ and $Z^2$, which may be identical or different, is independently chosen from $C_{6-10}$ aryl groups.

In some embodiments, at least one of $Z^1$ and $Z^2$, which may be identical or different, are independently chosen from $C_{1-13}$ heteroaryl groups. In some embodiments, at least one of $Z^1$ and $Z^2$, which may be identical or different, are independently chosen from $C_{1-9}$ heteroaryl groups. In some embodiments, at least one of $Z^1$ and $Z^2$, which may be identical or different, are independently chosen from $C_{1-5}$ heteroaryl groups.

In some embodiments, $R^1$ is chosen from

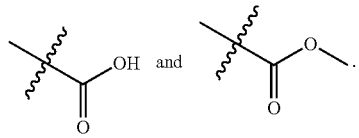

In some embodiments, $R^1$ is

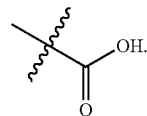

In some embodiments, $R^1$ is

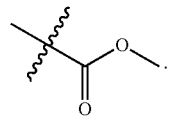 [SMILES: *C(=O)OC]

In some embodiments, $R^1$ is chosen from

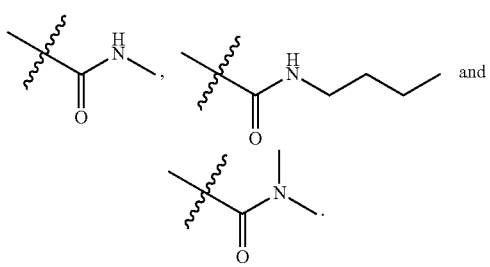

In some embodiments, R¹ is
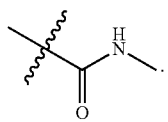 [SMILES: *C(=O)NC]
In some embodiments, R¹ is
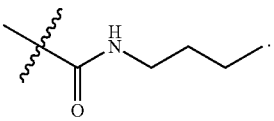 [SMILES: *C(=O)NCCCC]
In some embodiments, R¹ is
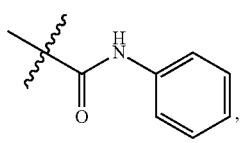 [SMILES: *C(=O)Nc1ccccc1]
In some embodiments, R¹ is chosen from
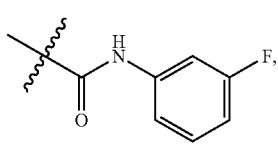 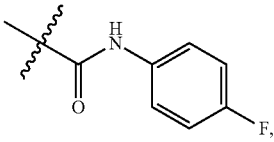
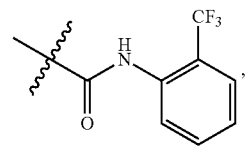 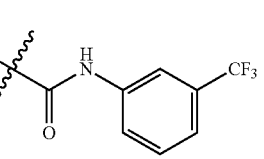
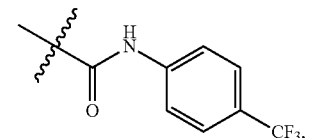
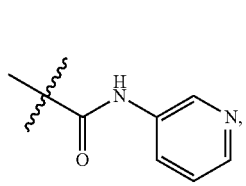 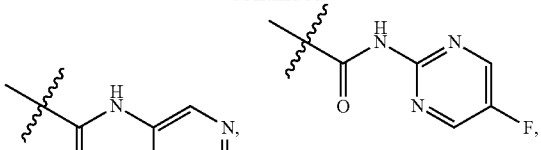
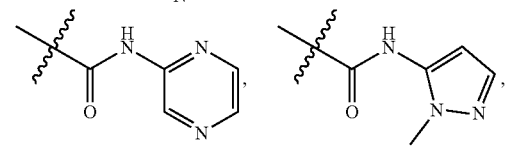
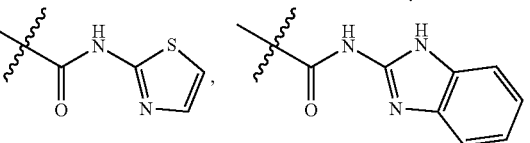
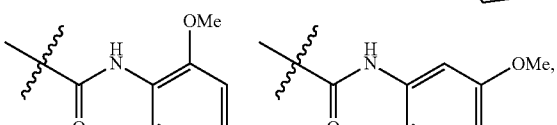
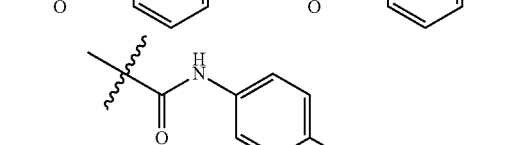
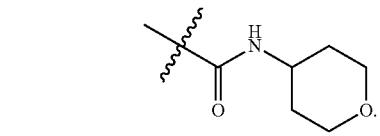 and
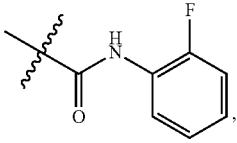 [SMILES: *C(=O)Nc1ccccc1F]
In some embodiments, R¹ is
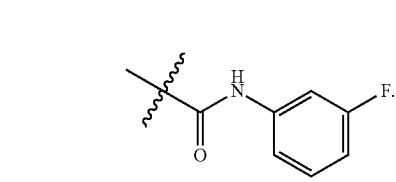 [SMILES: *C(=O)Nc1cccc(F)c1]
In some embodiments, R¹ is
(image of anilide with 2-F)
In some embodiments, R¹ is
(image of anilide with 3-F)

In some embodiments, R¹ is
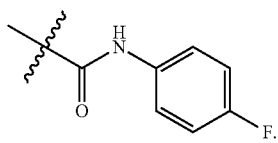 [SMILES: *C(=O)Nc1ccc(F)cc1]
In some embodiments, R¹ is
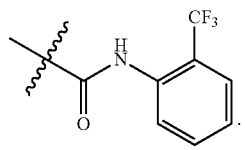
In some embodiments, R¹ is
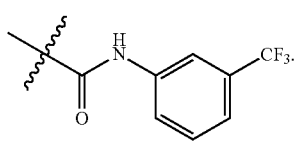 [SMILES: *C(=O)Nc1cccc(C(F)(F)F)c1]
In some embodiments, R¹ is
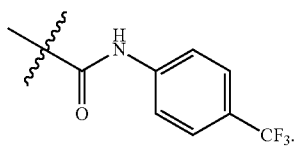 [SMILES: *C(=O)Nc1ccc(C(F)(F)F)cc1]
In some embodiments, R¹ is
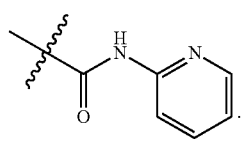
In some embodiments, R¹ is
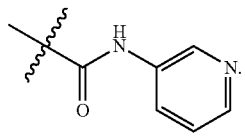 [SMILES: *C(=O)Nc1cccnc1]
In some embodiments, R¹ is
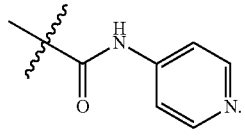 [SMILES: *C(=O)Nc1ccncc1]
In some embodiments, R¹ is
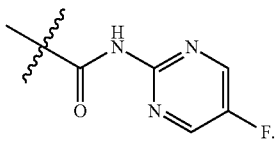 [SMILES: *C(=O)Nc1ncc(F)cn1]
In some embodiments, R¹ is
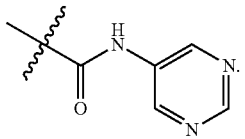 [SMILES: *C(=O)Nc1cncnc1]
In some embodiments, R¹ is
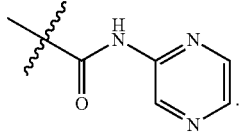
In some embodiments, R¹ is
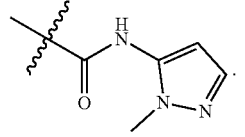 [SMILES: *C(=O)Nc1ccnn1C]
In some embodiments, R¹ is
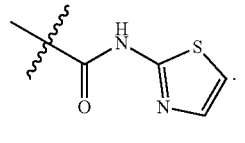 [SMILES: *C(=O)Nc1nccs1]
In some embodiments, R¹ is
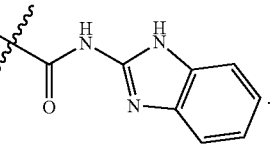
In some embodiments, R¹ is
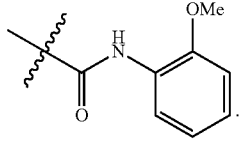

In some embodiments, R¹ is

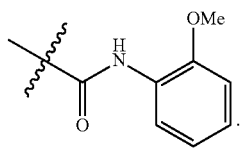 [SMILES: *C(=O)Nc1ccccc1OC]

In some embodiments, R¹ is

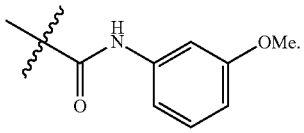 [SMILES: *C(=O)Nc1cccc(OC)c1]

In some embodiments, R¹ is

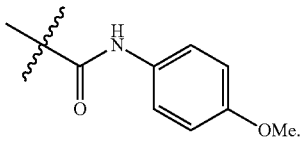 [SMILES: *C(=O)Nc1ccc(OC)cc1]

In some embodiments, R¹ is

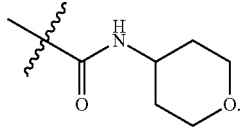 [SMILES: *C(=O)NC1CCOCC1]

In some embodiments, R² is chosen from H, $C_{1-8}$ alkyl, $C_{4-16}$ cycloalkylalkyl, $C_{7-19}$ arylalkyl, and $C_{2-14}$ heteroarylalkyl groups, wherein the $C_{1-8}$ alkyl, $C_{4-16}$ cycloalkylalkyl, $C_{7-19}$ arylalkyl, and $C_{2-14}$ heteroarylalkyl groups are optionally substituted with one or more groups independently chosen from halo, $C_{1-8}$ alkyl, $C_{1-8}$ hydroxyalkyl, $C_{1-8}$ haloalkyl, $C_{1-18}$ aryl, —$OZ^3$, —C(=O)$OZ^3$, —C(=O)$NZ^3Z^4$, and —$SO_2Z^3$ groups, wherein $Z^3$ and $Z^4$, which may be identical or different, are independently chosen from H, $C_{1-8}$ alkyl, and $C_{1-8}$ haloalkyl groups, or $Z^3$ and $Z^4$ join together along with the nitrogen atom to which they are attached to form a ring.

In some embodiments, R² is chosen from H, $C_{1-8}$ alkyl, and $C_{4-16}$ cycloalkylalkyl groups. In some embodiments, R² is chosen from H, $C_{1-4}$ alkyl, and $C_{4-8}$ cycloalkylalkyl groups. In some embodiments, R² is H. In some embodiments, R² is chosen from $C_{1-8}$ alkyl groups. In some embodiments, R² is chosen from $C_{1-4}$ alkyl groups. In some embodiments, R² is chosen from methyl, ethyl, propyl, and butyl groups. In some embodiments, R² is methyl. In some embodiments, R² is chosen from $C_{4-16}$ cycloalkylalkyl groups. In some embodiments, R² is chosen from $C_{4-8}$ cycloalkylalkyl groups. In some embodiments, R² is chosen from cyclohexylmethyl and cyclopropylmethyl. In some embodiments, R² is cyclopropylmethyl.

In some embodiments, R² is chosen from $C_{7-9}$ arylalkyl and $C_{2-14}$ heteroarylalkyl groups, wherein the $C_{7-19}$ arylalkyl and $C_{2-14}$ heteroarylalkyl groups are unsubstituted. In some embodiments, R² is chosen from $C_{7-19}$ arylalkyl and $C_{2-14}$ heteroarylalkyl groups, wherein the $C_{7-19}$ arylalkyl and $C_{2-14}$ heteroarylalkyl groups are substituted with one or more groups independently chosen from halo, $C_{1-8}$ alkyl, $C_{1-8}$ hydroxyalkyl, $C_{1-8}$ haloalkyl, $C_{6-18}$ aryl, —$OZ^3$, —C(=O)$OZ^3$, and —$SO_2Z^3$ groups.

In some embodiments, R² is chosen from $C_{7-19}$ arylalkyl groups. In some embodiments, R² is chosen from $C_{7-15}$ arylalkyl groups. In some embodiments, R² is chosen from $C_{7-11}$ arylalkyl groups. In some embodiments, R² is chosen from $C_{2-14}$ heteroarylalkyl groups. In some embodiments, R² is chosen from $C_{4-14}$ heteroarylalkyl groups. In some embodiments, R² is chosen from $C_{2-10}$ heteroarylalkyl groups. In some embodiments, R² is chosen from $C_{4-10}$ heteroarylalkyl groups.

In some embodiments, R² is chosen from $C_{7-19}$ arylalkyl groups, wherein the $C_{7-19}$ arylalkyl groups are unsubstituted. In some embodiments. R² is chosen from $C_{7-11}$ arylalkyl groups, wherein the $C_{7-11}$ arylalkyl groups are unsubstituted.

In some embodiments, R² is chosen from

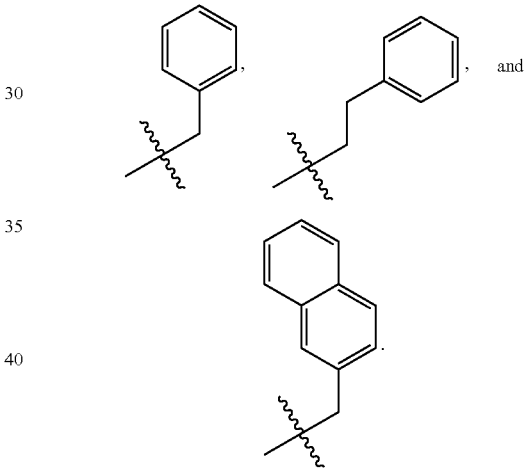

In some embodiments, R² is chosen from $C_{7-19}$ arylalkyl groups, wherein the $C_{7-19}$ arylalkyl groups are substituted with one or more groups independently chosen from halo groups. In some embodiments, the halo group is independently chosen from fluoro and chloro. In some embodiments, at least one halo group is fluoro. In some embodiments, at least one halo group is chloro.

In some embodiments, R² is chosen from

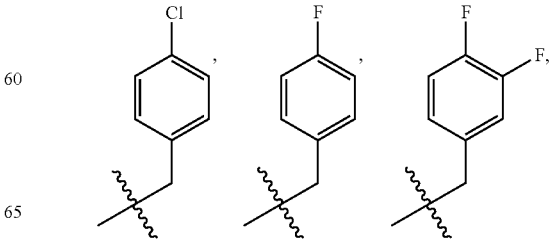

-continued

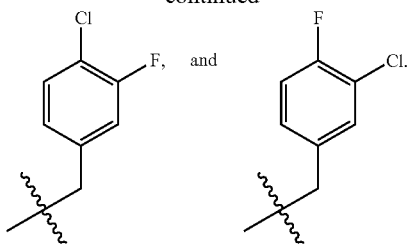

In some embodiments, $R^2$ is chosen from $C_{7-19}$ arylalkyl groups, wherein the $C_{7-19}$ arylalkyl groups are substituted with one or more groups independently chosen from $C_{1-8}$ alkyl, $C_{1-8}$ hydroxyalkyl, $C_{1-8}$ haloalkyl, and $C_{6-18}$ aryl groups. In some embodiments. $R^2$ is benzyl, wherein the benzyl is substituted with one or more groups independently chosen from $C_{1-8}$ alkyl, $C_{1-8}$ hydroxyalkyl, $C_{1-8}$ haloalkyl, and $C_{6-18}$ aryl groups.

In some embodiments, $R^2$ is chosen from

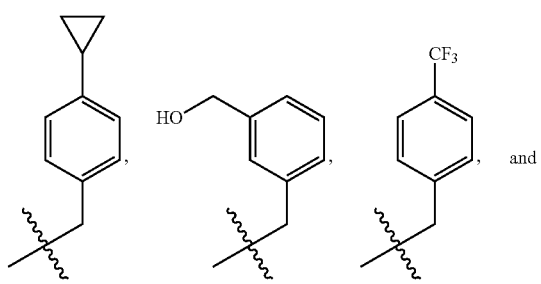

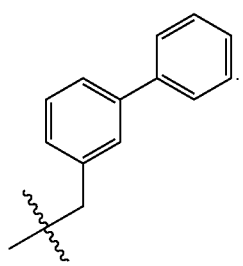

In some embodiments, $R^2$ is chosen from $C_{7-19}$ arylalkyl groups, wherein the $C_{7-19}$ arylalkyl groups are substituted with one or more groups independently chosen from —$OZ^3$, —C(=O)$OZ^3$, and —SO$_2Z^3$ groups, wherein $Z^3$ is independently chosen from H, $C_{1-8}$ alkyl, and $C_{1-8}$ haloalkyl groups. In some embodiments, $R^2$ is benzyl, wherein the benzyl is substituted with one or more groups independently chosen from —$OZ^3$, —C(=O)$OZ^3$, and —SO$_2Z^3$ groups. In some embodiments, $Z^3$ is chosen from H, $C_{1-4}$ alkyl, and $C_{1-4}$ haloalkyl groups. In some embodiments, $Z^3$ is H. In some embodiments, $Z^3$ is chosen from $C_{1-4}$ alkyl groups. In some embodiments, $Z^3$ is methyl. In some embodiments, $Z^3$ is chosen from $C_{1-4}$ haloalkyl groups. In some embodiments, $Z^3$ is —CF$_3$.

In some embodiments, $R^2$ is chosen from

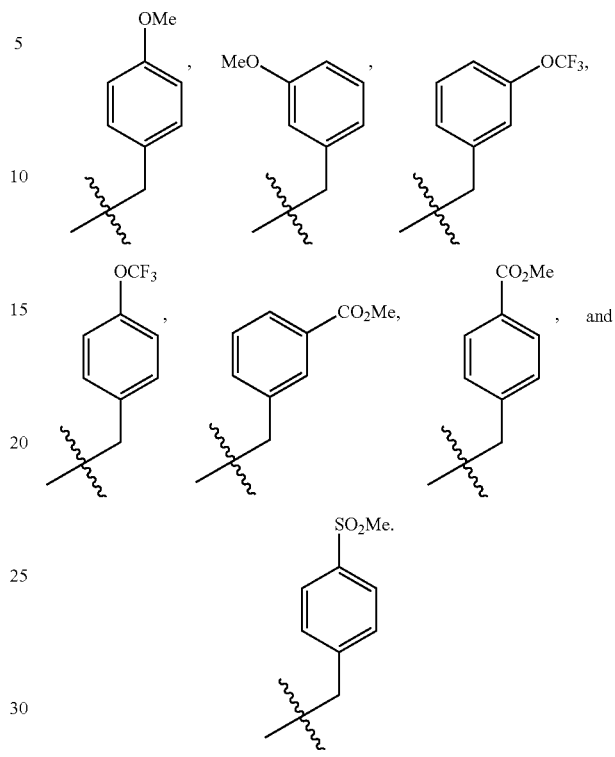

In some embodiments, $R^2$ is chosen from $C_{2-14}$ heteroarylalkyl groups, wherein the $C_{2-14}$ heteroarylalkyl groups are unsubstituted. In some embodiments, $R^2$ is chosen from $C_{2-10}$ heteroarylalkyl groups, wherein the $C_{2-10}$ heteroarylalkyl groups are unsubstituted. In some embodiments, $R^2$ is chosen from $C_{4-14}$ heteroarylalkyl groups, wherein the $C_{4-14}$ heteroarylalkyl groups are unsubstituted. In some embodiments, $R^2$ is chosen from $C_{4-10}$ heteroarylalkyl groups, wherein the $C_{4-10}$ heteroarylalkyl groups are unsubstituted.

In some embodiments, $R^2$ is chosen from $C_{2-14}$ heteroarylalkyl groups, wherein the $C_{2-14}$ heteroarylalkyl groups are optionally substituted with one or more groups independently chosen from halo, $C_{1-8}$ alkyl, $C_{1-8}$ hydroxyalkyl, $C_{1-8}$ haloalkyl, $C_{6-18}$ aryl, —$OZ^3$, —C(=O)$OZ^3$, and —SO$_2Z^3$ groups, wherein $Z^3$ is independently chosen from H and $C_{1-8}$ alkyl groups. In some embodiments, $Z^3$ is chosen from H and methyl. In some embodiments, $Z^3$ is H. In some embodiments, $Z^3$ is methyl.

In some embodiments, $R^2$ is chosen from

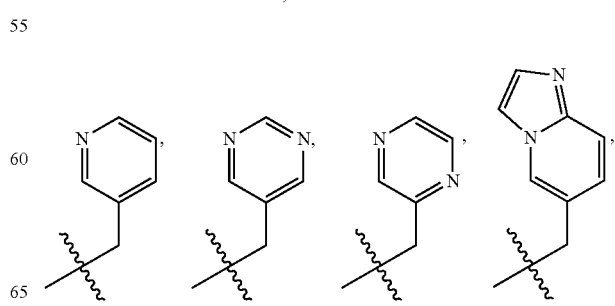

-continued

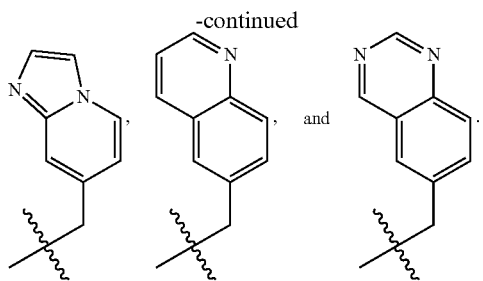

In some embodiments, $R^3$ is chosen from $C_{1-13}$ heteroaryl groups optionally substituted with one or more groups independently chosen from $R^4$, $C_{1-8}$ alkyl, $C_{1-8}$ haloalkyl, —C(=O)O$Z^5$, and —C(=O)N$Z^5Z^6$ groups. In some embodiments, $R^3$ is chosen from $C_{1-13}$ heteroaryl groups substituted with one or more groups independently chosen from $R^4$, $C_{1-8}$ alkyl, $C_{1-8}$ haloalkyl, —C(=O)O$Z^5$, and —C(=O)N$Z^5Z^6$ groups. In some embodiments, $R^3$ is chosen from $C_{2-6}$ heteroaryl groups. In some embodiments, $R^3$ is chosen from $C_{2-4}$ heteroaryl groups.

In some embodiments, $R^3$ is chosen from $C_{1-13}$ heteroaryl groups optionally substituted with one or more groups independently chosen from $R^4$. In some embodiments, $R^3$ is chosen from $C_{2-4}$ heteroaryl groups optionally substituted with one or more groups independently chosen from $R^4$. In some embodiments, $R^3$ is chosen from $C_{1-13}$ heteroaryl groups substituted with one or more groups independently chosen from $R^4$. In some embodiments, $R^3$ is chosen from $C_{2-4}$ heteroaryl groups substituted with one or more groups independently chosen from $R^4$.

In some embodiments, $R^4$ is chosen from $C_{6-18}$ aryl groups optionally substituted with one or more groups independently chosen from halo groups. In some embodiments, $R^4$ is chosen from phenyl optionally substituted with one or more groups independently chosen from halo groups. In some embodiments, $R^4$ is chosen from $C_{6-18}$ aryl groups substituted with one or more groups independently chosen from halo groups. In some embodiments, $R^4$ is chosen from phenyl substituted with one or more groups independently chosen from halo groups. In some embodiments, at least one halo group is fluoro.

In some embodiments, $R^3$ is chosen from

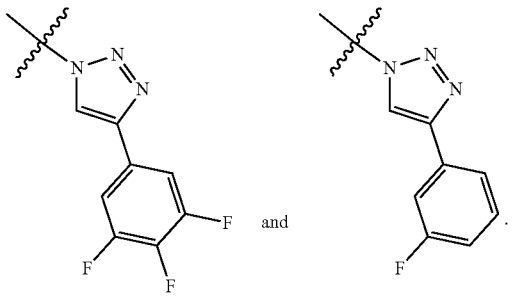 [SMILES: *n1cc(-c2cc(F)c(F)c(F)c2)nn1 ; *n1cc(-c2cccc(F)c2)nn1]

In some embodiments, $R^3$ is

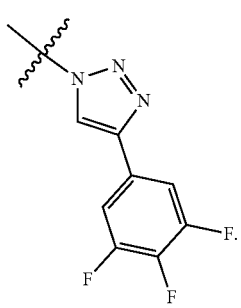 [SMILES: *n1cc(-c2cc(F)c(F)c(F)c2)nn1]

In some embodiments, $R^3$ is

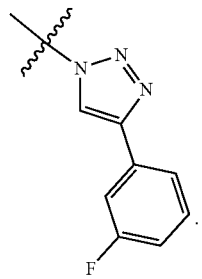 [SMILES: *n1cc(-c2cccc(F)c2)nn1]

In some embodiments, X is chosen from —C—, —O—, —S—, and —N($R^5$)—, wherein $R^5$ is chosen from H, $C_{1-8}$ alkyl, and $C_{1-8}$ haloalkyl groups. In some embodiments, X is —C—. In some embodiments, X is —O—. In some embodiments, X is —S—. In some embodiments, X is —N($R^5$)—. In some embodiments, $R^5$ is chosen from H, $C_{1-4}$ alkyl, and $C_{1-4}$ haloalkyl groups. In some embodiments, $R^5$ is H. In some embodiments, $R^5$ is chosen from $C_{1-4}$ alkyl groups.

In some embodiments, Y is H. In some embodiments, Y is chosen from halo groups. In some embodiments, Y is fluoro. In some embodiments, Y is chosen from —O$Z^9$ groups. In some embodiments, $Z^9$ is chosen from H and $C_{1-4}$ alkyl groups. In some embodiments, Y is —OH. In some embodiments, Y is —OMe.

In some embodiments, each of $Z^1$, $Z^2$, $Z^3$, $Z^4$, $Z^5$, $Z^6$, $Z^7$, $Z^8$, $Z^9$, $T^1$ and $T^2$ is unsubstituted. In some embodiments, at least one of $Z^1$, $Z^2$, $Z^3$, $Z^4$, $Z^5$, $Z^6$, $Z^7$, $Z^8$, $Z^9$, $T^1$, and $T^2$ is substituted. In some embodiments, at least one of $Z^1$, $Z^2$, $Z^3$, $Z^4$, $Z^5$, $Z^6$, $Z^7$, $Z^8$, $Z^9$, $T^1$, and $T^2$ is substituted with one or more groups independently chosen from halo and —O$R^6$ groups. In some embodiments, at least one of $Z^1$, $Z^2$, $Z^3$, $Z^4$, $Z^5$, $Z^6$, $Z^7$, $Z^8$, $Z^9$, $T^1$, and $T^2$ is substituted with one or more groups independently chosen from halo groups. In some embodiments, at least one of $Z^1$, $Z^2$, $Z^3$, $Z^4$, $Z^5$, $Z^6$, $Z^7$, $Z^8$, $Z^9$, $T^1$, and $T^2$ is substituted with one or more groups independently chosen from —O$R^6$ groups.

In some embodiments, each of $Z^1$, $Z^2$, $Z^3$, $Z^4$, $Z^5$, $Z^6$, $Z^7$, $Z^8$, and $Z^9$ is unsubstituted. In some embodiments, at least one of $Z^1$, $Z^2$, $Z^3$, $Z^4$, $Z^5$, $Z^6$, $Z^7$, $Z^8$, and $Z^9$ is substituted. In some embodiments, at least one of $Z^1$, $Z^2$, $Z^3$, $Z^4$, $Z^5$, $Z^6$, $Z^7$, $Z^8$, and $Z^9$ is substituted with one or more groups independently chosen from halo and —O$R^6$ groups. In some embodiments, at least one of $Z^1$, $Z^3$, $Z^4$, $Z^5$, $Z^6$, $Z^7$, $Z^8$, and $Z^9$ is substituted with one or more groups independently chosen from halo groups. In some embodiments, at least one of $Z^1$, $Z^2$, $Z^3$, $Z^4$, $Z^5$, $Z^6$, $Z^7$, $Z^8$, and $Z^9$ is substituted with one or more groups independently chosen from —OR$^6$ groups. In some embodiments, R$^6$ is H. In some embodiments, R$^6$ is independently chosen from C$_{1-8}$ alkyl groups. In some embodiments, R$^6$ is independently chosen from C$_{1-4}$ alkyl groups. In some embodiments, R$^6$ is independently chosen from methyl, ethyl, propyl, and butyl groups. In some embodiments, the halo group is fluoro.

Also provided are pharmaceutical compositions comprising at least one compound of Formula (I). Such pharmaceutical compositions are described in greater detail herein. These compounds and compositions may be used in the methods described herein.

In some embodiments, a method for treating and/or preventing at least one disease, disorder, and/or condition where inhibition of galectin-3 mediated functions may be useful is disclosed, the method comprising administering at least one compound of Formula (I) and/or a pharmaceutical composition comprising at least one compound of Formula (I).

In some embodiments, a method for treating and/or preventing at least one inflammatory disease, disorder, and/or condition in which the adhesion and/or migration of cells occurs in the disease, disorder, and/or condition is disclosed, the method comprising administering at least one compound of Formula (I) and/or a pharmaceutical composition comprising at least one compound of Formula (I).

In some embodiments, a method for regulating the diffusion, compartmentalization, and/or endocytosis of plasma membrane glycoproteins and/or glycolipids is disclosed, the method comprising administering at least one compound of Formula (I) and/or a pharmaceutical composition comprising at least one compound of Formula (I).

In some embodiments, a method for regulating the selection, activation, and/or arrest of T cells, receptor kinase signaling, and/or the functionality of membrane receptors is disclosed, the method comprising administering at least one compound of Formula (I) and/or a pharmaceutical composition comprising at least one compound of Formula (I).

In some embodiments, a method for treating and/or preventing at least one fibrosis is disclosed, the method comprising administering at least one compound of Formula (I) and/or a pharmaceutical composition comprising at least one compound of Formula (I). In some embodiments, the at least one compound of Formula (I) inhibits lattice formation between galectin-3 and glycosylated ligands.

In some embodiment, a method for treating and/or preventing a cancer is disclosed, the method comprising administering to a subject in need thereof an effective amount of at least one compound of Formula (I) and/or a pharmaceutical composition comprising at least one compound of Formula (I). In some embodiments, at least one compound of Formula (I) and/or pharmaceutical composition comprising at least one compound of Formula (I) may be administered in conjunction with (i.e., as an adjunct therapy, which is also called adjunctive therapy) chemotherapy and/or radiotherapy.

The chemotherapy and/or radiotherapy may be referred to as the primary anti-tumor or anti-cancer therapy that is being administered to the subject to treat the particular cancer. In some embodiments, a method for reducing (i.e., inhibiting, diminishing) chemosensitivity and/or radiosensitivity of hematopoietic stem cells (HSC) to the chemotherapeutic drug(s) and/or radiotherapy, respectively, is disclosed, the method comprising administering to a subject in need thereof an effective amount of at least one compound of Formula (I) and/or a pharmaceutical composition comprising at least one compound of Formula (I).

In some embodiments, a method for enhancing (i.e., promoting) survival of hematopoietic stem cells is provided, the method comprising administering to a subject in need thereof at least one compound of Formula (I) and/or a pharmaceutical composition comprising at least one compound of Formula (I).

In some embodiments, a method for decreasing the likelihood of occurrence of metastasis of cancer cells (also called tumor cells herein) in a subject who is in need thereof is disclosed, the method comprising administering an effective amount of at least one compound of Formula (I) and/or a pharmaceutical composition comprising at least one compound of Formula (I).

In some embodiments, a method for treatment and/or prevention of at least one cancer in which the cancer cells may leave the primary site is disclosed, the method comprising administering to a subject in need thereof an effective amount of at least one compound of Formula (I) and/or a pharmaceutical composition comprising at least one compound of Formula (I). A primary site may be, for example, solid tissue (e.g., breast or prostate) or the bloodstream.

In some embodiments, a method for treatment and/or prevention of at least one cancer in which it is desirable to mobilize cancer cells from a site into the bloodstream and/or retain the cancer cells in the bloodstream is disclosed, the method comprising administering to a subject in need thereof an effective amount of at least one compound of Formula (I) and/or a pharmaceutical composition comprising at least one compound of Formula (I).

In some embodiments, a method for decreasing the likelihood of occurrence of infiltration of cancer cells into bone marrow is disclosed, the method comprises administering to a subject in need thereof an effective amount of at least one compound of Formula (I) and/or a pharmaceutical composition comprising at least one compound of Formula (I).

In some embodiments, a method for releasing cells into circulating blood and enhancing retention of the cells in the blood is disclosed, the method comprising administering to a subject in need thereof an effective amount of at least one compound of Formula (I) and/or a pharmaceutical composition comprising at least one compound of Formula (I). In some embodiments, the method further includes collecting the released cells. In some embodiments, collecting the released cells utilizes apheresis. In some embodiments, the released cells are stem cells (e.g., bone marrow progenitor cells). In some embodiments, G-CSF is administered to the individual.

In some embodiments, a method for treating and/or preventing checkpoint inhibition of T-cells in a subject is disclosed, the method comprising administering to a subject in need thereof an effective amount of at least one compound of Formula (I) and/or a pharmaceutical composition comprising at least one compound of Formula (I).

In some embodiments, a method for treating and/or preventing thrombosis is disclosed, the method comprising administering to a subject in need thereof an effective amount of at least one compound of Formula (I) and/or a pharmaceutical composition comprising at least one compound of Formula (I).

In some embodiments, a method for treating and/or preventing one cardiovascular disease, disorder and/or condition is disclosed, the method comprising administering to a subject in need thereof an effective amount of at least one compound of Formula (I) and/or a pharmaceutical composition comprising at least one compound of Formula (I).

In some embodiments, a method for treatment and/or prevention of atherosclerosis is disclosed, the method comprising administering to a subject in need thereof an effective amount of at least one compound of Formula (I) and/or a pharmaceutical composition comprising at least one compound of Formula (I).

In some embodiments, a method for inhibiting the rejection of transplanted tissue is disclosed, the method comprising administering to a subject in need thereof an effective amount of at least one compound of Formula (I) and/or a pharmaceutical composition comprising at least one compound of Formula (I).

In some embodiments, a method for treatment and/or prevention of pathological angiogenesis is disclosed, the method comprising administering to a subject in need thereof an effective amount of at least one compound of Formula (I) and/or a pharmaceutical composition comprising at least one compound of Formula (I).

In some embodiments, a method for treatment and/or prevention of an epileptic syndrome is disclosed, the method comprising administering to a subject in need thereof at least one compound of Formula (I) and/or a pharmaceutical composition comprising at least one compound of Formula (I).

In some embodiments, a method for treatment and/or prevention of a neurodegenerative disease is disclosed, the method comprising administering to a subject in need thereof an effective amount of at least one compound of Formula (I) and/or a pharmaceutical composition comprising at least one compound of Formula (I).

In some embodiments, a method for treatment and/or prevention of α-synucleinopathies is disclosed, the method comprising administering to a subject in need thereof an effective amount of at least one compound of Formula (I) and/or a pharmaceutical composition comprising at least one compound of Formula (I).

In some embodiments, a method for treatment and prevention of a fibrosing disease or condition is disclosed, the method comprising administering to a subject in need thereof an effective amount of at least one compound of Formula (I) and/or a pharmaceutical composition comprising at least one compound of Formula (I).

In some embodiments, a method for treatment and prevention of sinusoidal obstruction syndrome (SOS) or complications associated therewith is disclosed, the method comprising administering to a subject in need thereof an effective amount of at least one compound of Formula (I) and/or a pharmaceutical composition comprising at least one compound of Formula (I).

In some embodiments, a compound of Formula (I) and/or a pharmaceutical composition comprising at least one compound of Formula (I) may be used for the preparation and/or manufacture of a medicament for use in treating and/or preventing at least one of the diseases, disorders, and/or conditions described herein.

Whenever a term in the specification is identified as a range (e.g., $C_{1-4}$ alkyl) or "ranging from", the range independently discloses and includes each element of the range. As a non-limiting example, $C_{1-4}$ alkyl groups includes, independently, $C_1$ alkyl groups, $C_2$ alkyl groups, $C_3$ alkyl groups, and $C_4$ alkyl groups. As another non-limiting example, "n is an integer ranging from 0 to 2" includes, independently, 0, 1, and 2.

The terms "at least one" and "one or more" are intended to be synonymous and to refer to no less than one but possibly more, such as one, two, three, etc. For example, the term "at least one $C_{1-4}$ alkyl group" refers to one or more $C_{1-4}$ alkyl groups, such as one $C_{1-4}$ alkyl group, two $C_{1-4}$ alkyl groups, etc.

The term "alkyl" includes saturated straight, branched, and cyclic (also identified as cycloalkyl), primary, secondary, and tertiary hydrocarbon groups. Non-limiting examples of alkyl groups include methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless stated otherwise specifically in the specification, an alkyl group may be optionally substituted.

The term "alkenyl" includes straight, branched, and cyclic hydrocarbon groups comprising at least one double bond. The double bond of an alkenyl group can be unconjugated or conjugated with another unsaturated group. Non-limiting examples of alkenyl groups include vinyl, allyl, butenyl, pentenyl, hexenyl, butadienyl, pentadienyl, hexadienyl, 2-ethylhexenyl, and cyclopent-1-en-1-yl. Unless stated otherwise specifically in the specification, an alkenyl group may be optionally substituted.

The term "alkynyl" includes straight and branched hydrocarbon groups comprising at least one triple bond. The triple bond of an alkynyl group can be unconjugated or conjugated with another unsaturated group. Non-limiting examples of alkynyl groups include ethynyl, propynyl, butynyl, pentynyl, and hexynyl. Unless stated otherwise specifically in the specification, an alkynyl group may be optionally substituted.

The term "aryl" includes hydrocarbon ring system groups comprising at least 6 carbon atoms and at least one aromatic ring. The aryl group may be a monocyclic, bicyclic, tricyclic or tetracyclic ring system, which may include fused or bridged ring systems. Non-limiting examples of aryl groups include aryl groups derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group may be optionally substituted.

The terms "galectin-3 antagonist," "galectin-3 inhibitor," and "inhibitors of galectin-3" are used interchangeably herein, and include inhibitors of galectin-3 only, as well as inhibitors of galectin-3 and one or more other galectin, such as galectin-1, galectin-2, galectin-4, galectin-5, galectin-6, galectin-7, galectin-8, galectin-9, galectin-10, galectin-11, and galectin-12.

The term "glycomimetic" includes any naturally occurring or non-naturally occurring carbohydrate compound in which at least one substituent has been replaced, or at least one ring has been modified (e.g., substitution of carbon for a ring oxygen), to yield a compound that is not fully carbohydrate.

The term "halo" or "halogen" includes fluoro, chloro, bromo, and iodo.

The term "haloalkyl" includes alkyl groups, as defined herein, substituted by at least one halogen, as defined herein. Non-limiting examples of haloalkyl groups include trifluoromethyl, difluoromethyl, trichloromethyl, 2,2,2-trifluoroethyl, 1,2-difluoroethyl, 3-bromo-2-fluoropropyl, and 1,2-dibromoethyl. A "fluoroalkyl" is a haloalkyl wherein at least one halogen is fluoro. Unless stated otherwise specifically in the specification, a haloalkyl group may be optionally substituted.

The term "haloalkenyl" includes alkenyl groups, as defined herein, substituted by at least one halogen, as defined herein. Non-limiting examples of haloalkenyl groups include fluoroethenyl, 1,2-difluoroethenyl, 3-bromo- 2-fluoropropenyl, and 1,2-dibromnoethenyl. A "fluoroalkenyl" is a haloalkenyl substituted with at least one fluoro group. Unless stated otherwise specifically in the specification, a haloalkenyl group may be optionally substituted.

The term "haloalkynyl" includes alkynyl groups, as defined herein, substituted by at least one halogen, as defined herein. Non-limiting examples include fluoroethynyl, 1,2-difluoroethynyl, 3-bromo-2-fluoropropynyl, and 1,2-dibromoethynyl. A "fluoroalkynyl" is a haloalkynyl wherein at least one halogen is fluoro. Unless stated otherwise specifically in the specification, a haloalkynyl group may be optionally substituted.

The term "heteroaryl" includes 5- to 14-membered ring groups comprising 1 to 13 ring carbon atoms and 1 to 6 ring heteroatom(s) each independently chosen from N, O, and S, and at least one aromatic ring. Unless stated otherwise specifically in the specification, the heteroaryl group may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Non-limiting examples include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofurranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

Unless stated otherwise specifically in the specification, substituents may be optionally substituted.

The term "pharmaceutically acceptable salts" includes both acid and base addition salts. Non-limiting examples of pharmaceutically acceptable acid addition salts include chlorides, bromides, sulfates, nitrates, phosphates, sulfonates, methane sulfonates, formates, tartrates, maleates, citrates, benzoates, salicylates, and ascorbates. Non-limiting examples of pharmaceutically acceptable base addition salts include sodium, potassium, lithium, ammonium (substituted and unsubstituted), calcium, magnesium, iron, zinc, copper, manganese, and aluminum salts. Pharmaceutically acceptable salts may, for example, be obtained using standard procedures well known in the field of pharmaceuticals.

The term "prodrug" includes compounds that may be converted, for example, under physiological conditions or by solvolysis, to a biologically active compound described herein. Thus, the term "prodrug" includes metabolic precursors of compounds described herein that are pharmaceutically acceptable. A discussion of prodrugs can be found, for example, in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987. The term "prodrug" also includes covalently bonded carriers that release the active compound(s) as described herein in vivo when such prodrug is administered to a subject. Non-limiting examples of prodrugs include ester and amide derivatives of hydroxy, carboxy, mercapto and amino functional groups in the compounds described herein.

The term "substituted" includes the situation where, in any of the above groups, at least one hydrogen atom is replaced by a non-hydrogen atom such as, for example, a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also includes the situation where, in any of the above groups, at least one hydrogen atom is replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles.

The present disclosure includes within its scope all the possible geometric isomers, e.g., Z and E isomers (cis and trans isomers), of the compounds as well as all the possible optical isomers, e.g., diastereomers and enantiomers, of the compounds. Furthermore, the present disclosure includes in its scope both the individual isomers and any mixtures thereof, e.g., racemic mixtures. The individual isomers may be obtained using the corresponding isomeric forms of the starting material or they may be separated after the preparation of the end compound according to conventional separation methods. For the separation of optical isomers, e.g., enantiomers, from the mixture thereof conventional resolution methods, e.g., fractional crystallization, may be used.

The present disclosure includes within its scope all possible tautomers. Furthermore, the present disclosure includes in its scope both the individual tautomers and any mixtures thereof.

Compounds of Formula (I) may be prepared as shown in FIGS. 1 through 5. It is understood that one of ordinary skill in the art may be able to make these compounds by similar methods or by combining other methods known to one of ordinary skill in the art. It is also understood that one of ordinary skill in the art would be able to make other compounds of Formula (I) not specifically illustrated herein by using appropriate starting components and modifying the parameters of the synthesis as needed. In general, starting components may be obtained from sources such as Sigma Aldrich, Alfa Aesar, Maybridge, Matrix Scientific, TCI, and Fluorochem USA, etc. and/or synthesized according to sources known to those of ordinary skill in the art (see, for example, Advanced Organic Chemistry: Reactions, Mechanisms, and Structure, 5th edition (Wiley, December 2000)) and/or prepared as described herein.

It will also be appreciated by those skilled in the art that in the processes described herein the functional groups of intermediate compounds may need to be protected by suitable protecting groups, even if not specifically described. Such functional groups include hydroxy, amino, mercapto, and carboxylic acid. Suitable protecting groups for hydroxy include but are not limited to trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include but are not limited to t-butoxycarbonyl, benzyloxycarbonyl, and the like. Suitable protecting groups for mercapto include but are not limited to —C(O)R" (where R" is alkyl, aryl or arylalkyl), p-methoxybenzyl, trityl and the like. Suitable protecting groups for carboxylic acid include but are not limited to alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Analogous reactants to those described herein may be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002.

Methods known to one of ordinary skill in the art may be identified through various reference books, articles, and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Biological activity of a compound described herein may be determined, for example, by performing at least one in vitro and/or in vivo study routinely practiced in the art and described herein or in the art. In vitro assays include without limitation binding assays, immunoassays, competitive binding assays, and cell-based activity assays.

An inhibition assay may be used to screen for antagonists of galectin-3. For example, an assay may be performed to characterize the capability of a compound described herein to inhibit interaction of galectin-3 with a Galβ1-3GlcNAc carbohydrate structure. The inhibition assay may be a competitive binding assay, which allows the determination of $IC_{50}$ values. By way of example, a Galβ1-3GlcNAc polymer may be immobilized onto a matrix; a composition may be added to reduce nonspecific binding; the immobilized Galβ1-3GlcNAc polymer may be contacted with the candidate compound in the presence of galectin-3 group under conditions and for a time sufficient to permit galectin-3 to bind to the immobilized Galβ1-3GlcNAc polymer; the immobilized Galβ1-3GlcNAc polymer may be washed; and the amount of galectin-3 bound to the immobilized Galβ1-3GlcNAc polymer may be detected. Variations of such steps can be readily and routinely accomplished by a person of ordinary skill in the art.

Conditions for a particular assay include temperature, buffers (including salts, cations, media), and other components that maintain the integrity of any cell used in the assay and the compound, which a person of ordinary skill in the art will be familiar and/or which can be readily determined. A person of ordinary skill in the art also readily appreciates that appropriate controls can be designed and included when performing the in vitro methods and in vivo methods described herein.

The source of a compound that is characterized by at least one assay and techniques described herein and in the art may be a biological sample that is obtained from a subject who has been treated with the compound. The cells that may be used in the assay may also be provided in a biological sample. A "biological sample" may include a sample from a subject, and may be a blood sample (from which serum or plasma may be prepared), a biopsy specimen, one or more body fluids (e.g., lung lavage, ascites, mucosal washings, synovial fluid, urine), bone marrow, lymph nodes, tissue explant, organ culture, or any other tissue or cell preparation from the subject or a biological source. A biological sample may further include a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. In some embodiments, the subject or biological source may be a human or non-human animal, a primary cell culture (e.g., immune cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

As described herein, methods for characterizing galectin-3 antagonists include animal model studies. Non-limiting examples of animal models for liquid cancers used in the art include multiple myeloma (see, e.g., DeWeerdt, Nature 480:S38-S39 (15 Dec. 2011) doi:10.1038/480S38a; Published online 14 Dec. 2011; Mitsiades et al., Clin. Cancer Res. 2009 15:1210021 (2009)); acute myeloid leukemia (AML) (Zuber et al, Genes Dev. 2009 Apr. 1; 23(7): 877-889). Animal models for acute lymphoblastic leukemia (ALL) have been used by persons of ordinary skill in the art for more than two decades. Numerous exemplary animal models for solid tumor cancers are routinely used and are well known to persons of ordinary skill in the art.

The compounds of the present disclosure and the pharmaceutical compositions comprising at least one of such compounds may be useful in methods for treating and/or preventing a disease or disorder that is treatable by inhibiting at least one activity of galectin-3 (and/or inhibiting binding of galectin-3 to ligand(s), which in turn inhibits a biological activity).

The compounds of the present disclosure and pharmaceutical compositions comprising at least one such compound may be useful in methods for treating and/or preventing at least one inflammatory disease. Inflammation comprises reaction of vascularized living tissue to injury. By way of example, although galectin-3 mediated cell adhesion may be important to the body's anti-infective immune response, in other circumstances, galectin-3 mediated cell adhesion may be undesirable or excessive, resulting in tissue damage and/or scarring instead of repair. For example, many pathologies (such as autoimmune and inflammatory diseases, shock and reperfusion injuries) involve abnormal adhesion of white blood cells. Therefore, inflammation affects blood vessels and adjacent tissues in response to an injury or abnormal stimulation by a physical, chemical, or biological agent. Examples of inflammatory diseases, disorders, or conditions include, without limitation, dermatitis, chronic eczema, psoriasis, multiple sclerosis, rheumatoid arthritis, systemic lupus erythematosus, graft versus host disease, sepsis, diabetes, atherosclerosis, Sjogren's syndrome, progressive systemic sclerosis, scleroderma, acute coronary syndrome, ischemic reperfusion, Crohn's disease, inflammatory bowel disease, endometriosis, glomerulonephritis, myasthenia gravis, idiopathic pulmonary fibrosis, asthma, allergic reaction, acute respiratory distress syndrome (ARDS) or other acute leukocyte-mediated lung injury, vasculitis, or inflammatory autoimmune myositis. Other diseases and disorders for which the compounds described herein may be useful for treating and/or preventing include hyperactive coronary circulation, microbial infection, cancer metastasis, thrombosis, wounds, burns, spinal cord damage, digestive tract mucous membrane disorders (e.g., gastritis, ulcers), osteoporosis, osteoarthritis, septic shock, traumatic shock, stroke, nephritis, atopic dermatitis, frostbite injury, adult dyspnoea syndrome, ulcerative colitis, diabetes and reperfusion injury following ischemic episodes, prevention of restenosis associated with vascular stenting, and for undesirable angiogenesis, for example, angiogenesis associated with tumor growth.

As discussed in detail herein, a disease or disorder to be treated or prevented is a cancer and related metastasis and includes cancers that comprise solid tumor(s) and cancers that comprise liquid tumor(s). The compounds of the present disclosure and pharmaceutical compositions comprising at least one such compound may be useful in methods for preventing and/or treating cancer. In some embodiments, the at least one compound may be used for treating and/or preventing metastasis and/or for inhibiting (slowing, retarding, or preventing) metastasis of cancer cells.

In some embodiments, at least one compound of Formula (I) and/or a pharmaceutical composition comprising at least one compound of Formula (I) is administered to a cancer patient in remission. In some embodiments, the at least one compound of Formula (I) and/or a pharmaceutical composition comprising at least one compound of Formula (I) is administered as a cancer vaccine to stimulate marrow infiltrating lymphocytes ("MILs") in a cancer patient or cancer survivor to prevent relapse.

In some embodiments, a method of treating cancer and/or preventing a cancer relapse is disclosed, wherein the method comprises administering to a patient in need thereof an effective amount of at least one compound of Formula (I) and/or a pharmaceutical composition comprising at least one compound of Formula (I), wherein the amount of compound of Formula (I) administered is sufficient to mobilize MILs of the patient into the peripheral blood.

In some embodiments, a method of treating cancer and/or preventing a cancer relapse is provided comprising administering to a donor patient at least one compound of Formula (I) and/or a pharmaceutical composition comprising at least one compound of Formula (I) in an amount of sufficient to mobilize MILs of the patient out of the marrow (e.g., into the peripheral blood), recovering MILS (e.g., recovering them from the peripheral blood), and transplanting at least a portion of the MIL cell population to the donor patient or another patient. In some embodiments, the MIL, cell population is expanded ex vivo before transplantation.

In some embodiments, a method of preventing cancer is provided comprising administering to a donor patient at least one compound of Formula (I) and/or a pharmaceutical composition comprising at least one compound of Formula (I) in an amount sufficient to mobilize MILs of the patient out of the bone marrow (e.g., into the peripheral blood), recovering MILs (e.g., recovering them from the peripheral blood), and transplanting at least a portion of MIL cell population to a subject (e.g., a non-cancer patient, a patient suffering from a different form or type of cancer than the donor patient, etc.). In some embodiments, the MIL cell population is expanded ex vivo before transplantation.

In some embodiments, the compounds of present disclosure and pharmaceutical compositions comprising at least one such compound may be used for decreasing (i.e., reducing) the likelihood of occurrence of metastasis of cancer cells in an individual (i.e., subject, patient) who is in need thereof. The compounds of the present disclosure and compositions comprising at least one such compound may be used for decreasing (i.e., reducing) the likelihood of occurrence of infiltration of cancer cells into bone marrow in an individual who is in need thereof. The individuals (or subjects) in need of such treatments include subjects who have been diagnosed with a cancer, which includes cancers that comprise solid tumor(s) and cancers that comprise liquid tumor(s).

Non-limiting examples of cancers include colorectal cancers, liver cancers, gastric cancers, lung cancers, brain cancers, kidney cancers, bladder cancers, thyroid cancers, prostate cancers, ovarian cancers, cervical cancers, uterine cancers, endometrial cancers, melanomas, breast cancers, and pancreatic cancers. Liquid tumors can occur in the blood, bone marrow, the soft, sponge-like tissue in the center of most bones, and lymph nodes and include leukemias (e.g., AML, ALL, CLL, and CML), lymphomas, and myelomas (e.g., multiple myeloma). Lymphomas include Hodgkin lymphoma, which is marked by the presence of a type of cell called the Reed-Sternberg cell, and non-Hodgkin lymphomas, which includes a large, diverse group of cancers of immune system cells. Non-Hodgkin lymphomas can be further divided into cancers that have an indolent (slow-growing) course and those that have an aggressive (fast-growing) course, and which subtypes respond to treatment differently.

The compounds of the present disclosure and pharmaceutical compositions comprising at least one such compound may be administered as an adjunct therapy to chemotherapy and/or radiotherapy, which is/are being delivered to the subject as primary therapy for treating the cancer. The chemotherapy and/or radiotherapy that may be administered depend upon several factors including the type of cancer, location of the tumor(s), stage of the cancer, age and gender and general health status of the subject. A person of ordinary skill in the medical art can readily determine the appropriate chemotherapy regimen and/or radiotherapy regimen for the subject in need. The person of ordinary skill in the medical art can also determine, with the aid of preclinical and clinical studies, when the compound of the present disclosure or pharmaceutical composition comprising at least one such compound should be administered to the subject, that is whether the compound or composition is administered prior to, concurrent with, or subsequent to a cycle of the primary chemotherapy or radiation treatment.

In some embodiments, a method for inhibiting activation of hepatic and/or pancreatic stellate cells is disclosed, the method comprising administering at least one compound of Formula (I) and/or a pharmaceutical composition comprising at least one compound of Formula (I).

In some embodiments, a method for inhibiting adhesion of metastasized tumor cells is disclosed, the method comprising administering at least one compound of Formula (I) and/or a pharmaceutical composition comprising at least one compound of Formula (I).

In some embodiments, a method for inhibiting cell-cell interactions and/or interactions between cells and the extracellular matrix where the cell-cell interactions and cell-matrix are induced by galectin-3 molecules bound carbohydrates found on the surface of cells is disclosed, the method comprising administering at least one compound of Formula (I) and/or a pharmaceutical composition comprising at least one compound of Formula (I). In some embodiments, the cells are tumor cells and cell-cell interactions and/or cell-matrix are responsible for the development of at least one tumor disease.

In some embodiments, a method for reducing the rate of growth of tumor cells which express galectin-3 is disclosed, the method comprising administering at least one compound of Formula (I) and/or a pharmaceutical composition comprising at least one compound of Formula (I). In some embodiments, the level of at least one G1/S cyclin in the tumor cell is reduced.

As described herein, at least one of the compounds of the present disclosure or pharmaceutical compositions comprising at least one such compound may be administered in combination with at least one additional anti-cancer agent. Chemotherapy may comprise one or more chemotherapeutic agents. For example, chemotherapy agents, radiotherapeutic agents, inhibitors of phosphoinositide-3 kinase (PI3K), and inhibitors of VEGF may be used in combination with a compound of Formula (I) described herein. Non-limiting examples of inhibitors of PI3K include the compound named by Exelixis as "XL499." Non-limiting examples of VEGF inhibitors include the compound called "cabo" (previously known as XL184). Many other chemotherapeutics are small organic molecules. As understood by a person of ordinary skill in the art, chemotherapy may also refer to a combination of two or more chemotherapeutic molecules that are administered coordinately and which may be referred to as combination chemotherapy. Numerous chemotherapeutic drugs are used in the oncology art and include, for example, alkylating agents; antimetabolites; anthracyclines, plant alkaloids; and topoisomerase inhibitors.

The compounds of the present disclosure or pharmaceutical compositions comprising at least one such compound may function independently from the anti-cancer agent or may function in coordination with the anti-cancer agent, e.g., by enhancing effectiveness of the anti-cancer agent or vice versa. Accordingly, provided herein are methods for enhancing (i.e., enhancing, promoting, improving the likelihood of, enhancing in a statistically or biologically significant manner) and/or maintaining survival of hematopoietic stem cells (HSC) in a subject who is treated with and/or will be treated with a chemotherapeutic drug(s) and/or radioactive therapy, respectively, comprising administering at least one compound of Formula (I) as described herein. In some embodiments, the subject receives and/or will receive both chemotherapy and radiation therapy. Also, provided herein is a method for reducing (i.e., reducing, inhibiting, diminishing in a statistically or biologically significant manner) chemosensitivity and/or radiosensitivity of hematopoietic stem cells (HSC) to the chemotherapeutic drug(s) and/or radioactive therapy, respectively, in a subject. Because repeated cycles of chemotherapy and radiotherapy often diminish the ability of HSCs to recover and replenish bone marrow, the glycomimetic compounds described herein may be useful for subjects who will receive more than one cycle, such as at least two, three, four or more cycles, of chemotherapy and/or radiotherapy. HSCs reside in the bone marrow and generate the cells that are needed to replenish the immune system and the blood. Anatomically, bone marrow comprises a vascular niche that is adjacent to bone endothelial sinuses (see, e.g., Kiel et al., *Cell* 121:1109-21 (2005); Sugiyama et al., *Immunity* 25:977-88 (2006); Mendez-Ferrer et al., *Nature* 466:829-34 (2010); Butler et al., *Cell Stem Cell* 6:251-64 (2010)). Additionally, galectin-3 has recently been reported to interfere with hematopoiesis and promote terminal differentiation of myeloid progenitors (see, e.g., Brand et al., *Cell Tissue Res* 346:427-37 (2011)).

In addition, the administration of at least one compound of the present disclosure or pharmaceutical composition comprising at least one such compounds may be in conjunction with one or more other therapies, e.g., for reducing toxicities of therapy. For example, at least one palliative agent to counteract (at least in part) a side effect of a therapy (e.g., anti-cancer therapy) may be administered. Agents (chemical or biological) that promote recovery, or counteract side effects of administration of antibiotics or corticosteroids, are examples of such palliative agents. At least one compound described herein may be administered before, after, or concurrently with administration of at least one additional anti-cancer agent or at least one palliative agent to reduce a side effect of therapy. When administration is concurrent, the combination may be administered from a single container or two (or more) separate containers.

Cancer cells (also called herein tumor cells) that may be prevented (i.e., inhibited, slowed) from metastasizing, from adhering to an endothelial cell, or from infiltrating bone marrow include cells of solid tumors and liquid tumors (including hematological malignancies). Examples of solid tumors are described herein and include colorectal cancer, liver cancer, gastric cancer, lung cancer, brain cancer, kidney cancer, bladder cancer, thyroid cancer, prostate cancer, ovarian cancer, cervical cancer, uterine cancer, endometrial cancer, melanoma, breast cancer, and pancreatic cancer. Liquid tumors occur in the blood, bone marrow, and lymph nodes and include leukemia (e.g., AML, ALL, CLL, and CML), lymphoma (e.g., Hodgkin lymphoma and non-Hodgkin lymphoma), and myeloma (e.g., multiple myeloma). As used herein, the term cancer cells include mature, progenitor, and cancer stem cells.

Bones are a common location for cancer to infiltrate once leaving the primary tumor location. Once cancer resides in bone, it is frequently a cause of pain to the individual. In addition, if the particular bone affected is a source for production of blood cells in the bone marrow, the individual may develop a variety of blood cell related disorders. Breast and prostate cancer are examples of solid tumors that migrate to bones. Acute myelogenous leukemia (AML) and multiple myeloma (MM) are examples of liquid tumors that migrate to bones. Cancer cells that migrate to bone will typically migrate to the endosteal region of the bone marrow. Once cancer cells have infiltrated into the marrow, the cells become quiescent and are protected from chemotherapy. The compounds of the present disclosure may block infiltration of disseminated cancer cells into bone marrow. A variety of subjects may benefit from treatment with the compounds. Examples of such subjects include individuals with a cancer type having a propensity to migrate to bone where the tumor is still localized or the tumor is disseminated but not yet infiltrated bone, or where individuals with such a cancer type are in remission.

The cancer patient population most likely to respond to treatment using antagonists of galectin-3 (e.g., compounds of Formula (I)) described herein can be identified based on the mechanisms of action of galectin-3. For example, patients may be identified for treatment based on levels of galectin-3 detected in serum or plasma by a diagnostic assay such as the Abbott Laboratories ARCHITECT Galectin-3 assay, which can be used for determining galectin-3 in serum or plasma to stratify heart failure patients for proper treatment.

The compounds of the present disclosure and pharmaceutical compositions comprising at least one such compound may be useful in methods for mobilizing cells from the bone marrow to the peripheral vasculature and tissues. As discussed herein, in some embodiments, the compounds and compositions are useful for mobilizing hematopoietic cells, including hematopoietic stem cells and hematopoietic progenitor cells. In some embodiments, the compounds act as mobilizing agents of normal blood cell types. In some embodiments, the agents are used in methods for mobilizing mature white blood cells (which may also be called leukocytes herein), such as granulocytes (e.g., neutrophils, eosinophils, basophils), lymphocytes, and monocytes from the bone marrow or other immune cell compartments such as the spleen and liver. Methods are also provided for using the compounds of the present disclosure and pharmaceutical compositions comprising at least one such compound in methods for mobilizing tumor cells from the bone marrow. The tumor cells may be malignant cells (e.g., tumor cells that are metastatic cancer cells, or highly invasive tumor cells) in cancers. These tumor cells may be of hematopoietic origin or may be malignant cells of another origin residing in the bone.

In some embodiments, the methods using the compounds described herein are useful for mobilizing hematopoietic cells, such as hematopoietic stem cells and progenitor cells and leukocytes (including granulocytes such as neutrophils), which are collected (i.e., harvested, obtained) from the subject receiving a compound of Formula (I) and at a later time are administered back into the same subject (autologous donor) or administered to a different subject (allogeneic donor). Hematopoietic stem cell replacement and hematopoietic stem cell transplantation have been successfully used for treating a number of diseases (including cancers) as described herein and in the art. By way of example, stem cell replacement therapy or transplantation follows myeloablation of a subject, such as occurs with administration of high dose chemotherapy and/or radiotherapy. Desirably, an allogeneic donor shares sufficient HLA antigens with the recipient/subject to minimize the risk of host versus graft disease in the recipient (i.e., the subject receiving the hematopoietic stem cell transplant). Obtaining the hematopoietic cells from the donor subject (autologous or allogeneic) is performed by apheresis or leukapheresis. HLA typing of a potential donor and the recipient and apheresis or leukapheresis are methods routinely practiced in the clinical art.

By way of non-limiting example, autologous or allogenic hematopoietic stem cells and progenitors cells may be used for treating a recipient subject who has certain cancers, such as Hodgkin lymphoma, non-Hodgkin lymphoma, or multiple myeloma. Allogeneic hematopoietic stem cells and progenitors cells may be used, for example, for treating a recipient subject who has acute leukemia (e.g., AML, ALL); chronic lymphocytic leukemia (CLL); amegakaryocytosis/congenital thrombocytopenia; aplastic anemia/refractory anemia; familial erythrophagocytic lymphohistiocytosis; myelodysplastic syndrome/other myelodysplastic disorders; osteopetrosis; paroxysmal nocturnal hemoglobinuria; and Wiskott-Aldrich syndrome, for example. Exemplary uses for autologous hematopoietic stem cells and progenitors cells include treating a recipient subject who has amyloidosis; germ cell tumors (e.g., testicular cancer); or a solid tumor. Allogeneic hematopoietic stem cell transplants have also been investigated for use in treating solid tumors (see, e.g., Ueno et al., *Blood* 102:3829-36 (2003)).

In some embodiments of the methods described herein, the subject is not a donor of peripheral hematopoietic cells but has a disease, disorder, or condition for which mobilization of hematopoietic cells in the subject will provide clinical benefit. Stated another way, while this clinical situation is similar to autologous hematopoietic cell replacement, the mobilized hematopoietic cells are not removed and given back to the same subject at a later time as occurs, for example, with a subject who receives myeloablation therapy. Accordingly, methods are provided for mobilizing hematopoietic cells, such as hematopoietic stem cells and progenitor cells and leukocytes (including granulocytes, such as neutrophils), by administering at least once compound of Formula (I). Mobilizing hematopoietic stem cells and progenitor cells may be useful for treating an inflammatory condition or for tissue repair or wound healing. See, e.g., Mimeault et al., *Clin. Pharmacol. Therapeutics* 82:252-64 (2007).

In some embodiments, the methods described herein are useful for mobilizing hematopoietic leukocytes (white blood cells) in a subject, which methods may be used in treating diseases, disorders, and conditions for which an increase in white blood cells, such as neutrophils, eosinophils, lymphocytes, monocytes, basophils, will provide clinical benefit.

For example, for cancer patients, the compounds of Formula (I) are beneficial for stimulating neutrophil production to compensate for hematopoietic deficits resulting from chemotherapy or radiation therapy. Other diseases, disorders, and conditions to be treated include infectious diseases and related conditions, such as sepsis. When the subject to whom at least one compound of Formula (I) is administered is a donor, neutrophils may be collected for administration to a recipient subject who has reduced hematopoietic function, reduced immune function, reduced neutrophil count, reduced neutrophil mobilization, severe chronic neutropenia, leucopenia, thrombocytopenia, anemia, and acquired immune deficiency syndrome. Mobilization of mature white blood cells may be useful in subjects to improve or to enhance tissue repair, and to minimize or prevent vascular injury and tissue damage, for example following liver transplantation, myocardial infarction or limb ischemia. See, e.g., Pelus, *Curr. Opin. Hematol.* 15:285-92 (2008); Lemoli et al., *Haematologica* 93:321-24 (2008).

The compounds of Formula (I) may be used in combination with one or more other agents that mobilize hematopoietic cells. Such agents include, for example, G-CSF; AMD3100 or other CXCR4 antagonists; GRO-β (CXCL2) and an N-terminal 4-amino truncated form (SB-251353); IL-8SDF-1α peptide analogs, CTCE-0021 and CTCE-0214; and the SDF1 analog, Met-SDF-1β (see, e.g., Pelus, supra and references cited therein). In some embodiments, a compound of Formula (I) may be administered with other mobilizing agents used in the art, which may permit administration of a lower dose of GCSF or AMD3100, for example, than required in the absence of a compound of Formula (I). The appropriate therapeutic regimen for administering a compound of Formula (I) in combination with another mobilizing agent or agents can be readily determined by a person skilled in the clinical art.

In some embodiments, the method further comprises administering a therapeutically effective amount of at least one MMP inhibitor, inflammatory cytokine inhibitor, mast cell inhibitor, NSAID, NO inhibitor, or antimicrobial compound.

In some embodiments, the method further comprises administering a therapeutically effective amount of velafermin and/or palifermin.

In some embodiments, the method further comprises administering a therapeutically effective amount of Davanat®, mannose, and/or galactose.

The compounds of the present disclosure and pharmaceutical compositions comprising at least one such compound may be useful in methods for treating and/or preventing thrombosis. As described herein methods are provided for inhibiting formation of a thrombus or inhibiting the rate at which a thrombus is formed. These methods may therefore be used for preventing thrombosis (i.e., reducing or decreasing the likelihood of occurrence of a thrombus in a statistically or clinically significant manner).

Thrombus formation may occur in infants, children, teenagers and adults. An individual may have a hereditary predisposition to thrombosis. Thrombosis may be initiated, for example, due to a medical condition (such as cancer or pregnancy), a medical procedure (such as surgery) or an environmental condition (such as prolonged immobility). Other individuals at risk for thrombus formation include those who have previously presented with a thrombus.

The compounds of the present disclosure and pharmaceutical compositions comprising at least one such compound may be useful in methods for treating individuals undergoing thrombosis or who are at risk of a thrombotic event occurring. Such individuals may or may not have a risk of bleeding. In some embodiments, the individual has a risk of bleeding. In some embodiments, the thrombosis is a venous thromboembolism (VTE). VTE causes deep vein thrombosis and pulmonary embolism. Low molecular weight (LMW) heparin is the current mainstay therapy for the prevention and treatment of VTE. In many circumstances, however, the use of LMW heparin is contraindicated. LMW heparin is a known anti-coagulant and delays clotting over four times longer than control bleeding times. Patients undergoing surgery, patients with thrombocytopenia, patients with a history of stroke, and many cancer patients should avoid administration of heparin due to the risk of bleeding. By contrast, administration of the compounds of Formula (I) significantly reduces the time to clotting than occurs when LMW heparin is administered, and thus provide a significant improvement in reducing bleeding time compared with LMW heparin. Accordingly, the compounds and pharmaceutical compositions described herein may not only be useful for treating a patient for whom the risk of bleeding is not significant, but also may be useful in when the risk of bleeding is significant and the use of anti-thrombosis agents with anti-coagulant properties (such as LMW heparin) is contraindicated.

The compounds of the present disclosure and pharmaceutical compositions comprising at least one such compound may be administered in combination with at least one additional anti-thrombosis agent. The compounds of the present disclosure and pharmaceutical compositions comprising at least one such compound may function independently from the anti-thrombosis agent or may function in coordination with the at least one anti-thrombosis agent. In addition, the administration of one or more of the compounds or compositions may be in conjunction with one or more other therapies, e.g., for reducing toxicities of therapy. For example, at least one palliative agent to counteract (at least in part) a side effect of therapy may be administered. Agents (chemical or biological) that promote recovery and/or counteract side effects of administration of antibiotics or corticosteroids are examples of such palliative agents. The compounds of the present disclosure and pharmaceutical composition comprising at least one such compound may be administered before, after, or concurrently with administration of at least one additional anti-thrombosis agent or at least one palliative agent to reduce a side effect of therapy. Where administration is concurrent, the combination may be administered from a single container or two (or more) separate containers.

The compounds of the present disclosure and pharmaceutical compositions comprising at least one such compound may be useful for treating and/or preventing at least one cardiovascular disease, disorder and/or condition. Non-limiting examples of cardiovascular disease include atherosclerosis, myocardial infarction, myocardial ischemia, coronary artery stenosis (occlusion of the coronary arteries), chronic cardiovascular and/or arterial inflammation, acute cardiovascular and/or arterial inflammation, hypercholesterolemia, restenosis (narrowing of the vessel lumen), arrhythmia, thrombosis, hyperlipidemia, hypertension, dyslipoproteinemia, angina (cardiac chest pain), and vascular complications due to a cardiovascular disease (e.g., myocardial infarction or myocardial ischemia).

In some embodiments, at least one compound of Formula (I) and/or a pharmaceutical composition comprising at least one compound of Formula (I) may be administered prior to or subsequent to an acute cardiovascular event in the subject. In some embodiments, at least one compound of Formula (I)

and/or a pharmaceutical composition comprising at least one compound of Formula (I) may be administered prior to or subsequent to the development or diagnosis of a cardiovascular disease, disorder and/or condition in the subject. In some embodiments, the acute cardiovascular event is a myocardial infarction.

In some embodiments, a method for treatment and/or prevention of atherosclerosis is disclosed, the method comprising administering to a subject in need thereof an effective amount of at least one compound of Formula (I) and/or a pharmaceutical composition comprising at least one compound of Formula (I). Atherosclerosis generally describes a disease of the arterial blood vessels. As used herein, "atherosclerosis" includes, but is not limited to, chronic and/or acute atherosclerotic inflammation prior to or subsequent to the formation of at least one atherosclerotic plaque in the subject. Atherosclerosis also includes, but is not limited to, chronic progressive atherosclerosis and/or atherosclerotic inflammation. Atherosclerosis also includes, but is not limited to, acute atherosclerosis and/or atherosclerotic inflammation subsequent to an acute vascular event in the subject (such as, for example, myocardial infarction).

In some embodiments, at least one compound of Formula (I) and/or a pharmaceutical composition comprising at least one compound of Formula (I) may be administered prior to or subsequent to the formation of at least one atherosclerotic plaque, lesion or atheroma in the subject.

In some embodiments, the formation, progression, destabilization and/or rupture of at least one atherosclerotic plaque within the subject is reduced.

Atherosclerotic plaques may be characterized as stable or unstable (i.e., vulnerable to destabilization). Unstable atherosclerotic plaques may be susceptible to disruption or rupture, which exposes thrombogenic material (i.e., thrombi) (e.g., collagen) to the circulation. This can produce interruptions in blood flood (ischemia) in local or distal arteries, which can result in cardiovascular complications, such as, for example, myocardial infarction (MI).

Destabilization of atherosclerotic plaques may occur via many mechanisms. Non-limiting examples of such mechanisms include superficial erosion of the endothelial cells that form the monolayer covering the intima, disruption of the microvessels that form in the atherosclerotic plaque, rupture (i.e., fracture) of the atherosclerotic plaque's fibrous cap, thinning or weakening of the fibrous cap (thus making it susceptible to rupture), and the presence or increase in inflammatory factors that mediate destabilization. (Libby P., *Nature*, 420: 868-874 (2002)).

A non-limiting example of inflammatory factors that mediate destabilization is the presence of inflammatory cells. The progression of atherosclerosis may be associated with systemically increased inflammatory myeloid cells that are recruited to atherosclerotic plaques. (Murphy, A. J. et al., *J. Clin. Invest.*, 121: 4138-4149 (2011); Averill, L. E et al., *Am. J. Pathol.*, 135: 369-377 (1989); Feldman, D. L. et al., *Arterioscler. Thromb.*, 11: 985-994 (1991); Swirski, F. K. et al., *J. Clin. Invest.*, 117: 195-205 (2007)). The presence of inflammatory myeloid cells may be detrimental to a stable plaque. (Llodra, J. et al., *Proc. Natl. Acad. Sci. U.S.A.*, 101: 11779-11784 (2004)).

In some embodiments, the stability of at least one atherosclerotic plaque within the subject is increased. Non-limiting examples of stable features of atherosclerotic plaques (i.e., stable phenotype) include smaller plaque size, reduced (i.e., decreased, diminished, smaller) necrotic core size (measured by, for example, necrotic core area), and a thicker fibrous cap of the atherosclerotic plaque. (See, e.g., Moore K. J. et al., *Cell* 145: 341-355 (2011)).

In some embodiments, the size of at least one atherosclerotic plaque within the subject is decreased. In some embodiments, the necrotic core size of at least one atherosclerotic plaque within the subject is decreased. In some embodiments, the fibrous cap thickness of at least one atherosclerotic plaque within the subject is increased.

In some embodiments, the administration of an effective amount of at least one compound of Formula (I) and/or a pharmaceutical composition comprising at least one compound of Formula (I) reduces the levels of extramedullary proliferation of hematopoietic stem and/or progenitor cells within the subject. In some embodiments, extramedullary proliferation of hematopoietic stem and/or progenitor cells is reduced in the spleen and/or the liver. Non-limiting examples of extramedullary proliferation of hematopoietic stem and/or progenitor cells include extramedullary hematopoiesis and extramedullary myelopoiesis.

In some embodiments, the administration of an effective amount of at least one compound of Formula (I) and/or a pharmaceutical composition comprising at least one compound of Formula (I) reduces the recruitment and/or infiltration of myeloid cells to at least one atherosclerotic plaque within the subject. Non-limiting examples of myeloid cells include monocytes, macrophages, neutrophils, basophils, eosinophils, erythrocytes, dendritic cells, and megakaryocytes and platelets.

In some embodiments, the at least one compound of Formula (I) and/or a pharmaceutical composition comprising at least one compound of Formula (I) is administered after angioplasty, stenting procedure, atherectomy, bypass surgery, or other vessel-corrective techniques.

In some embodiments, the at least one compound of Formula (I) and/or a pharmaceutical composition comprising at least one compound of Formula (I) is administered before angioplasty, stenting procedure, atherectomy, bypass surgery, or other vessel-corrective techniques.

In some embodiments, a method for treatment and prevention of myocardial infarction is disclosed, the method comprising administering to a subject in need thereof an effective amount of at least one compound of Formula (I) and/or a pharmaceutical composition comprising at least one compound of Formula (I). In some embodiments, the subject has previously suffered a myocardial infarction. In some embodiments, a compound of Formula (I) may be administered before the occurrence of a myocardial infarction in the subject. In some embodiments, a compound of Formula (I) may be administered after the occurrence of a first or subsequent myocardial infarction in the subject.

In some embodiments, at least one compound of Formula (I) and/or a pharmaceutical composition comprising at least one compound of Formula (I) is administered to the subject: within one (1) day of the subject suffering a myocardial infarction, within one (1) week of the subject suffering a myocardial infarction, within two (2) weeks of the subject suffering a myocardial infarction, within three (3) weeks of the subject suffering a myocardial infarction, within four (4) weeks of the subject suffering a myocardial infarction, within eight (8) weeks of the subject suffering a myocardial infarction, or within twelve (12) weeks of the subject suffering a myocardial infarction.

In some embodiments, a method for the treatment of diseases, disorders, or conditions associated with cardiac remodeling, the method comprising administering to a subject in need thereof an effective amount of at least one compound of Formula (I) and/or a pharmaceutical composition comprising at least one compound of Formula (I).

In some embodiments, a method for the treatment of sickle cell disease or complications associated therewith is disclosed, the method comprising administering to a subject in need thereof an effective amount of at least one compound of Formula (I) and/or a pharmaceutical composition comprising at least one compound of Formula (I).

In some embodiments, a method for treatment and prevention of vaso-occlusive crisis or complications associated therewith is disclosed, the method comprising administering to a subject in need thereof an effective amount of at least one compound of Formula (I) and/or a pharmaceutical composition comprising at least one compound of Formula (I).

In some embodiments, a method for treatment and/or prevention of pathological angiogenesis is disclosed, the method comprising administering to a subject in need thereof an effective amount of at least one compound of Formula (I) and/or a pharmaceutical composition comprising at least one compound of Formula (I).

In some embodiments, the pathological angiogenesis in the eye. Examples of ocular diseases, disorders, or conditions associated with pathological angiogenesis include age-related macular degeneration, ocular histoplasmosis syndrome, neovascular glaucoma, retrolental fibroplasia, pathologic myopia, angioid streaks, idiopathic disorders, choroiditis, choroidal rupture, overlying choroid nevi, graft rejection, herpes simplex keratitis, leishmaniasis, onchocerciasis, certain inflammatory diseases such as dry eye syndrome, and trauma to the eye (e.g., cornea).

In some embodiments, the present disclosure is directed to methods for treatment and prevention of pathological angiogenesis in patients with cancer.

In some embodiments, a method for treatment and/or prevention of an epileptic syndrome is disclosed, the method comprising administering to a subject in need thereof at least one compound of Formula (I) and/or a pharmaceutical composition comprising at least one compound of Formula (I). Examples of an epileptic syndrome include epilepsy, Rasmussen's syndrome and West syndrome. Other syndromes which are multi-system disorders but with the primary disability resulting from neurological effects including epilepsy, are considered epileptic syndromes for purposes of the present invention. An example of such a syndrome is tuberous sclerosis syndrome.

The compounds of the present disclosure and pharmaceutical compositions comprising at least one such compound may be administered in combination with at least one additional antiepileptic agent (e.g. acetazolamide, carbamazepine, clobazan, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, rufinamide, sodium valproate, stiripentol, tiagabine, topiramate, vigabatrin, zonisamide). The compounds of the present disclosure and pharmaceutical compositions comprising at least one such compound may function independently from the antiepileptic agent or may function in coordination with the at least one antiepileptic agent. In addition, the administration of one or more of the compounds or compositions may be in conjunction with one or more other therapies, e.g., for reducing toxicities of therapy. For example, at least one palliative agent to counteract (at least in part) a side effect of therapy may be administered. Agents (chemical or biological) that promote recovery or enhancement of appetite, or counteract nausea or fatigue, are examples of such agents.

The compounds of the present disclosure and pharmaceutical composition comprising at least one such compound may be administered before, after, or concurrently with administration of at least one additional anti-thrombosis agent or at least one palliative agent to reduce a side effect of therapy. Where administration is concurrent, the combination may be administered from a single container or two (or more) separate containers.

In some embodiments, a method for treatment and/or prevention of a neurodegenerative disease is disclosed, the method comprising administering to a subject in need thereof an effective amount of at least one compound of Formula (I) and/or a pharmaceutical composition comprising at least one compound of Formula (I). Examples of neurodegenerative diseases include such as selected from Parkinson's disease, dementia with Lewy bodies, pure autonomic failure (PAF), Alzheimer's disease, neurodegeneration with brain iron accumulation, type I (also referred to as adult neuroaxonal dystrophy or Hallervorden-Spatz syndrome), traumatic brain injury, amyotrophic lateral sclerosis, Pick disease, multiple system atrophy (including Shy-Drager syndrome, striatonigral degeneration, and olivopontocerebellar atrophy) and stroke, multiple sclerosis, epilepsy and infantile neuroaxonal dystrophy.

In some embodiments, a method for treatment and/or prevention of α-synucleinopathies is disclosed, the method comprising administering to a subject in need thereof an effective amount of at least one compound of Formula (I) and/or a pharmaceutical composition comprising at least one compound of Formula (I). Examples of α-synucleinopathies include such as selected from Parkinson's disease, dementia with Lewy bodies, pure autonomic failure (PAF), Alzheimer's disease, neurodegeneration with brain iron accumulation, type I (also referred to as adult neuroaxonal dystrophy or Hallervorden-Spatz syndrome), traumatic brain injury, amyotrophic lateral sclerosis, Pick disease, multiple system atrophy (including Shy-Drager syndrome, striatonigral degeneration, and olivopontocerebellar atrophy) and stroke, multiple sclerosis, epilepsy and infantile neuroaxonal dystrophy.

The compounds of the present disclosure and pharmaceutical compositions comprising at least one such compound may be administered in combination with at least one additional agent for the treatment of neurodegeneration or symptoms thereof (e.g. donepezil, galantamine, memantine, rivastigmine, levodopa, carbidopa, dopamine agonists, COMT inhibitors, MAO inhibitors, anticholinergic agents, corticosteroids, beta interferons, ocrelizumab, glatiramer acetate, dimethyl fumarate, fingolimod, teriflunomide, natalizumab, alemtuzumab, mitoxantrone, riluzole, edaravone). The compounds of the present disclosure and pharmaceutical composition comprising at least one such compound may be administered before, after, or concurrently with administration of at least one additional agent for the treatment of neurodegeneration or symptoms thereof. Where administration is concurrent, the combination may be administered from a single container or two (or more) separate containers.

In some embodiments, a method for treatment and prevention of a fibrosing disease or condition is disclosed, the method comprising administering to a subject in need thereof an effective amount of at least one compound of Formula (I) and/or a pharmaceutical composition comprising at least one compound of Formula (I). Examples of fibrosing diseases and conditions include such as selected from rheumatoid arthritis, lupus, pathogenic fibrosis, fibrosing disease, heart disease, heart remodeling post MI, nonalcoholic fatty liver disease (NASH), idiopathic pulmonary fibrosis (IPF), fibrosis associated with thrombosis, fibrosis associated with macular degeneration, fibrotic lesions such as those formed after *Schistosoma japonicum* infection, radiation damage, autoimmune diseases, Lyme disease, chemotherapy induced fibrosis, HIV or infection-induced focal Sclerosis, failed back syndrome due to spinal Surgery scarring, abdominal adhesion post-Surgery scarring, fibrocystic formations, fibrosis after spinal injury, Surgery-induced fibrosis, mucosal fibrosis, peritoneal fibrosis caused by dialysis, Adalimumab-associated pulmonary fibrosis, and nephrogenic fibrosing dermopathy.

In some embodiments, the fibrosis is fibrosis of the liver resulting from conditions including but not limited to alcohol, drug, or chemically induced cirrhosis, ischemia-reperfusion injury after hepatic transplant, necrotizing hepatitis, hepatitis B, hepatitis C, primary biliary cirrhosis, primary sclerosing cholangitis, and nonalcoholic steatohepatitis.

In some embodiments, the fibrosis is fibrosis in the kidney resulting from conditions including but not limited to proliferative and Sclerosing glomerulonephritis, nephrogenic fibrosing dermopathy, diabetic nephropathy, renal tubulointerstitial fibrosis, and focal segmental glomerulosclerosis.

In some embodiments, the fibrosis is fibrosis of the lung resulting from conditions including but not limited to pulmonary interstitial fibrosis, sarcoidosis, pulmonary fibrosis, idiopathic pulmonary fibrosis, asthma, chronic obstructive pulmonary disease, diffuse alveolar damage disease, pulmonary hypertension, neonatal bronchopulmonary dysplasia, chronic asthma, and emphysema. There are several subnames or synonyms for pulmonary fibrosis including, but not limited to, cryptogenic fibrosing alveolitis, diffuse interstitial fibrosis, idiopathic interstitial pneumonitis, Hamman Rich syndrome, silicosis, asbestosis, berylliosis, coal worker's pneumoconiosis, coal miner's disease, miner's asthma, anthracosis, and anthracosilicosis.

In some embodiments, the fibrosis is fibrosis of the heart or pericardium resulting from conditions including but not limited to myocardial fibrosis, atherosclerosis, coronary artery restenosis, congestive cardiomyopathy, heart failure, and other post-ischemic conditions.

In some embodiments, the fibrosis is fibrosis of the eye resulting from conditions including but not limited to macular degeneration, exophthalmos of Grave's disease, proliferative vitreoretinopathy, anterior capsule cataract, corneal fibrosis, corneal scarring due to surgery, trabeculectomy-induced fibrosis, progressive sub-retinal fibrosis, multifocal granulomatous chorioretinitis, fibrosis due to wide angle glaucoma trabeculotomy, and other eye fibrosis.

In some embodiments, the fibrosis is fibrosis of the brain resulting from conditions including but not limited to glial scar tissue.

In some embodiments, the fibrosis is fibrosis of the skin resulting from conditions including but not limited to Depuytren's contracture, Scleroderma, keloid scarring, psoriasis, hyper-trophic scarring due to burns, atherosclerosis, restenosis, and pseudoscleroderma caused by spinal cord injury.

In some embodiments, the fibrosis is fibrosis of tissue including but not limited to the mouth or esophagus, pancreas, gastrointestinal tract, breast, bone, bone marrow, genitourinary system.

The terms "treat" and "treatment" include medical management of a disease, disorder, and/or condition of a subject as would be understood by a person of ordinary skill in the art (see, e.g., Stedman's Medical Dictionary). In general, an appropriate dose and treatment regimen provide at least one of the compounds of the present disclosure in an amount sufficient to provide therapeutic and/or prophylactic benefit. For both therapeutic treatment and prophylactic or preventative measures, therapeutic and/or prophylactic benefit includes, for example, an improved clinical outcome, wherein the object is to prevent or slow or lessen an undesired physiological change or disorder, or to prevent or slow or lessen the expansion or severity of such disorder. As discussed herein, beneficial or desired clinical results from treating a subject include, but are not limited to, abatement, lessening, or alleviation of symptoms that result from or are associated with the disease, condition, and/or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival "Treatment" can include prolonging survival when compared to expected survival if a subject were not receiving treatment.

In some embodiments of the methods described herein, the subject is a human. In some embodiments of the methods described herein, the subject is a non-human animal. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

The effectiveness of the compounds of the present disclosure in treating and/or preventing diseases, disorders, and/or conditions treatable by inhibiting an activity of galectin-3 can readily be determined by a person of ordinary skill in the relevant art. Determining and adjusting an appropriate dosing regimen (e.g., adjusting the amount of compound per dose and/or number of doses and frequency of dosing) can also readily be performed by a person of ordinary skill in the relevant art. One or any combination of diagnostic methods, including physical examination, assessment and monitoring of clinical symptoms, and performance of analytical tests and methods described herein, may be used for monitoring the health status of the subject.

Also provided herein are pharmaceutical compositions comprising at least one compound of Formula (I). In some embodiments, the pharmaceutical compositions further comprise at least one additional pharmaceutically acceptable ingredient.

In pharmaceutical compositions, any one or more of the compounds of the present disclosure may be administered in the form of a pharmaceutically acceptable derivative, such as a salt, and/or it or they may also be used alone and/or in appropriate association, as well as in combination, with other pharmaceutically active compounds.

An effective amount or therapeutically effective amount refers to an amount of at least one compound of the present disclosure or a pharmaceutical composition comprising at least one such compound that, when administered to a subject, either as a single dose or as part of a series of doses, is effective to produce at least one therapeutic effect. Optimal doses may generally be determined using experimental models and/or clinical trials. Design and execution of pre-clinical and clinical studies for each of the therapeutics (including when administered for prophylactic benefit) described herein are well within the skill of a person of ordinary skill in the relevant art. The optimal dose of a therapeutic may depend upon the body mass, weight, and/or blood volume of the subject. In general, the amount of at least one compound of Formula (I) as described herein, that is present in a dose, may range from about 0.1 mg to about 100 mg per kg weight of the subject. The minimum dose that is sufficient to provide effective therapy may be used in some embodiments. Subjects may generally be monitored for therapeutic effectiveness using assays suitable for the disease, disorder and/or condition being treated or prevented, which assays will be familiar to those having ordinary skill in the art and are described herein. The level of a compound that is administered to a subject may be monitored by determining the level of the compound (or a metabolite of the compound) in a biological fluid, for example, in the blood, blood fraction (e.g., serum), and/or in the urine, and/or other biological sample from the subject. Any method practiced in the art to detect the compound, or metabolite thereof, may be used to measure the level of the compound during the course of a therapeutic regimen.

The dose of a compound described herein may depend upon the subject's condition, that is, stage of the disease, severity of symptoms caused by the disease, general health status, as well as age, gender, and weight, and other factors apparent to a person of ordinary skill in the medical art. Similarly, the dose of the therapeutic for treating a disease, disorder, and/or condition may be determined according to parameters understood by a person of ordinary skill in the medical art.

Pharmaceutical compositions may be administered in any manner appropriate to the disease, disorder, and/or condition to be treated as determined by persons of ordinary skill in the medical arts. An appropriate dose and a suitable duration and frequency of administration will be determined by such factors as discussed herein, including the condition of the patient, the type and severity of the patient's disease, the particular form of the active ingredient, and the method of administration. In general, an appropriate dose (or effective dose) and treatment regimen provides the composition(s) as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein may be administered to a subject in need thereof by any one of several routes that effectively delivers an effective amount of the compound. Non-limiting examples of suitable administrative routes include topical, oral, nasal, intrathecal, enteral, buccal, sublingual, transdermal, rectal, vaginal, intraocular, subconjunctival, sublingual, and parenteral administration, including subcutaneous, intravenous, intramuscular, intrasternal, intracavernous, intrameatal, and intraurethral injection and/or infusion.

The pharmaceutical compositions described herein may, for example, be sterile aqueous or sterile non-aqueous solutions, suspensions, or emulsions, and may additionally comprise at least one pharmaceutically acceptable excipient (i.e., a non-toxic material that does not interfere with the activity of the active ingredient). Such compositions may, for example, be in the form of a solid, liquid, or gas (aerosol). Alternatively, the compositions described herein may, for example, be formulated as a lyophilizate, or compounds described herein may be encapsulated within liposomes using technology known in the art. The pharmaceutical compositions may further comprise at least one additional pharmaceutically acceptable ingredient, which may be biologically active or inactive. Non-limiting examples of such ingredients include buffers (e.g., neutral buffered saline or phosphate buffered saline), carbohydrates (e.g., glucose, mannose, sucrose or dextrans), mannitol, proteins, polypeptides, amino acids (e.g., glycine), antioxidants, chelating agents (e.g., EDTA and glutathione), stabilizers, dyes, flavoring agents, suspending agents, and preservatives.

Any suitable excipient or carrier known to those of ordinary skill in the art for use in compositions may be employed in the compositions described herein. Excipients for therapeutic use are well known, and are described, for example, in Remington: The Science and Practice of Pharmacy (Gennaro, 21$^{st}$ Ed. Mack Pub. Co., Easton, PA (2005)). In general, the type of excipient may be selected based on the mode of administration, as well as the chemical composition of the active ingredient(s). Compositions may be formulated for the particular mode of administration. For parenteral administration, pharmaceutical compositions may further comprise water, saline, alcohols, fats, waxes, and buffers. For oral administration, pharmaceutical compositions may further comprise at least one component chosen, for example, from any of the aforementioned ingredients, excipients and carriers, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose, and magnesium carbonate.

The pharmaceutical compositions (e.g., for oral administration or delivery by injection) may be in the form of a liquid. A liquid composition may include, for example, at least one the following: a sterile diluent such as water for injection, saline solution, including for example physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. In some embodiments, the pharmaceutical composition comprises physiological saline. In some embodiments, the pharmaceutical composition is an injectable composition, and in some embodiments, the injectable composition is sterile.

For oral formulations, at least one of the compounds of the present disclosure can be used alone or in combination with at least one additive appropriate to make tablets, powders, granules and/or capsules, for example, those chosen from conventional additives, disintegrators, lubricants, diluents, buffering agents, moistening agents, preservatives, coloring agents, and flavoring agents. The pharmaceutical compositions may be formulated to include at least one buffering agent, which may provide for protection of the active ingredient from low pH of the gastric environment and/or an enteric coating. A pharmaceutical composition may be formulated for oral delivery with at least one flavoring agent, e.g., in a liquid, solid or semi-solid formulation and/or with an enteric coating.

Oral formulations may be provided as gelatin capsules, which may contain the active compound or biological along with powdered carriers. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract.

A pharmaceutical composition may be formulated for sustained or slow release. Such compositions may generally be prepared using well known technology and administered by, for example, oral, rectal or subcutaneous implantation, or by implantation at the desired target site. Sustained-release formulations may contain the active therapeutic dispersed in a carrier matrix and/or contained within a reservoir surrounded by a rate controlling membrane. Excipients for use within such formulations are biocompatible, and may also be biodegradable; the formulation may provide a relatively constant level of active component release. The amount of active therapeutic contained within a sustained release formulation depends upon the site of implantation, the rate and expected duration of release, and the nature of the condition to be treated or prevented.

The pharmaceutical compositions described herein can be formulated as suppositories by mixing with a variety of bases such as emulsifying bases or water-soluble bases. The pharmaceutical compositions may be prepared as aerosol formulations to be administered via inhalation. The pharmaceutical compositions may be formulated into pressurized acceptable propellants such as dichlorodifluoromethane, propane, nitrogen and the like.

The compounds of the present disclosure and pharmaceutical compositions comprising these compounds may be administered topically (e.g., by transdermal administration). Topical formulations may be in the form of a transdermal patch, ointment, paste, lotion, cream, gel, and the like. Topical formulations may include one or more of a penetrating agent or enhancer (also call permeation enhancer), thickener, diluent, emulsifier, dispersing aid, or binder. Physical penetration enhancers include, for example, electrophoretic techniques such as iontophoresis, use of ultrasound (or "phonophoresis"), and the like. Chemical penetration enhancers are agents administered either prior to, with, or immediately following administration of the therapeutic, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneräs et al., *J. Pharm. Pharmacol.* 54:499-508 (2002); Karande et al., *Pharm. Res.* 19:655-60 (2002); Vaddi et al., *Int. J. Pharm.* 91:1639-15 (2002); Ventura et al., *J. Drug Target* 9:379-93 (2001); Shokri et al., *Int. J. Pharm.* 228(1-2):99-107 (2001); Suzuki et al., *Biol. Pharm. Bull.* 24:698-700 (2001); Alberti et al., *J. Control Release* 71:319-27 (2001); Goldstein et al., *Urology* 57:301-5 (2001); Kiijavainen et al., *Eur. J. Pharm. Sci.* 10:97-102 (2000); and Tenjarla et al., *Int. J. Pharm.* 192: 147-58 (1999).

Kits comprising unit doses of at least one compound of the present disclosure, for example in oral or injectable doses, are provided. Such kits may include a container comprising the unit dose, an informational package insert describing the use and attendant benefits of the therapeutic in treating the pathological condition of interest, and/or optionally an appliance or device for delivery of the at least one compound of Formula (I) and/or pharmaceutical composition comprising the same.

EXAMPLES

Example 1

Synthesis of Compound 13

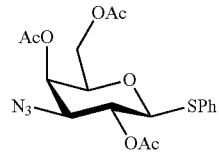

2

Compound 2: Compound 1 (1.5 g, 4.02 mmoles) was dissolved in DCM (30 mL). Thiophenol (0.9 g, 0.82 mL, 8.04 mmoles) was added followed by dropwise addition of boron trifluoride diethyl etherate (1.79 g, 1.49 mL, 12.06 mmoles). The reaction mixture was stirred at room temperature for 2 days. The reaction quenched by addition of aqueous saturated NaHCO$_3$, transferred to a separatory funnel, and extracted 3 times with DCM. The combined organic phases were dried over sodium sulfate, filtered and concentrated. The residue was purified by flash chromatography to give 2 as an off-white solid (1.1 g, 65% yield) LCMS (ESI): m/z calculated for C$_{18}$H$_{21}$N$_3$O$_7$S: 423.4, found 424.1 (M+1); 446.1 (M+±Na).

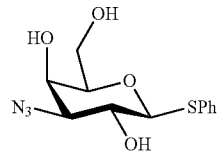

3

Compound 3: Compound 2 (1.1 g, 2.60 mmoles) was dissolved in methanol (25 mL) at room temperature. Sodium methoxide (0.1 mL, 25% sol. in MeOH) was added and the reaction mixture was stirred at room temperature for 2 hours. The reaction mixture neutralized by the addition of Amberlyst acidic resin, filtered and concentrated to give crude 3, which was used for the next step without further purification. LCMS (ESI): m/z calculated for C$_{12}$H$_{15}$N$_3$O$_4$S: 297.3, found 298.1 (M+1); 320.1 (M+Na).

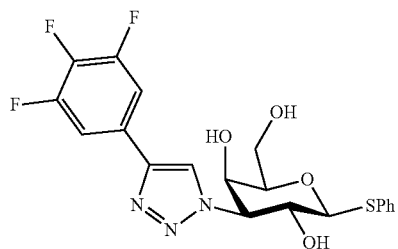

4

Compound 4: Crude compound 3 (2.60 mmoles), 3,4,5-trifluorophenyl-1-acetylene (2.5 equiv), THPTA (0.11 equiv), and copper (II) sulfate (0.1) were dissolved in methanol (15 mL) at room temperature. Sodium ascorbate (2.4 equiv) dissolved in water was added and the reaction mixture was stirred overnight at room temperature. The resultant precipitate was collected by filtration, washed with hexanes and water, and dried to give compound 4 as a pale yellow solid (1.2 g, 100% yield for 2 steps). LCMS (ESI): m/z calculated for $C_{20}H_{18}F_3N_3O_4S$: 453.1, found 454.2 (M+1); 476.2 (M+Na).

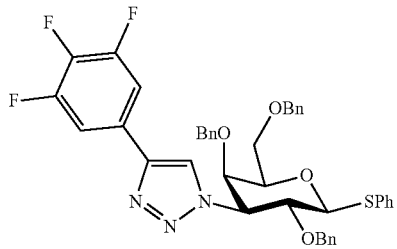

5

Compound 5: Compound 4 (1.2 g, 2.65 mmoles) was dissolved in DMF (15 mL) and cooled on an ice bath. Sodium hydride (60% oil dispersion, 477 mg, 11.93 mmoles) was added and the mixture stirred for 30 minutes. Benzyl bromide (1.42 mL, 11.93 mmoles) was added and the reaction was warmed to room temperature and stirred overnight. The reaction mixture was quenched by the addition of aqueous saturated ammonium chloride solution, transferred to a separatory funnel and extracted 3 times with ether. The combined organic phases were dried over magnesium sulfate, filtered, and concentrated. The residue was purified by flash chromatography to afford compound 5 (1.8 g, 94% yield). LCMS (ESI): m/z calculated for $C_{41}H_{36}F_3N_3O_4S$: 723.2, found 724.3 (M+1); 746.3 (M+Na).

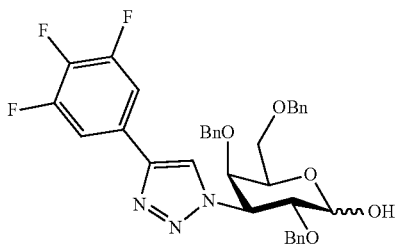

6

Compound 6: Compound 5 (1.8 g, 2.49 mmol) was dissolved in acetone (20 mL) and water (2 mL) and cooled on an ice bath. Trichloroisocyanuric acid (637 mg, 2.74 mmoles) was added and the reaction mixture stirred on the ice bath for 3 h. The acetone was removed in vacuo and the residue was diluted with DCM, transferred to a separatory funnel, and washed with saturated aqueous $NaHCO_3$. The organic phase was concentrated and the residue was purified by flash chromatography to afford compound 6 (1.5 g, 95%). LCMS (ESI): m/z calculated for $C_{35}H_{32}F_3N_3O_5$: 631.2, found 632.2 (M+1); 654.2 (M+Na).

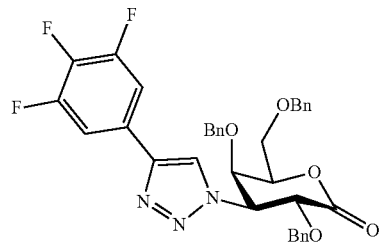

7

Compound 7: Compound 6 (1.0 g, 1.58 mmoles) was dissolved in DCM (20 mL) and cooled on an ice bath. Dess-Martin periodinane (1.0 g, 2.37 mmoles) was added and mixture was allowed to warm to room temperature and stirred overnight. The reaction mixture quenched by the addition of aqueous saturated $NaHCO_3$, transferred to a separatory funnel, and extracted 2 times with DCM. The combined organic phases were dried over sodium sulfate, filtered, and concentrated. The residue was purified by flash chromatography to afford compound 7 (520 mg, 52% yield). LCMS (ESI): m/z calculated for $C_{35}H_{30}F_3N_3O_5$: 629.2, found 652.2 (M+Na); 662.2 (M+MeOH+1); 684.2 (M+MeOH+Na).

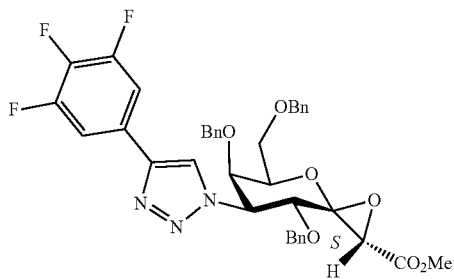

8

Compound 8: Methyl bromoacetate (253 mg, 1.65 mmoles) dissolved in 0.5 mL of THF was added dropwise to a solution of lithium bis(trimethylsilyl)amide (1.0 M in THF, 1.65 mL, 1.65 nmoles) cooled at −78 C. The reaction mixture was stirred for 30 minutes at −78 C. Compound 7 (260 mg, 0.41 mmoles) dissolved in THF (2.0 mL) was then added. The reaction mixture was stirred at −78 C for 30 minutes. The reaction was quenched by the addition of aqueous saturated $NH_4Cl$ and warmed to rt. The reaction mixture was transferred to a separatory funnel and extracted 3 times with ethyl acetate. The combined organic phases were dried over sodium sulfate, filtered and concentrated. The residue was separated by flash chromatography to afford compound 8 (183 mg, 640% yield).

$^1$H NMR (400 MHz, Chloroform-d) δ 7.38-7.22 (m, 91H), 7.15-7.11 (m, 3H), 7.09 (dd, J=8.4, 6.6 Hz, 1H), 7.06-7.00 (m, 2H), 6.98-6.93 (m, 2H), 5.11 (dd, J=11.3, 3.2 Hz, 1H), 4.60 (d, J=11.8 Hz, 1H), 4.57-4.49 (m, 2H), 4.49-4.42 (m, 2H), 4.35 (d, J=11.8 Hz, 1H), 4.14 (d, J=3.2 Hz, 1H), 4.05 (s, 1H), 4.02 (d, J=7.0 Hz, 1H), 3.84 (d, J=11.0 Hz, 1H), 3.81 (s, 3H), 3.70 (dd, J=9.5, 7.7 Hz, 1H), 3.62 (dd, J=9.4, 6.0 Hz, 1H). LCMS (ESI): m/z calculated for $C_{38}H_{34}F_3N_3O_7$: 701.2, found 702.3 (M+1); 724.3 (M+Na).

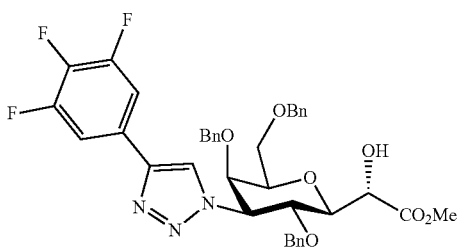

9

Compound 9: Compound 8 (5.0 g, 7.13 mmol) was azeotroped with toluene two times under reduced pressure, and then dried under high vacuum for 2 hours. It was then dissolved in anhydrous CH$_2$Cl$_2$ (125 mL) and cooled on an ice bath while stirring under an atmosphere of argon. Tributyltin hydride (15.1 mL, 56.1 mmol) was added dropwise and the solution was allowed to stir for 25 minutes on the ice bath. Trimethylsilyl triflate (2.1 mL, 11.6 mmol) dissolved in 20 mL of anhydrous CH$_2$Cl$_2$ was then added dropwise over the course of 5 minutes. The reaction was slowly warmed to ambient temperature and stirred for 16 hours. The reaction mixture was then diluted with CH$_2$Cl$_2$ (50 mL), transferred to a separatory funnel, and washed with saturated aqueous NaHCO$_3$ (50 mL). The aqueous phase was separated and extracted with CH$_2$Cl$_2$ (50 mL×2). The combined organic phases were washed with saturated aqueous NaHCO$_3$ (50 mL), dried over Na$_2$SO$_4$, filtered, and concentrated. The residue was purified by flash chromatography (hexanes to 40% EtOAc in hexanes, gradient) to afford compound 9 (2.65 g, 48%).

$^1$H-NMR (400 MHz, CDCl$_3$): δ 7.65 (s, 11H), 7.36-7.22 (m, 8H), 7.16-7.06 (m, 71H), 6.96-6.90 (m, 2H), 5.03 (dd, J=10.7, 3.2 Hz, 1H), 4.72 (d, J=2.3 Hz, 1H), 4.51 (dt, J=22.6, 11.4 Hz, 3H), 4.41 (d, J=10.9 Hz, 1H), 4.32 (dd, J=10.7, 9.2 Hz, 1H), 4.07 (d, J=3.1 Hz, 1H), 394 (d, J=10.9 Hz, 1H), 392-3.84 (m, 3H), 3.78-3.71 (m, 4H), 3.65 (dd, J=9.1, 5.5 Hz, 1H), 0.24 (s, 9H). LCMS (ESI): m/z (M+Na) calculated for C$_{41}$H$_{44}$F$_3$N$_3$O$_7$SiNa: 798.87, found 798.2.

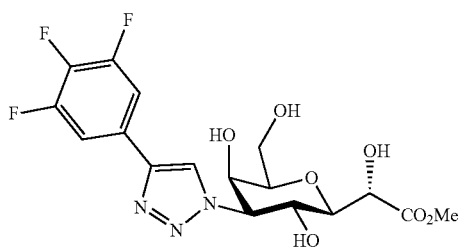

10

Compound 10: To a solution of compound 9 (2.65 g, 3.4 mmol) was in anhydrous MeOH (40 mL) was added Pd(OH)$_2$ (0.27 g, 20% by wt). The mixture was cooled on an ice bath and stirred for 30 minutes. Triethylsilane (22 mL, 137 mmol) was added dropwise. The solution was allowed to slowly warm to ambient temperature and stirred for 16 hours. The reaction mixture was filtered through a bed of Celite and concentrated. The residue was purified by flash chromatography (hexanes to 100% EtOAc, gradient) to afford compound 10 (1.09 g, 73%).

$^1$H-NMR (400 MHz, CD$_3$OD): δ 8.57 (s, 1H), 7.77-7.53 (m, 2H), 4.91-4.82 (m, 1H), 4.66-4.59 (m, 1H), 4.55 (dd, J=10.8, 9.4 Hz, 1H), 4.13 (d, J=2.8 Hz, 1H), 3.86 (dd, J=9.4, 2.1 Hz, 1H), 3.81 (s, 3), 3.77-3.74 (m, 114), 3.71-3.68 (m, 2H). LCMS (ESI): m/z (M+Na) calculated for C$_{17}$H$_{18}$F$_3$N$_3$O$_7$Na: 456.33, found 456.0.

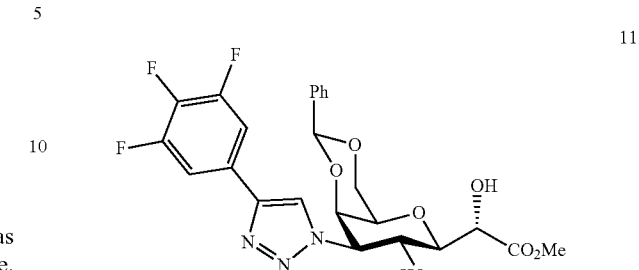

11

Compound 11: Compound 10 (1.09 g, 2.5 mmol) and CSA (0.115 g, 0.49 mmol) were suspended in anhydrous MeCN (80 mL) under an argon atmosphere. Benzaldehyde dimethyl acetal (0.45 mL, 2.99 mmol) was added dropwise. The reaction mixture was allowed to stir for 16 hours at ambient temperature, during which time it became a homogenous solution. The reaction mixture was then neutralized with a few drops of Et$_3$N, and concentrated. The residue was purified via flash chromatography (CH$_2$Cl$_2$ to 10% MeOH in CH$_2$Cl$_2$, gradient) to afford compound 11 (978 mg, 75%).

$^1$H NMR (400 MHz, DMSO-d6): δ 8.84 (s, 11H), 7.95-7.73 (m, 2H), 7.33 (qdt, J=8.4, 5.6, 2.7 Hz, 5H), 5.51 (t, J=3.8 Hz, 2H), 5.47 (d, J=6.8 Hz, 1H), 5.14 (dd, J=10.8, 3.6 Hz, 1H), 4.54 (dd, J=6.7, 2.2 Hz, 1H), 4.47 (ddd, J=10.8, 9.3, 7.5 Hz, 1H), 4.40 (d, J=4.0 Hz, 1H), 4.09-3.99 (m, 21H), 3.85 (dd, J=9.3, 2.2 Hz, 1H), 3.81-3.76 (m, 1H), 3.71 (s, 3H). LCMS (ESI): m/z (M+Na) calculated for C$_{24}$H$_{22}$F$_3$N$_3$O$_7$Na: 544.43, found 544.1.

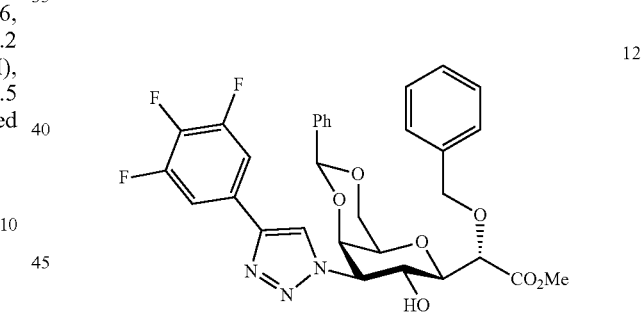

12

Compound 12: Compound 11 (25.2 mg, 0.048 mmol) was azeotroped with toluene 2 times under reduced pressure, dried under high vacuum for 2 hours, then dissolved in anhydrous DMF (2 mL) and cooled on an ice bath. Benzyl bromide (6 uL, 0.05 mmol) dissolved in 0.5 mL of anhydrous DMF was added and the reaction and was stirred under an atmosphere of argon for 30 minutes at 0° C. Sodium hydride (2 mg, 0.05 mmol, 60%) was added and the reaction was allowed to gradually warm to ambient temperature while stirring for 16 hours. The reaction mixture was diluted with EtOAc (20 mL), transferred to a separatory funnel, and washed with H$_2$O (10 mL). The aqueous phase was separated and extracted with EtOAc (10 mL×3). The combined organic phases were washed with H$_2$O (10 mL×3), dried over Na$_2$SO$_4$, filtered, and concentrated. The residue was purified via preparative TLC (5% MeOH in CH$_2$Cl$_2$) to afford compound 12 (6.3 mg, 21%). LCMS (ESI): m/z (M+Na) calculated for C$_{31}$H$_{28}$F$_3$N$_3$O$_7$Na: 634.55, found 634.1.

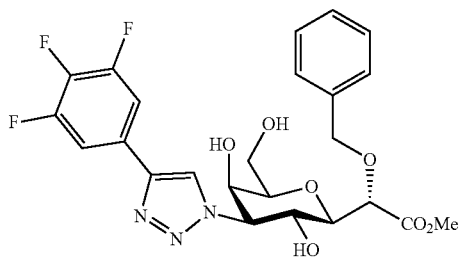

13

Compound 13: Compound 12 (6.3 mg, 0.01 mmol) was dissolved in anhydrous MeOH (1 mL) containing CSA (0.26 mg, 0.001 mmol). The reaction mixture was heated to 76° C. in a screw-cap scintillation vial while stirring. After 2 hours, an additional 0.13 mg of CSA in 0.5 mL of MeOH was added. The reaction mixture was stirred at 76° C. for 16 hours. The reaction mixture concentrated under reduced pressure. The residue was purified via preparative TLC (10% MeOH in $CH_2Cl_2$) to afford compound 13 (4.2 mg, 80%).

$^1$H NMR (400 MHz, DMSO-$d_6$) δ 8.80 (s, 1H), 7.94-7.86 (m, 2H), 7.48-7.42 (m, 2H), 7.38 (t, J=7.4 Hz, 2H), 7.36-7.28 (m, 1H), 5.46 (d, J=7.7 Hz, 1H), 5.28 (d, J=6.0 Hz, 1H), 4.85 (dd, J=10.7, 2.9 Hz, 1H), 4.67 (d, J=11.0 Hz, 1H), 4.62-4.58 (m, 1H), 4.54 (d, J=11.1 Hz, 1H), 4.44 (d, J=2.5 Hz, 1H), 4.36 (q, J=9.5 Hz, 1H), 3.95-3.90 (m, 1H), 3.78 (dd, J=9.3, 2.5 Hz, 1H), 3.71 (s, 3H), 3.61-3.54 (m, 1H), 3.52-3.43 (m, 1H), 3.43-3.38 (m, 1H). LC MS (ESI): m/z (M+Na) calculated for $C_{24}H_{24}F_3N_3O_7Na$: 546.45, found 546.0.

Example 2

Synthesis of Compound 14

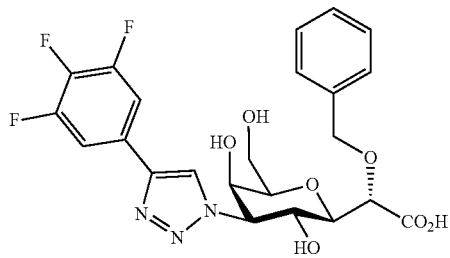

14

Compound 14: To a solution of compound 13 (3.5 mg, 0.007 mmoles) in methanol (0.5 mL) was added 1.0 M NaOH solution (0.1 mL). The reaction mixture was stirred overnight at room temperature then neutralized with acidic resin, filtered and concentrated. The residue was purified by reverse phase chromatography using a C-8 matrix to afford 3.0 mg compound 14 (90%). LCMS (ESI): m/z (M+Na) calculated for $C_{23}H_{22}F_3N_3O_7$: 509.1, found 508.2 (M−H).

Example 3

Synthesis of Compound 16

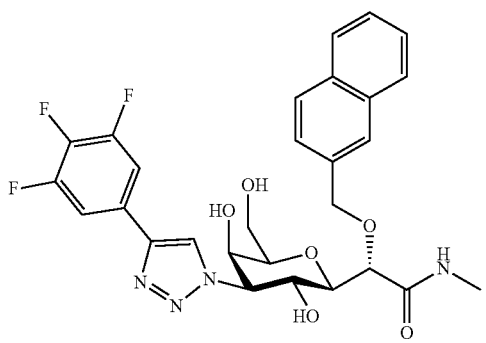

16

Compound 16: Compound 15 (19 mg, 0.029 mmol, prepared according to FIG. 1) was dissolved in a solution of methylamine (2 M THF, 2 mL, 4 mmol) in a screw-cap scintillation vial. The reaction mixture was stirred at 76° C. for 16 hours. The reaction mixture was concentrated and the residue was dissolved in MeOH (2.5 mL) containing CSA (1 mg, 0.0043 mmol). The reaction mixture was stirred at 76° C. for 16 hours. The reaction mixture was concentrated. The residue was purified via flash chromatography ($CH_2Cl_2$ to 15% MeOH in $CH_2Cl_2$, gradient) to afford compound 16 (11.3 mg, 68% a over 2 steps).

$^1$H NMR (400 MHz, DMSO-$d_6$) δ 8.74 (s, 11H), 7.99 (s, 1H), 7.96-7.91 (m, 3H), 7.90-7.83 (m, 2H), 7.78 (q, J=4.7 Hz, 1H), 7.68 (dd, J=8.5, 1.6 Hz, 1H), 7.55-7.49 (m, 2H), 5.41 (d, J=8.0 Hz, 1H), 5.28 (d, J=5.9 Hz, 1H), 4.88-4.79 (m, 2H), 4.74 (d, J=11.6 Hz, 1H), 4.54 (t, J=5.6 Hz, 1H), 4.46-4.36 (m, 1H), 4.22 (d, J=1.7 Hz, 1H), 3.96 (dd, J=6.1, 2.9 Hz, 1H), 3.72 (dd, J=9.4, 1.7 Hz, 1H), 3.60-3.46 (m, 2H), 3.45-3.37 (m, 1H), 2.65 (d, J=4.7 Hz, 3H). LCMS (ESI): m/z (M+Na) calculated for $C_{28}H_{27}F_3N_4O_6Na$: 595.52, found 595.1.

Example 4

Synthesis of Compound 17

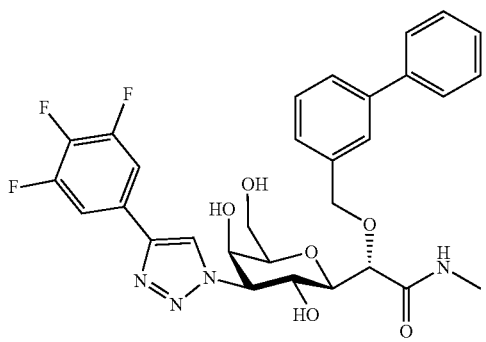

17

Compound 17 (4.3 mg, 29% over 2 steps) was prepared according to FIG. 2A.

¹H NMR (400 MHz, DMSO-d₆) δ 8.69 (s, 1H), 7.87-7.76 (m, 4H), 7.76-7.72 (m, 2H), 7.67-7.59 (m, 1H), 7.51-7.42 (m, 4H), 7.37-7.31 (m, 1H), 5.43 (d, J=8.0 Hz, 1H), 5.30 (d, J=5.8 Hz, 1H), 4.84 (dd, =10.7, 2.9 Hz, 1H), 4.73 (d, J=11.4 Hz, 1H), 4.64 (d, J 11.5 Hz, 1H), 4.55 (t, J=5.6 Hz, 1H), 4.42 (q, J=9.4 Hz, 1H), 4.20 (d, J=1.7 Hz, 1H), 3.97 (dd, J=6.1, 2.9 Hz, 1H), 3.72 (dd, J=9.4, 1.7 Hz, 1H), 3.59-3.45 (m, 2H), 3.45-3.38 (m, 1H), 2.65 (d, J=4.6 Hz, 3H). LCMS (ESI): m/z (M+Na) calculated for $C_{30}H_{29}F_3N_4O_6Na$: 621.56, found 621.1.

Example 5

Synthesis of Compound 18

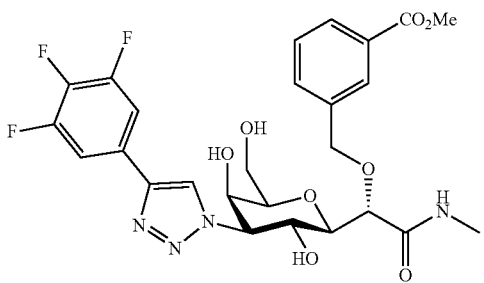

Compound 18 (5.6 mg, 51% over 2 steps) was prepared according to FIG. 2A.

¹H NMR (400 MHz, DMSO-d₆) δ 8.71 (s, 1H), 8.12 (d, J=1.8 Hz, 1H), 7.97-7.86 (m, 3H), 7.84-7.74 (m, 2H), 7.55 (t, J=7.7 Hz, 1H), 5.45 (d, J=7.9 Hz, 1H), 5.24 (d, J=5.9 Hz, 1H), 4.84 (dd, 1=10.7, 2.9 Hz, 1H), 4.73 (d, J=11.5 Hz, 1H), 4.62-4.52 (m, 2H), 4.48-4.38 (m, 1H), 4.17 (d, J=1.8 Hz, 1H), 3.95 (dd, J=6.1, 3.0 Hz, 1H), 3.89 (s, 3H), 3.70 (dd, J=9.4, 1.8 Hz, 1H), 3.57-3.45 (m, 2H), 3.43-3.38 (m, 1H), 2.65 (d, J=4.7 Hz, 3H). LCMS (ESI): m/z (M+Na) calculated for $C_{26}H_{27}F_3N_4O_8Na$: 603.50, found 603.2.

Example 6

Synthesis of Compound 19

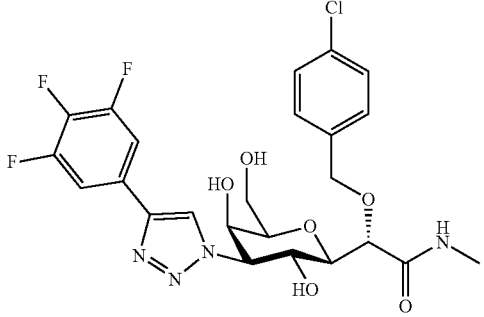

Compound 19 (8.8 mg, 81% over 2 steps) was prepared according to FIG. 2A.

¹H NMR (400 MHz, DMSO-d₆) δ 8.75 (s, 1H), 7.90 (dd, J=9.1, 6.7 Hz, 2H), 7.73 (q, J=4.7 Hz, 1H), 7.52 (d, J=8.5 Hz, 2H), 7.48-7.41 (m, 2H), 5.41 (d, J=8.0 Hz, 1H), 5.25 (d, J=5.9 Hz, 1H), 4.81 (dd, J=10.7, 2.9 Hz, 1H), 4.62 (d, J=11.5 Hz, 1H), 4.57-4.51 (m, 2H), 4.33 (td, J=9.7, 7.8 Hz, 1H), 4.14 (d, J=1.7 Hz, 1H), 3.94 (dd, J=6.1, 3.0 Hz, 1H), 3.68 (dd, J=9.5, 1.7 Hz, 1H), 3.59-3.44 (m, 2H), 3.44-3.36 (m, 1H), 2.64 (d, J=4.7 Hz, 3H). LCMS (ESI): m/z (M+Na) calculated for $C_{24}H_{24}ClF_3N_4O_6Na$: 579.91, found 579.1.

Example 7

Synthesis of Compound 20

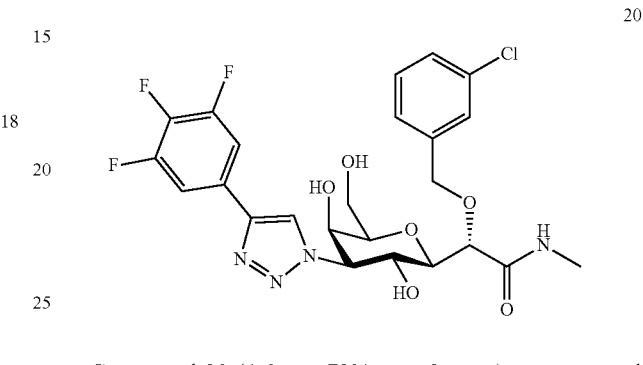

Compound 20 (4.6 mg, 72% over 2 steps) was prepared according to FIG. 2A.

¹H NMR (400 MHz, DMSO-d₆) δ 8.73 (s, 1H), 7.88 (dd, J=9.1, 6.6 Hz, 2H), 7.78 (q, J=4.6 Hz, 1H), 7.61 (s, 1H), 7.52-7.34 (m, 3H), 5.43 (d, J=7.9 Hz, 1H), 5.25 (d, J=5.9 Hz, 1H), 4.82 (dd, J=10.7, 2.9 Hz, 1H), 4.64 (d, J=11.7 Hz, 1H), 4.60-4.48 (m, 2H), 4.34 (q, J=9.3 Hz, 1H), 4.15 (d, J=1.7 Hz, 1H), 3.96 (dd, J=6.1, 2.9 Hz, 1H), 3.70 (dd, J=9.4, 1.8 Hz, 1H), 3.60-3.43 (m, 2H), 3.43-3.38 (n, 1H), 2.65 (d, J=4.7 Hz, 3H). LCMS (ESI): m/z (M+Na) calculated for $C_{24}H_{24}ClF_3N_4O_6Na$: 579.91, found 579.1.

Example 8

Synthesis of Compound 21

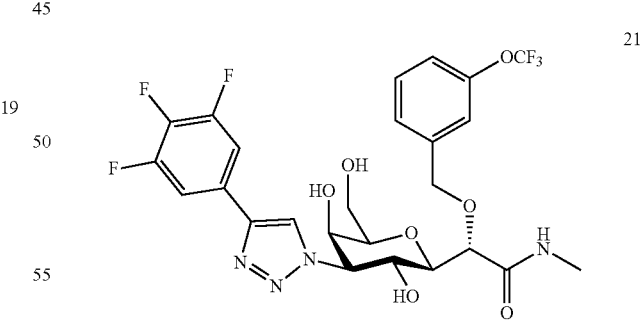

Compound 21 (4.9 mg, 98% over 2 steps) was prepared according to FIG. 2A.

¹H NMR (400 MHz, DMSO-d₆) δ 8.69 (s, 1H), 7.91-7.74 (m, 3H), 7.58-7.47 (m, 3H), 7.40-7.28 (m, 1H), 5.44 (d, J=7.9 Hz, 1H), 5.25 (d, J=5.9 Hz, 1H), 4.83 (dd, J=10.7, 2.9 Hz, 1H), 4.69 (d, J=11.8 Hz, 1H), 4.60 (d, J=11.8 Hz, 1H), 4.54 (t, J=5.5 Hz, 1H), 4.35 (q, J=9.4 Hz, 1H), 4.16 (d, J=1.7 Hz, 1H), 3.95 (dd, J=5.9, 2.9 Hz, 1H), 3.70 (dd, J=9.5, 1.8 Hz, 1H), 3.60-3.44 (m, 2H), 3.42-3.37 (m, 1H), 2.64 (d,

J=4.6 Hz, 3H). LCMS (ESI): m/z (M+Na) calculated for C$_{25}$H$_{24}$F$_6$N$_4$O$_7$Na: 629.46, found 629.1.

Example 9

Synthesis of Compound 24

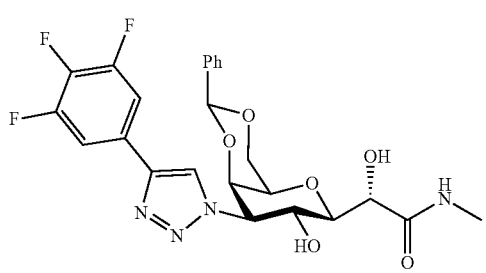

22

Compound 22: Compound 11 (0.12 g, 0.23 mmol) was dissolved in a solution of methyl amine (2 M THF, 12 mL, 24 mmol) in a screw-cap scintillation vial. The reaction mixture was stirred overnight at 76° C. The reaction mixture was concentrated and the residue was purified via flash chromatography (CH$_2$Cl$_2$ to 10% MeOH in CH$_2$Cl$_2$, gradient) to afford compound 22 (106 mg, 88%).

$^1$H NMR (400 MHz, DMSO-d$_6$) δ 8.85 (s, 1H), 7.93-7.83 (m, 3H), 7.38-7.32 (m, 5H), 5.60 (d, J=6.9 Hz, 1H), 5.51 (s, 1H), 5.36 (d, J=8.0 Hz, 1H), 5.11 (dd, J=10.8, 3.6 Hz, 1H), 4.50-4.35 (n, 2H), 4.32 (dd, J=6.9, 1.5 Hz, 1H), 4.07-3.95 (m, 2H), 3.87 (dd, J=9.4, 1.6 Hz, 1H), 3.73 (s, 1H), 2.66 (d, J=4.7 Hz, 3H). LCMS (ESI): m/z (M+Na) calculated for C$_{24}$H$_{23}$F$_3$N$_4$O$_6$Na: 543.45, found 543.1.

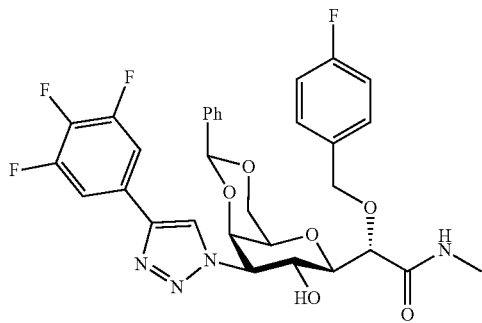

23

Compound 23: Compound 19 (10.3 mg, 0.02 mmol) was azeotroped with toluene 2 times under reduced pressure, then dried under high vacuum for 2+ hours. Compound 19 was then dissolved in 1 mL of anhydrous DMF and cooled to 0° C. in an ice-water bath under an atmosphere of argon. 4-fluorobenzyl bromide (2.4 uL, 0.019 mmol) dissolved in 0.1 mL anhydrous DMF was added to the reaction mixture and was allowed to stir at 0° C. for 30 minutes. NaH (0.8 mg, 0.02 mmol, 60%) was added, and the reaction was allowed to gradually warm to ambient temperature and stirred for 16 hours. The reaction was then diluted with EtOAc (30 mL), transferred to a separatory funnel, and washed with H$_2$O (15 mL). The aqueous phase was separated, and extracted with EtOAc (15 mL×2). The organic phases were pooled, subsequently washed with 1120 (3×15 mL), dried over Na$_2$SO$_4$, filtered, and concentrated under reduced pressure. Quick purification via silica gel flash chromatography (CH$_2$Cl$_2$ to 5% MeOH in CH$_2$Cl$_2$, gradient) was used to separate the product and unreacted starting material to afford compound 23 (5.8 mg, 47%). LCMS (ESI): m/z (M+Na) calculated for C$_{31}$H$_{28}$F$_4$N$_4$O$_6$Na: 651.56, found 651.2).

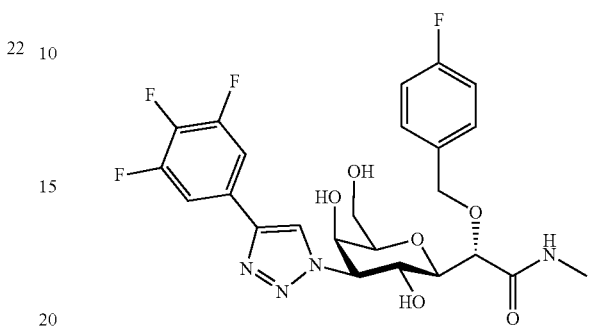

24

Compound 24: Compound 23 was dissolved in anhydrous MeOH (1.5 mL) and CSA (1 mg, 0.004 mmol) was added. The reaction mixture was stirred overnight at 78° C. in a screw-cap scintillation vial. The reaction mixture was concentrated and the residue was purified by flash chromatography (CH$_2$Cl$_2$ to 10% MeOH in CH$_2$Cl$_2$, gradient) to afford compound 24 (3.3 mg, 66%).

$^1$H NMR (400 MHz, DMSO-d$_6$) δ 8.69 (s, 1H), 7.84 (dd, J=9.1, 6.7 Hz, 21H), 7.64 (q, J=4.6 Hz, 1H), 7.51-7.40 (m, 2H), 7.14 (dd, J=10.0, 7.7 Hz, 2H), 5.35 (d, J=7.9 Hz, 1H), 5.19 (d, J=5.9 Hz, 1H), 4.74 (dd, J=10.7, 2.9 Hz, 1H), 4.57-4.42 (m, 3H), 4.26 (q, J=9.4 Hz, 1H), 4.06 (d, J=1.7 Hz, 1H), 3.87 (dd, J=5.9, 2.9 Hz, 1H), 3.60 (dd, J=9.5, 1.7 Hz, 1H), 3.51-3.36 (m, 2H), 3.36-3.30 (m, 1H), 2.56 (d, J=4.7 Hz, 3H). LCMS (ESI): m/z (M+Na) calculated for C$_{24}$H$_{24}$F$_4$N$_4$O$_6$Na: 563.45, found 563.45.

Example 10

Synthesis of Compound 25

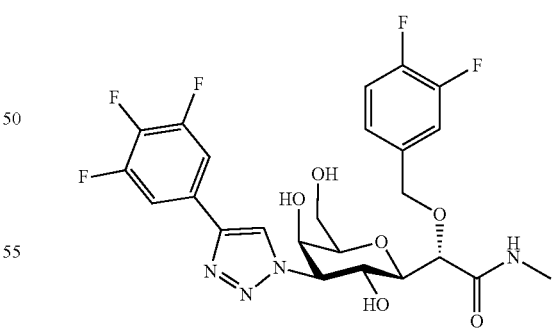

25

Figure 2B:
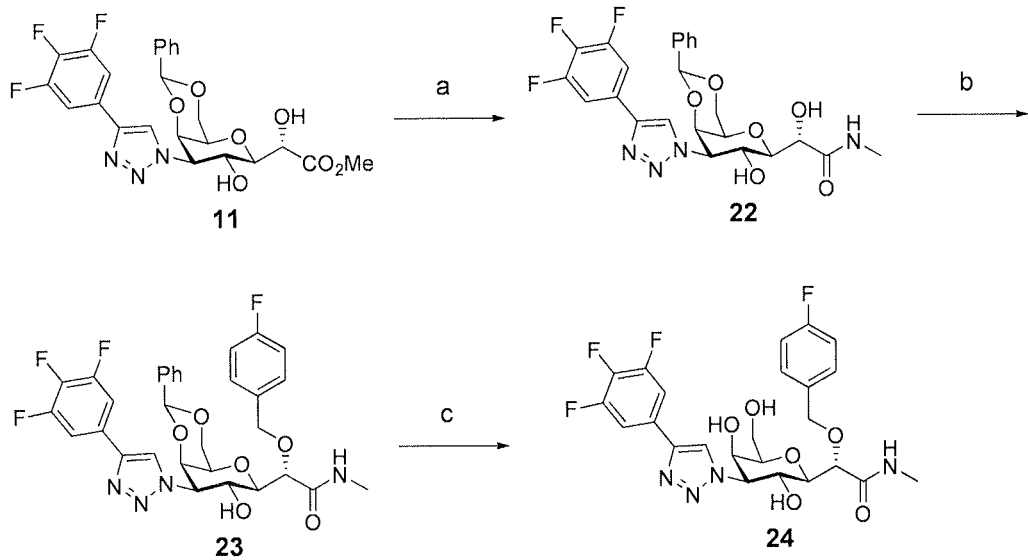
FIG. 2B is a diagram illustrating the synthesis of Compound 24.
Figure 3:
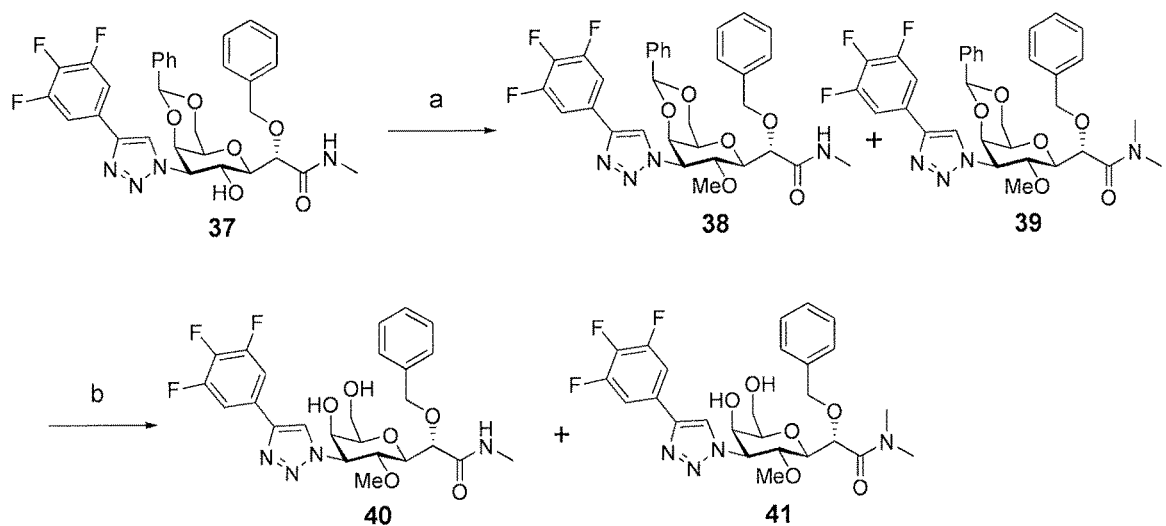
FIG. 3 is a diagram illustrating the synthesis of Compounds 40 and 41.
Figure 4:
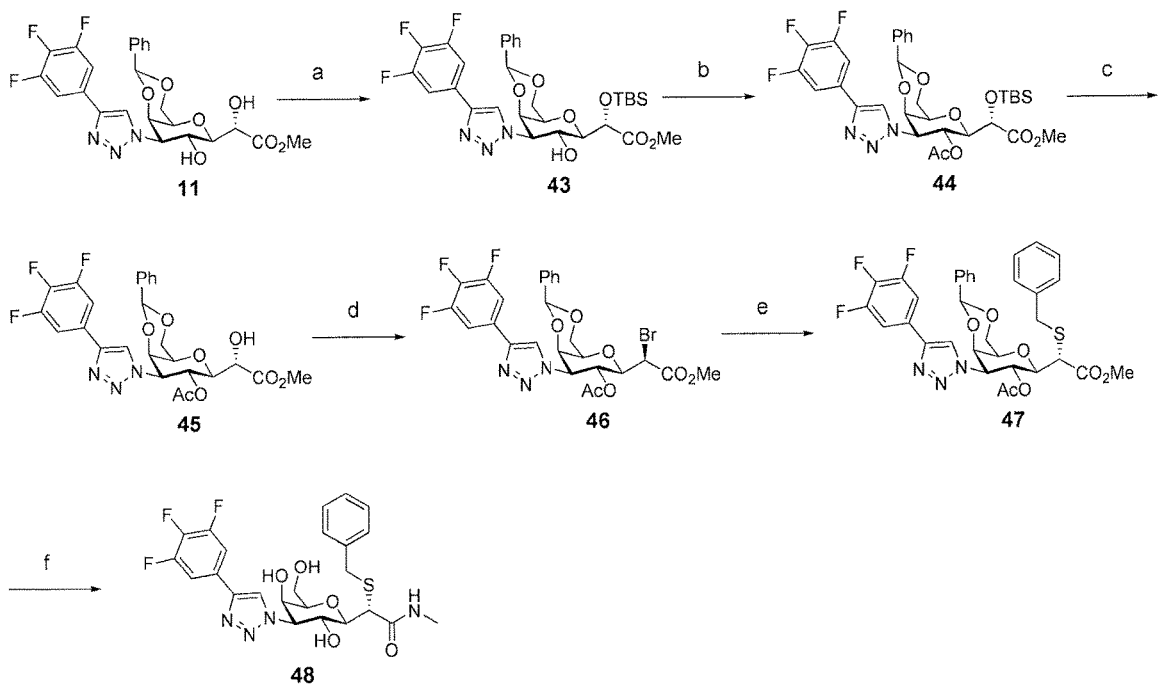
FIG. 4 is a diagram illustrating the synthesis of Compound 48.
Figure 5:
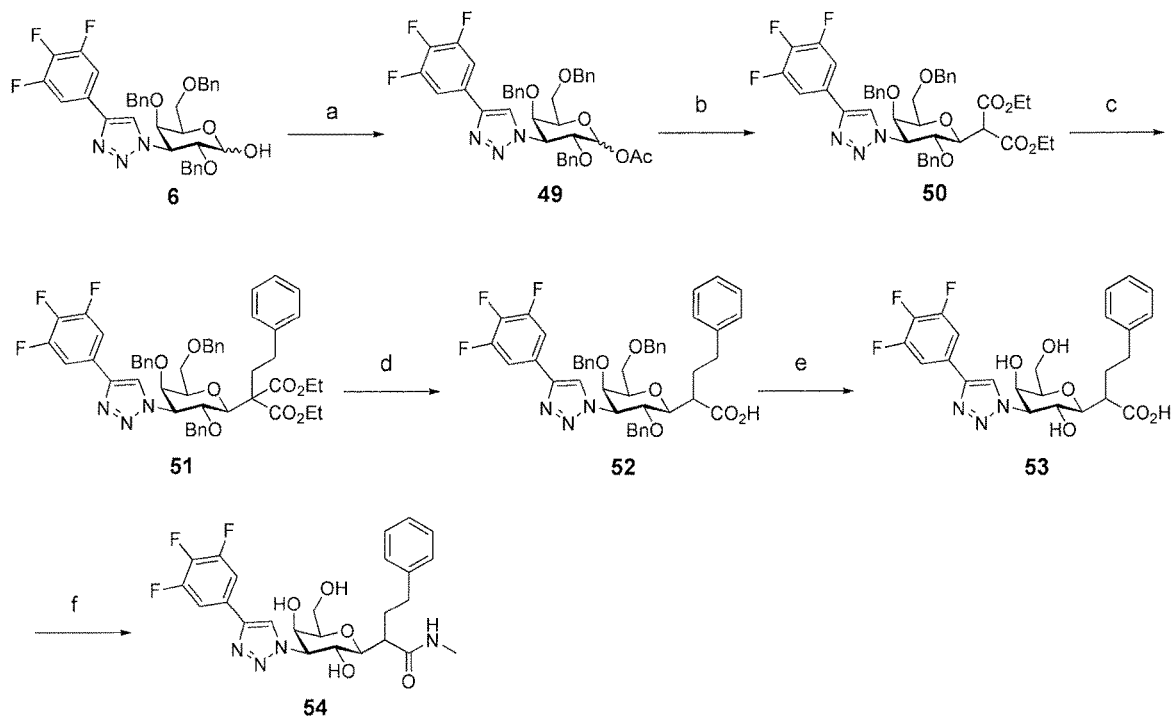
FIG. 5 is a diagram illustrating the synthesis of Compound 49.

Compound 25 (4.5 mg, 35%0 over three steps) was prepared according to FIG. 2B.

$^1$H NMR (400 MHz, DMSO-d$_6$) δ 8.68 (s, 1H), 7.81 (dd, J=9.0, 6.7 Hz, 2H), 7.70 (q, 1=4.6 Hz, 1H), 7.59-7.48 (m, 1H), 7.44-7.32 (m, 1H), 7.29-7.19 (m, 1H), 5.35 (d, J=7.9 Hz, 1H), 5.19 (d, J=5.9 Hz, 1H), 4.74 (dd, J=10.7, 2.9 Hz, 1H), 4.54 (d, J=11.6 Hz, 1H), 4.51-4.36 (m, 21H), 4.25 (q, J=9.4 Hz, 1H), 4.06 (d, J=17 Hz, 1H), 3.87 (dd, J=6.0, 2.9

Hz, 1H), 3.61 (dd, J=9.4, 1.8 Hz, 1H), 3.52-3.35 (m, 2H), 3.35-3.28 (m, 1H), 2.57 (d, J=4.6 Hz, 3H). LCMS (ESI): m/z (M+Na) calculated for $C_{24}H_{23}F_5N_4O_6Na$: 581.44, found 581.1.

Example 11

Synthesis of Compound 26

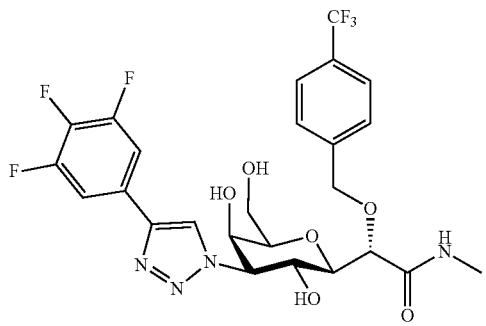

Compound 26 (4.7 mg, 36% over three steps) was prepared according to FIG. 2B.

$^1$H NMR (400 MHz, DMSO-$d_6$) δ 8.68 (s, 1H), 7.90-7.76 (m, 2H), 7.75-7.62 (m, 5H), 5.36 (d, J=7.8 Hz, 1H), 5.20 (d, J=5.9 Hz, 1H), 4.75 (dd, 1=10.7, 2.9 Hz, 1H), 4.67 (d, J=12.1 Hz, 1H), 4.56 (d, J=12.1 Hz, 1H), 4.47 (t, J=5.6 Hz, 1H), 4.28 (td, J=10.2, 7.9 Hz, 1H), 4.10 (d, J=1.7 Hz, 1H), 3.88 (dd, J=6.1, 2.9 Hz, 1H), 3.63 (dd, J=9.4, 1.8 Hz, 1H), 3.53-3.37 (m, 2H), 3.37-3.30 (m, 1H), 2.58 (d, J=4.6 Hz, 3H). LCMS (ESI): m/z (M+Na) calculated for $C_{25}H_{24}F_6N_4O_6Na$: 613.46, found 613.1.

Example 12

Synthesis of Compound 27

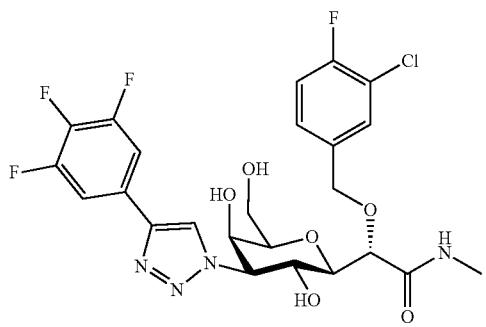

Compound 27 (3.3 mg, 32% over three steps) was prepared according to FIG. 2B.

$^1$H NMR (400 MHz, DMSO-$d_6$) δ 8.67 (s, 1H), 7.81 (dd, J=9.1, 6.7 Hz, 2H), 7.72 (q, J=4.6 Hz, 1H), 7.58-7.42 (m, 21H), 7.30-7.21 (m, 1H), 5.35 (d, J=7.9 Hz, 1H), 5.19 (d, J=5.9 Hz, 1H), 4.74 (dd, J=10.7, 2.9 Hz, 1H), 4.57 (d, J=11.9 Hz, 1H), 4.51-4.44 (m, 2H), 4.25 (q, J=9.5 Hz, 1H), 4.07 (d, J=1.7 Hz, 1H), 3.87 (dd, J=6.4, 3.0 Hz, 1H), 3.62 (dd, J=9.3, 1.8 Hz, 1H), 3.52-3.36 (m, 2H), 3.36-3.30 (m, 11H), 2.57 (d, J=4.7 Hz, 3H). LCMS (ESI): m/z (M+Na) calculated for $C_{21}H_{23}ClF_4N_4O_6Na$: 597.90, found 597.1.

Example 13

Synthesis of Compound 28

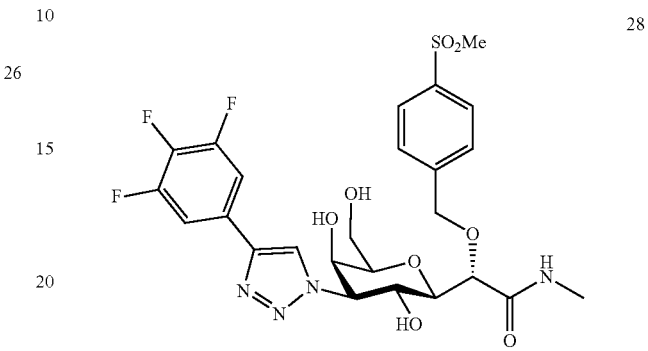

Compound 28 (3.8 mg, 29% over three steps) was prepared according to FIG. 2B.

$^1$H NMR (400 MHz, DMSO-$d_6$) δ 8.71 (s, 1H), 7.92-7.79 (m, 4H), 7.76-7.65 (ln, 3H), 5.39 (d, J=7.7 Hz, 1H), 5.21 (d, J=5.9 Hz, 1H), 4.76 (dd, J=10.7, 2.9 Hz, 1H), 4.69 (d, J=12.3 Hz, 1H), 4.58 (d, J=12.4 Hz, 1H), 4.49 (t, J=5.6 Hz, 1H), 4.29 (q, 1=9.4 Hz, 1H), 4.11 (d, J=1.7 Hz, 1H), 3.88 (dd, J=6.0, 2.9 Hz, 1H), 3.63 (dd, J=9.4, 1.8 Hz, 1H), 3.52-3.37 (m, 2H), 3.36-3.30 (m, 1H), 3.15 (s, 3H), 2.58 (d, J=4.6 Hz, 3H). LCMS (ESI): m/z (M+Na) calculated for $C_{25}H_{27}F_3N_4O_8SNa$: 623.55, found 623.0.

Example 14

Synthesis of Compound 29

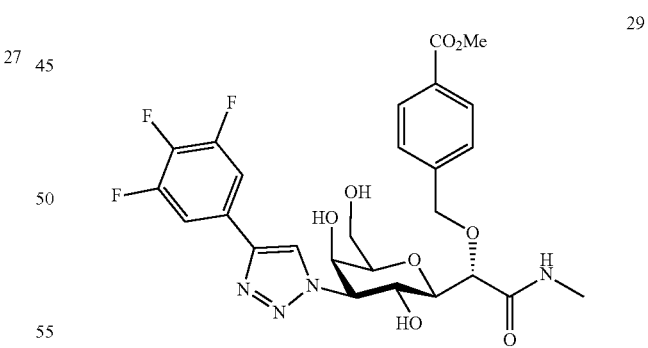

Compound 29 (3.4 mg, 26% over three steps) was prepared according to FIG. 2B.

$^1$H NMR (400 MHz, DMSO-$d_6$) δ 8.69 (s, 1H), 7.95-7.89 (m, 2H), 7.88-7.78 (m, 2H), 7.69 (q, J=4.8 Hz, 1H), 7.56 (d, J=8.1 Hz, 2H), 5.37 (d, J=7.8 Hz, 1H), 5.22 (d, J=5.9 Hz, 1H), 4.75 (dd, J=10.7, 2.9 Hz, 1H), 4.65 (d, J=12.3 Hz, 1H), 4.55 (d, J=: 12.2 Hz, 1H), 4.49 (t, 1=5.6 Hz, 1H), 4.29 (td, 1=10.0, 7.6 Hz, 1H), 4.10 (d, J=1.8 Hz, 1H), 3.87 (dd, J=6.1, 2.9 Hz, 1H), 3.79 (s, 3H), 3.62 (dd, J=9.4, 1.8 Hz, 1H), 3.53-3.38 (m, 2H), 3.35-3.28 (m, 1H), 2.58 (d, J=4.7 Hz,

Example 15

Synthesis of Compound 30

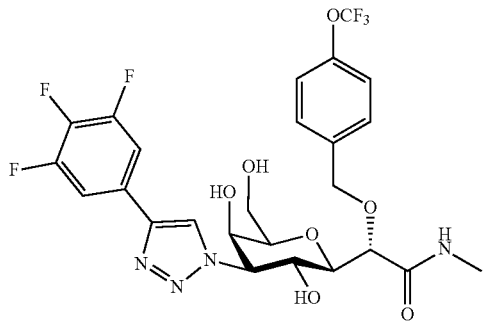

Compound 30 (2.8 mg, 20%0 over three steps) was prepared according to FIG. 2B.

$^1$H NMR (400 MHz, DMSO-$d_6$) δ 8.76 (s, 1H), 7.90 (dd, J=9.1, 6.7 Hz, 2H), 7.74 (q, J=4.7 Hz, 1H), 7.66-7.58 (m, 2H), 7.39 (d, J=8.1 Hz, 2H), 5.44 (d, J=7.9 Hz, 1H), 5.27 (d, J=5.9 Hz, 1H), 4.83 (dd, J=10.7, 2.9 Hz, 1H), 4.66 (d, J=11.6 Hz, 1H), 4.62-4.53 (m, 2H), 4.35 (q. J=9.4 Hz, 1H), 4.16 (d, J=1.7 Hz, 1H), 3.95 (dd, J=5.9, 0.9 Hz, 1H), 3.69 (dd, J=9.4, 1.8 Hz, 1H), 3.58-3.44 (m, 2H), 3.44-3.37 (n, 1H), 2.64 (d, J=4.7 Hz, 3H). LCMS (ESI): m/z (M+Na) calculated for $C_{25}H_{24}F_6N_4O_7Na$: 629.46, found 629.1.

Example 16

Synthesis of Compound 31

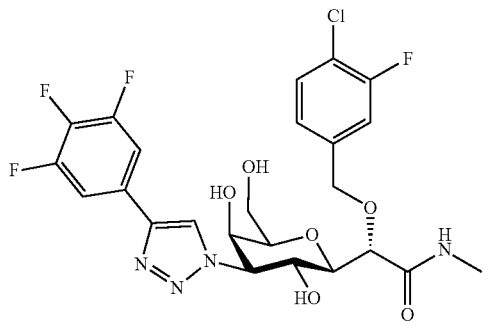

Compound 31 (1.3 mg, 11% over three steps) was prepared according to FIG. 2B.

$^1$H NMR (400 MHz, DMSO-$d_6$) δ 8.74 (s, 1H), 7.88 (dd J=9.1, 6.7 Hz, 2H), 7.81 (q, J=4.6 Hz, 1H), 7.76 (dd, J=7.4, 2.1 Hz, 1H), 7.56-7.46 (in, 1H), 7.46-7.37 (in, 1H), 5.44 (d, J=7.9 Hz, 1H), 5.27 (d, J=5.9 Hz, 1H), 4.81 (dd, J=10.6, 2.9 Hz, 1H), 4.61 (d, J=11.5 Hz, 1H), 4.58-4.49 (m, 2H), 4.31 (q, J=9.2 Hz, 1H), 4.12 (d, J=1.7 Hz, 1H), 3.98-3.92 (m, 1H), 3.68 (dd, J=9.5, 1.8 Hz, 1H), 3.59-3.44 (m, 2H), 3.42-3.37 (m, 1H), 2.64 (d, J=4.7 Hz, 3H). LCMS (ESI): m/z (M+Na) calculated for $C_{24}H_{23}ClF_4N_4O_6Na$: 597.90, found 597.0.

Example 17

Synthesis of Compound 32

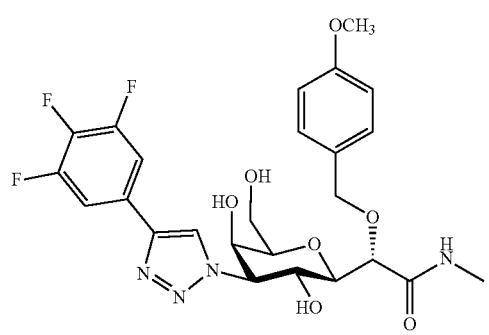

Compound 32 (1.5 ng, 12% over three steps) was prepared according to FIG. 2B.

$^1$H NMR (400 MHz, CD$_3$OD) δ 8.40 (s, 1H), 7.57 (dd, J=8.7, 6.5 Hz, 2H), 7.33-7.25 (m, 2H), 6.88-6.78 (m, 2H), 4.73 (dd, J=10.8, 3.0 Hz, 1H), 4.57-4.47 (m, 3H), 4.37 (t, J=10.1 Hz, 1H), 4.20 (d, J=1.8 Hz, H), 3.99 (d, J=2.9 Hz, 1H), 3.69 (s, 3H), 363 (dd, J=9.4, 1.9 Hz, 1H), 3.55 (s, 3H), 2.67 (s, 3H). LCMS (ESI): m/z (M+Na) calculated for $C_{25}H_{27}F_3N_4ONa$: 575.49, found 575.1.

Example 18

Synthesis of Compound 33

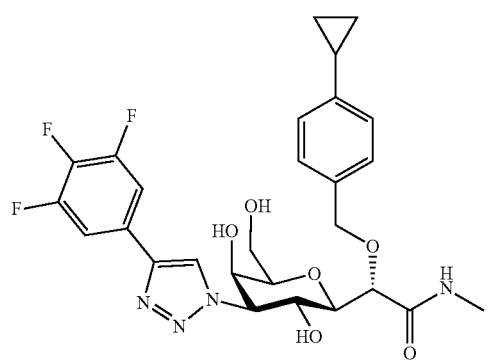

Compound 33 (2.3 mg, 21% over three steps) was prepared according to FIG. 2B.

$^1$H NMR (400 MHz, DMSO-d6) δ 8.76 (s, 1H), 7.90 (dd, J=9.1, 6.7 Hz, 2H), 7.63 (d, J=5.1 Hz, 1H), 7.34 (d, J=7.9 Hz, 2H), 7.07 (d, J=8.0 Hz, 2H), 5.38 (d, J=7.9 Hz, 1H), 5.26 (d, J=5.8 Hz, 1H), 4.80 (dd, J=10.7, 2.9 Hz, 1H), 4.53 (dd, J=10.2, 4.9 Hz, 3H), 4.32 (q, J=9.4 Hz, 1H), 4.11 (s, 1H), 3.93 (s, 1H), 3.69-3.58 (m, 1H), 3.54-3.41 (m, 3H), 2.62 (d, J=4.7 Hz, 3H), 1.91 (tt, J=8.7, 5.0 Hz, 1H), 0.99-0.90 (m, 2H), 0.65 (dt, J=6.6, 3.3 Hz, 2H). LC-MS m/z=563.2 (M+1).

Example 19

Synthesis of Compound 34

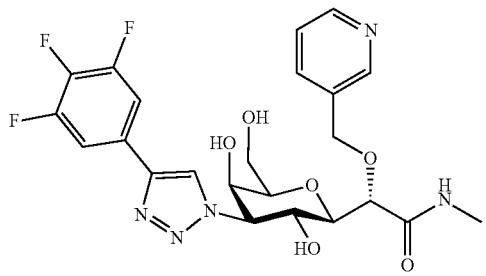

Compound 34 (2.1 mg, 19% over three steps) was prepared according to FIG. 2B.

$^1$H NMR (400 MHz, DMSO-d6) δ 8.77 (s, 1H), 8.68 (s, 1H), 8.54 (dd, J=4.8, 1.7 Hz, 1H), 7.91 (t, J=8.3 Hz, 3H), 7.78 (d, J=5.1 Hz, 1H), 7.43 (dd, J=7.8, 4.8 Hz, 1H), 5.47 (d, J=7.8 Hz, 1H), 5.27 (d, J=5.9 Hz, 1H), 4.82 (dd, J=10.9, 2.8 Hz, 1H), 4.71-4.52 (m, 3H), 4.34 (q, J=9.4 Hz, 1H), 4.17 (s, 1H), 3.94 (d, J=5.5 Hz, 1H), 3.69 (d, J=9.4 Hz, 1H), 3.59-3.41 (m, 3H), 2.64 (d, J=5.1 Hz, 3H).

Example 20

Synthesis of Compound 24

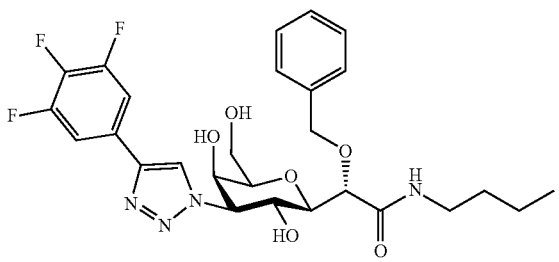

Compound 35 (2.1 mg, 1900 over three steps) was prepared according to FIG. 2B.

$^1$H NMR (400 Hz, DMSO-d6) δ 8.69 (s, 1H), 7.89 (dd, J=9.1, 6.7 Hz, 2H), 7.53 (t, 1H), 7.44 (d, J=7.6 Hz, 2H), 7.41-7.35 (m, 2H), 7.32 (d, J=7.0 Hz, 1H), 5.16 (t, J=6.1 Hz, 2H), 4.78 (dd, J=10.6, 2.8 Hz, 1H), 4.65 (d, J=4.1 Hz, 2H), 4.60 (t, J=5.8 Hz, 1H), 4.45 (q, J=9.7 Hz, 1H), 3.93 (t, J=3.5 Hz, 1H), 3.78 (d, J=9.3 Hz, 1H), 3.63 (t, 1H), 3.50 (t, J=5.9 Hz, 3H), 1.37 (dt, J=12.7, 6.4 Hz, 2H), 1.31-1.18 (m, 4H), 0.84 (t, J=7.3 Hz, 3H). LC-MS m/z=565.2 (M+1).

Example 21

Synthesis of Compound 36

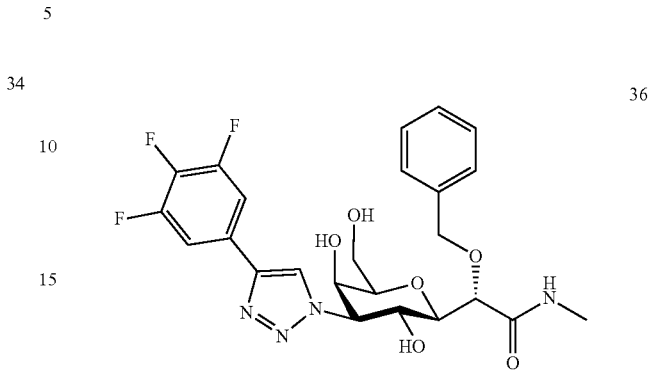

Compound 36 (2.1 mg, 19% over three steps) was prepared according to FIG. 2B.

$^1$H NMR (400 MHz, Methanol-d$_4$) δ 8.51 (s, 11H), 7.71-7.59 (m, 2H), 7.53-7.43 (m, 2H), 7.43-7.30 (m, 3H), 4.84 (dd, J=10.8, 3.0 Hz, 1H), 4.67 (s, 2H), 4.52 (dd, J=10.7, 9.4 Hz, 1H), 4.33 (d, J=1.9 Hz, 1H), 4.10 (d, J=2.9 Hz, 1H), 3.75 (dd, J=9.4, 2.0 Hz, 1H), 3.67 (s, 3H). LCMS (ESI): m/z calculated for $C_{24}H_{25}F_3N_4O_6$: 522.2, found 523.2 (M+1).

Example 22

Synthesis of Compounds 40 and 41

Compounds 38 and 39: Compound 37 (95 mg, 0.16 mmoles, prepared according to FIG. 2B) and iodomethane (24 mg, 0.17 mmoles) were dissolved in DMF (2.0 mL) and cooled on an ice bath. Sodium hydride (60%, 7 mg, 0.17 mmoles) was added and the mixture was stirred for 30 minutes on the ice bath and subsequently for 30 minutes at room temperature. The reaction mixture was diluted with ethyl acetate, transferred to a separatory funnel and washed 3 times with water. The organic phase was concentrated and separated by flash chromatography to afford an inseparable mixture of compounds 38 and 39 (54 mg).

Compound 38: LCMS (ESI): m/z calculated for $C_{32}H_{31}F_3N_4O_6$: 624.2, found 625.2 (M+1); 647.2 (M+Na).

Compound 39: LCMS (ESI): m/z calculated for $C_{33}H_{33}F_3N_4O_6$: 638.2, found 639.2 (M+1); 661.2 (M+Na).

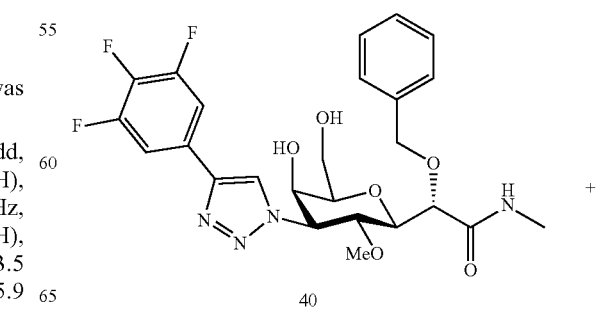

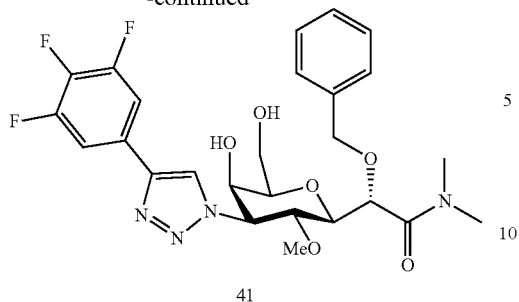

41

Compounds 40 and 41: A mixture of compounds 38 and 39 (71 mg) and CSA (6 mg) were dissolved in methanol (2 mL) and heated at 70° C. for 2. The reaction mixture was cooled to room temperature, neutralized with basic resin, filtered and concentrated. The residue was purified by flash chromatography to obtain 40 (34 mg) and 41 (17 mg) as separate solids.

Compound 40: $^1$H NMR (400 MHz, Methanol-d4) δ 8.67 (s, 1H), 7.68 (dd, J=8.8, 6.6 Hz, 2H), 7.48 (d, J=7.0 Hz, 2H), 7.44-7.29 (m, 3H), 4.87 (1H, overlapping with solvent peak), 4.74 (d, J=11.4 Hz, 1H), 4.49 (d, J=11.4 Hz, 1H), 4.30-4.16 (m, 2H), 4.05 (d, J=2.9 Hz, 1H), 3.77-3.60 (m, 4H), 2.87 (s, 3H), 2.81 (s, 3H). LC MS (ESI): m/z calculated for $C_{25}H_{27}F_3N_4O_6$: 536.2, found 537.2 (M+1).

Compound 41: $^1$H NMR (400 MHz, DMSO-d6) δ 8.99 (s, 1H), 7.88 (dd, J=9.0, 6.7 Hz, 2H), 7.44-7.31 (m, 5H), 5.42 (d, J=6.0 Hz, 1H), 5.01 (dd, J=10.7, 2.9 Hz, 1H), 4.65-4.50 (m, 2H), 4.48-4.34 (m, 2H), 4.11 (dd, J=10.6, 9.3 Hz, 1H), 3.88 (dd, J=6.2, 2.9 Hz, 1H), 3.73 (dd, J=93, 2.5 Hz, 1H), 3.63 (t, J=6.4 Hz, 1H), 3.50 (dt, J=12.5, 6.4 Hz, 1H), 3.41 (dt, J=10.9, 5.5 Hz, 1H), 3.15 (s, 3H), 2.96 (s, 3H), 2.87 (s, 3H). LCMS (ESI): m/z calculated for $C_{26}H_{29}F_3N_4O_6$: 550.2, found 551.2 (M+1).

Example 23

Synthesis of Compound 42

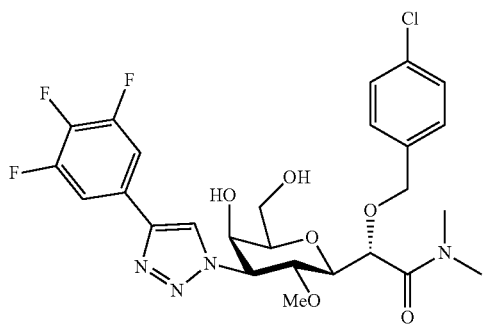

42

Compound 42: Compound 42 was prepared according to FIG. 3.

$^1$H NMR (400 MHz, Methanol-d4) δ 8.73 (s, 1H), 7.68 (dd, J=8.7, 6.6 Hz, 2H), 7.47 (d, J=8.5 Hz, 2H), 7.42-7.35 (m, 2H), 4.92 (1H, overlapping with solvent peak), 4.67 (dd, J=6.8, 4.5 Hz, 2H), 4.45 (d, J=11.3 Hz, 1H), 4.25 (dd, J=10.6, 9.3 Hz, 1H), 4.04 (d, J=2.9 Hz, 1H), 3.75 (ddd, J=8.6, 6.0, 3.2 Hz, 2H), 3.72-3.63 (m, 2H), 3.19 (s, 3H), 3.01 (s, 3H), 2.98 (s, 3H). LCMS (ESI): m/z calculated for $C_{28}H_{28}ClF_3N_4O_6$: 584.2, found 585.1 (M+1).

Example 24

Prophetic Synthesis of Compound 48

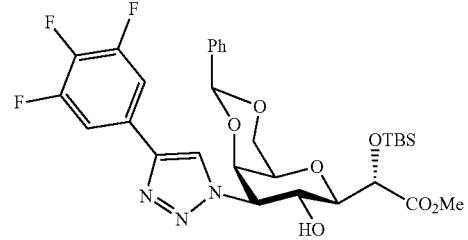

43

Compound 43: Compound 11 is dissolved in DMF and cooled on an ice bath. Imidazole (1.1 eq) is added followed by TBSCl (1.1 eq). The reaction mixture is stirred until completion. The reaction mixture is diluted with ethyl acetate, transferred to a separatory funnel and washed 3 times with water. The organic phase is dried over sodium sulfate, filtered, and concentrated. The residue is separated by flash chromatography to afford compound 43.

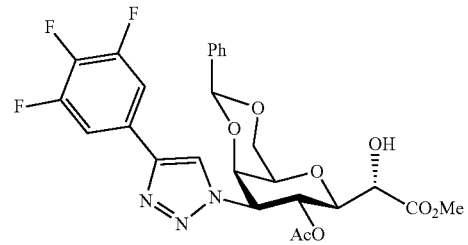

44

Compound 44: Compound 43 is dissolved in pyridine and cooled on an ice bath. Acetic anhydride (2 eq) is added and the reaction mixture is stirred until completion. The reaction mixture is diluted with ethyl acetate, transferred to a separatory funnel and washed 3 times with water. The organic phase is dried over sodium sulfate, filtered, and concentrated. The residue is separated by flash chromatography to afford compound 44.

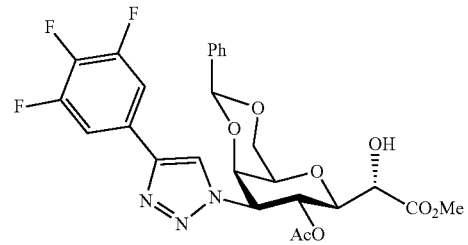

45

Compound 45: Compound 44 is dissolved in THF and cooled on an ice bath. Tetrabutylammonium fluoride (1.1 eq) is added and the reaction mixture is stirred until completion. The reaction mixture is diluted with ethyl acetate, transferred to a separatory funnel and washed 3 times with water. The organic phase is dried over magnesium sulfate, filtered, and concentrated. The residue is separated by flash chromatography to afford compound 45.

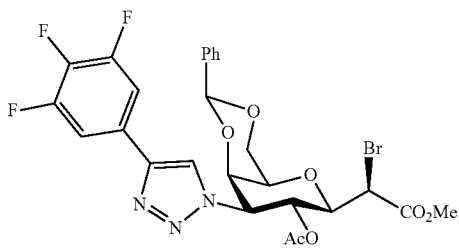

46

Compound 46: Compound 45 is dissolved in DCM and cooled on an ice bath Thionyl bromide (1.1 eq) is added and the reaction mixture is stirred until completion. The reaction mixture is quenched by the addition of saturated aqueous sodium bicarbonate solution. The reaction mixture is transferred to a separatory funnel and extracted 3 times with ethyl acetate. The combined organic phases are dried over sodium sulfate, filtered and concentrated. The residue is separated by flash chromatography to afford compound 46.

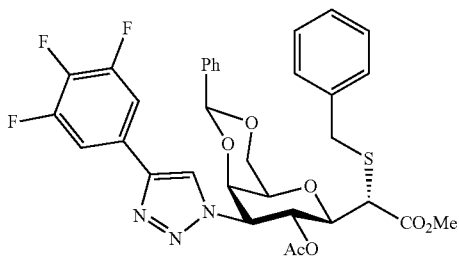

47

Compound 47: Benzyl thiol is dissolved in DMF and cooled on an ice bath. Sodium hydride (1.0 eq) is added and the reaction mixture is stirred for 30 minutes. Compound 46 (0.9 eq) dissolved in DMF is added. The reaction mixture is stirred until completion. The reaction mixture is quenched by the addition of saturated aqueous ammonium chloride solution. The reaction mixture is transferred to a separatory funnel and extracted 3 times with ethyl acetate. The combined organic phases are dried over sodium sulfate, filtered and concentrated. The residue is separated by flash chromatography to afford compound 47.

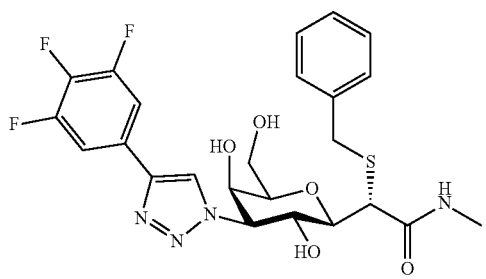

48

Compound 48: Compound 47 is dissolved in a solution of methylamine (2 M THF) and refluxed overnight. The reaction mixture is concentrated and the residue is dissolved in MeOH containing a catalytic amount of CSA. The reaction mixture is refluxed overnight. The reaction mixture is concentrated and purified by flash chromatography to afford compound 48.

Example 25

Prophetic Synthesis of Compound 53

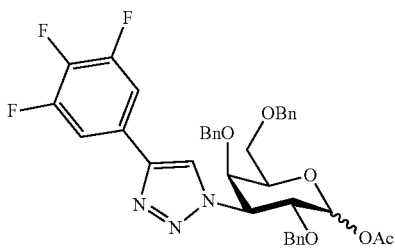

49

Compound 49: Compound 6 is dissolved in pyridine and cooled on an ice bath. Acetic anhydride (2 eq) is added and the reaction mixture is stirred until completion. The reaction mixture is diluted with ethyl acetate, transferred to a separatory funnel and washed 3 times with water. The organic phase is dried over sodium sulfate, filtered, and concentrated. The residue is separated by flash chromatography to afford compound 49.

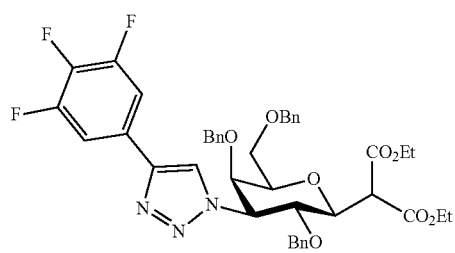

50

Compound 50: Compound 49 is dissolved in DCM and cooled on an ice bath. Trimethylsilyl iodide (1.1 eq) is added and the reaction mixture is stirred until completion. The solvent is removed in vacuo and the residue is dissolved in THF. In a separate flask diethyl malonate is dissolved in THF and NaHMDS (0.9 eq) and 0.15-crown-5 (0.9 eq) are added. After stirring for 30 minutes the glycosyl iodide solution is added and the reaction mixture is stirred until completion. The solvent is removed and the residue is purified by flash chromatography to afford compound 50.

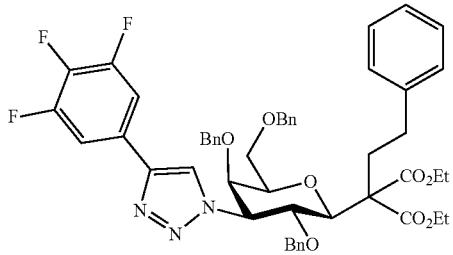

51

Compound 51: Compound 50 is dissolved in DMF and cooled on an ice bath. Sodium hydride (1.1 eq) is added and the mixture stirred for 30 minutes. Phenethyl bromide (1.1 eq) is added and the reaction is warmed to room temperature and stirred until completion. The reaction mixture is quenched by the addition of aqueous saturated ammonium chloride solution, transferred to a separatory funnel and extracted 3 times with ether. The combined organic phases are dried over magnesium sulfate, filtered, and concentrated. The residue is purified by flash chromatography to afford compound 51.

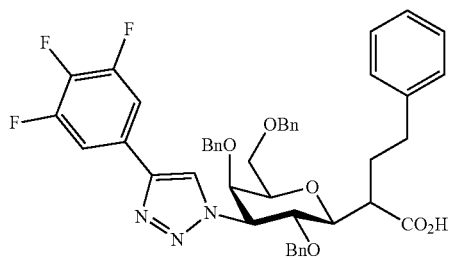

52

Compound 52: Compound 51 is dissolved in methanol. Sodium hydroxide (5 eq of a 1M aqueous solution) is added and the reaction mixture is stirred at room temperature until completion. A large excess of acetic acid is added and the reaction mixture is stirred at 100° C. until completion. The solvent is removed and the residue is purified by flash chromatography to afford compound 52.

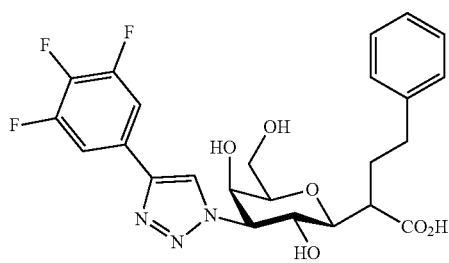

53

Compound 53: To a solution of compound 52 dissolved in methanol is added Pd/C. The reaction mixture is hydrogenated on a Paar shaker until completion. The reaction mixture is filtered through Celite and concentrated to afford compound 53.

Example 26

Prophetic Synthesis of Compound 54

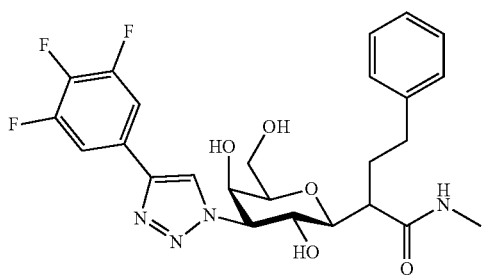

54

Compound 54: Compound 53 is dissolved in DMF and cooled on an ice bath. Diisopropylethylamine (1.5 eq) is added followed by HATU. The reaction mixture is stirred 15 minutes and then methylamine (2 M THF solution, 1.2 eq) is added. The ice bath is removed and the reaction mixture is stirred at room temperature overnight. The reaction mixture is concentrated and the residue is purified by flash chromatography to afford compound 54.

Example 27

Synthesis of Compound 69

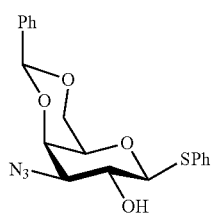

55

Compound 55: Compound 3, benzaldehyde dimethyl acetal, and camphorsulfonic acid were dissolved in acetonitrile at room temperature. The reaction mixture was stirred for 5 hours then quenched by addition of triethylamine. The reaction mixture was concentrated then separated by column chromatography to afford compound 55. MS (ESI): m/z calculated for $C_{19}H_{19}N_3O_4S$: 385.1, found 408.1 (M+Na).

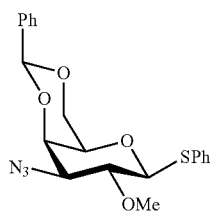

56

Compound 56: Compound 55 (663 mg, 1.72 mmol) was dissolved in 10 mL DMF under Ar and cooled on an ice bath. Sodium hydride (90 mg, 2.23 mmol, 1.3 eq, 60% oil dispersion) was added. Reaction mixture stirred 20 minutes on ice bath. Methyl iodide (0.21 mL, 3.44 mmol, 2 eq) was added and the reaction mixture was stirred overnight allowing to warm to room temperature. The reaction mixture was quenched by the addition of saturated NH$_4$Cl, diluted with ethyl acetate, and transferred to a separatory funnel. The phases were separated and the organic phase was washed 2× with water and 1× with brine. The organic phase was dried over Na$_2$SO$_4$, filtered and concentrated. The residue was purified by flash chromatography to afford 678 mg compound 56 (99% yield). MS (ESI): m/z calculated for C$_{20}$H$_{21}$N$_3$O$_4$S: 399.1, found 422.1 (M+Na).

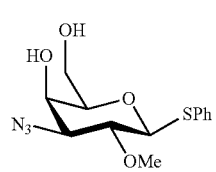

57

Compound 57: Compound 56 (678 mg, 1.93 mmol) was dissolved in 5 mL MeOH. HCl (0.5 mL of a 3M aqueous solution) was added and the reaction mixture was stirred at 70° C. for 30 minutes. The reaction mixture was concentrated. The residue was purified by flash chromatography to afford 473 mg compound 57 (90% yield). MS (ESI): m/z calculated for C$_{13}$H$_{17}$N$_3$O$_4$S: 311.1, found 324.1 (M+Na).

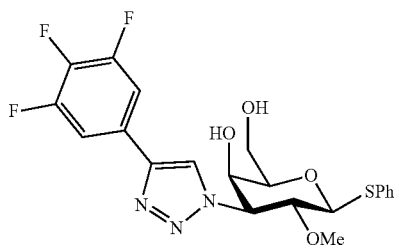

58

Compound 58: Compound 57 (809 mg, 2.60 mmoles), 3,4,5-trifluorophenyl-1-acetylene (2.5 equiv), THPTA (0.11 equiv), copper sulfate (0.1) were combined in methanol (15 mL). Sodium ascorbate (2.4 equiv) dissolved in minimum amount of water was added. The reaction mixture was stirred at room temperature overnight. The resultant precipitate was collected by filtration, washed with hexanes and water, and dried to give 1.2 g of compound 58 as a pale yellow solid (99% yield).

MS (ESI): m/z calculated for C$_{21}$H$_{20}$F$_3$N$_3$O$_4$S: 467.1, found 490.1 (M+Na).

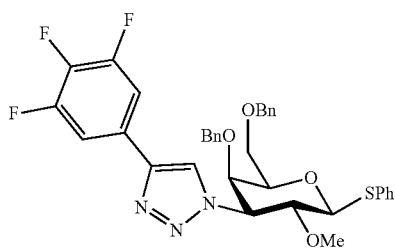

59

Compound 59: Compound 58 (1.2 g, 2.65 mmoles) was dissolved in DMF (15 mL) and cooled on an ice bath. Sodium hydride (60%, 477 mg, 11.93 mmoles) was added and the mixture was stirred for 30 minutes on the ice bath. Benzyl bromide (1.42 mL, 11.93 mmoles) was added and the reaction was warmed to room temperature and stirred overnight. The reaction mixture was diluted with ethyl acetate and transferred to a separatory funnel. The organic phase was washed with saturated NH$_4$Cl then water. The organic phase was concentrated and purified by flash chromatography to afford 1.8 g of compound 59 (94%

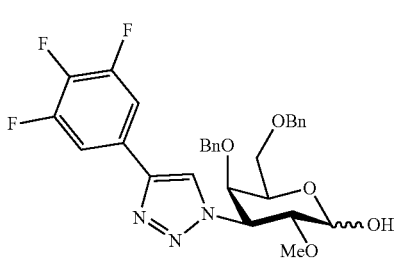

60

Compound 60: Compound 59 (1.8 g, 2.49) was dissolved in acetone (20 mL) and water (2 mL) and cooled to 0° C. Trichloroisocyanuric acid (637 mg, 2.74 mmoles) was added and the mixture was stirred at 0° C. for 3 h. The acetone was removed in vacuo. The resulting aqueous suspension was extracted with dichlororethane. The organic phase was washed with saturated NaHCO$_3$ then concentrated. The residue was purified by flash chromatography to afford 1.5 g of compound 60 (95% yield).

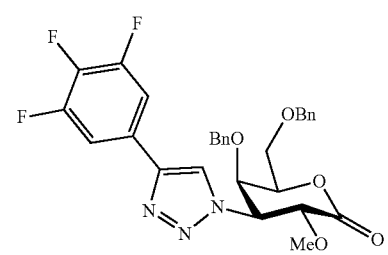

61

Compound 61: Compound 60 (1.0 g, 1.58 mmoles) was dissolved in dichloromethane (20 mL) and cooled on an ice bath. Dess-Martin periodinane (1.0 g, 2.37 mmoles) was added and the reaction mixture was allowed to warm to room temperature and stirred overnight. The reaction mixture was quenched by the addition of saturated NaHCO$_3$. The organic phase was concentrated and separated by column chromatography to afford compound 61 (520 mg, 52%/0 yield).

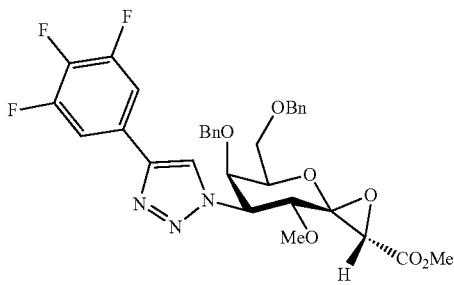

62

Compound 62: Methyl bromoacetate (253 mg, 1.65 mmoles dissolved in 0.5 mL of THF) was added dropwise to a solution of lithium bis-trimethylsilylamide (1.0 M in THF, 1.65 mL, 1.65 mmoles) cooled at −78° C. The reaction mixture stirred at −78° C. for 30 min. Compound 61 (260 mg, 0.41 mmoles dissolved in 2.0 mL of THF 2.0 mL) was added dropwise. The reaction mixture was stirred at −78° C. for 30 minutes. The reaction was quenched by the addition of saturated NH$_4$Cl and warmed to room temperature. The reaction mixture was transferred to a separatory funnel and extracted with ethyl acetate. The organic phase was concentrated and separated by flash chromatography to afford 183 mg of compound 62 (640 yield).

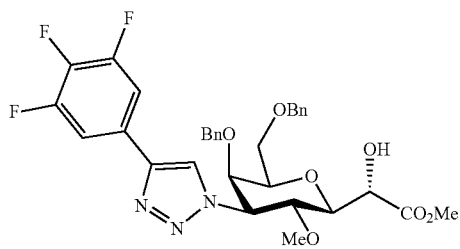

63

Compound 63: Compound 62 (980 mg, 1.57 mmol) was azeotroped with toluene two times under reduced pressure, and then dried under high vacuum for 2 hours. It was then dissolved in anhydrous CH$_2$Cl$_2$ (15 mL) and cooled on an ice/acetone bath while stirring under an atmosphere of argon. Triethylsilane (0.9 mL, 4.7 mmol) was added dropwise and the solution was allowed to stir for 5 minutes on the ice bath. Triethylsilyl triflate (1.0 mL, 6.3 mmol) was then added dropwise over the course of 5 minutes. The reaction was slowly warmed to 0° C. and stirred for 3 hours. The reaction mixture was then diluted with CH$_2$Cl$_2$ (10 mL), transferred to a separatory funnel, and washed with saturated aqueous NaHCO$_3$ (20 mL). The aqueous phase was separated and extracted with CH$_2$Cl$_2$ (15 mL×2). The combined organic phases were washed with saturated aqueous NaHCO$_3$ (50 mL), dried over Na$_2$SO$_4$, filtered, and concentrated. The residue was purified by flash chromatography (hexanes to 40% EtOAc in hexanes, gradient) to afford 709 mg compound 63 (72% yield). LCMS (ESI): m/z calculated for C$_{32}$H$_{32}$F$_3$N$_3$O$_7$: 627.2, found 650.1 (M+Na).

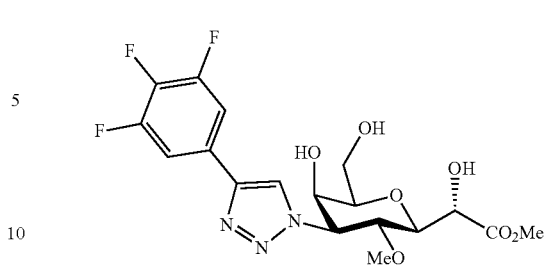

64

Compound 64: To a solution of compound 63 (1.1 g, 1.75 mmol) in anhydrous MeOH) (20 mL) was added Pd(OH)$_2$ on carbon (0.22 g, 20% by wt). The mixture was cooled on an ice bath and stirred for 30 minutes. Triethylsilane (11 mL, 70 mmol) was added dropwise. The solution was allowed to slowly warm to ambient temperature and stirred for 16 hours. The reaction mixture was filtered through a bed of Celite and concentrated. The residue was purified by flash chromatography (hexanes to 100% EtOAc, gradient) to afford compound 64 (673 mg, 86%).

LCMS (ESI): m/z calculated for C$_{18}$H$_{20}$F$_3$N$_3$O$_7$: 447.1, found 470.1 (M+Na).

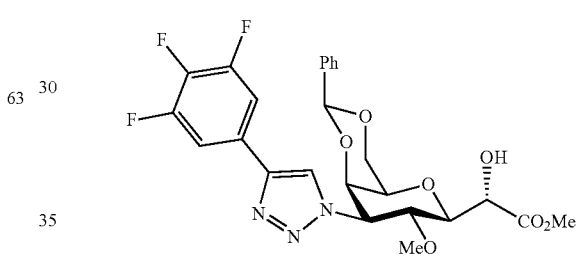

65

Compound 65: Compound 64 (600 mg, 1.34 mmol) and CSA (62 mg, 0.27 mmol) were suspended in anhydrous MeCN (20 mL) under an argon atmosphere. Benzaldehyde dimethyl acetal (0.22 mL, 1.48 mmol) was added dropwise. The reaction mixture was allowed to stir for 16 hours at ambient temperature, during which time it became a homogenous solution. The reaction mixture was then neutralized with a few drops of Et$_3$N, and concentrated. The residue was purified via flash chromatography (hexanes to 50% EtOAc, gradient) to afford compound 65 (560 mg, 780%).

LCMS (ESI): m/z calculated for C$_{25}$H$_{24}$F$_3$N$_3$O$_7$: 535.2, found 558.1 (M+Na).

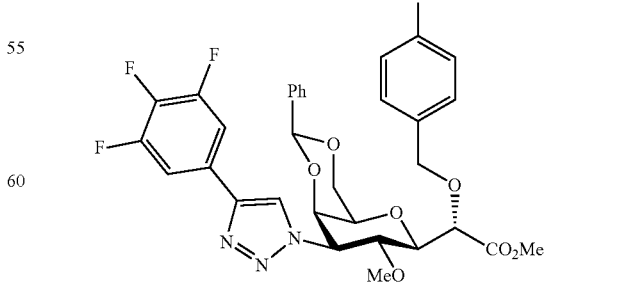

66

Compound 66: Compound 65 (170 mg, 0.32 mmol) was azeotroped from toluene 2 times under reduced pressure, dried under high vacuum for 2 hours, then dissolved in anhydrous THF (4 mL) and cooled on an ice bath. Benzyl bromide (78 mg, 0.38 mmol) dissolved in 0.5 mL of anhydrous THF was added and the reaction and was stirred under an atmosphere of argon for 5 minutes at 0° C. Sodium hydride (15 mg, 0.38 mmol, 60% oil dispersion) was added and the reaction was allowed to gradually warm to ambient temperature while stirring for 16 hours. The reaction mixture was diluted with EtOAc (20 mL), transferred to a separatory funnel, and washed with H$_2$O (10 mL). The aqueous phase was extracted with EtOAc (10 mL×3). The combined organic phases were washed with brine (10 mL×3), dried over Na$_2$SO$_4$, filtered, and concentrated. The residue was purified via flash chromatography (hexanes to 50% EtOAc, gradient) to afford compound 66 (182 mg 86%).

LCMS (ESI): m/z calculated for C$_{32}$H$_{29}$ClF$_3$N$_3$O$_7$: 659.2, found 682.1 (M+Na).

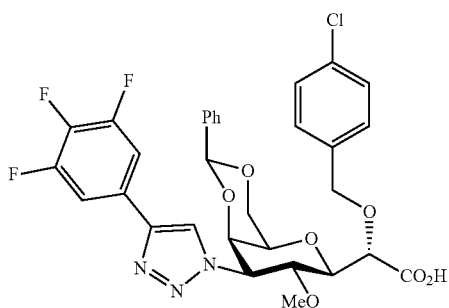

Compound 67: To a solution of compound 66 (117 mg, 0.17 mmol) in methanol (1.8 mL) was added sodium hydroxide (0.2 mL of a 1.0 M aqueous solution). The reaction mixture was stirred at room temperature overnight. The reaction mixture was neutralized by the addition of acidic ion exchange resin, filtered, and concentrated to give 99 mg crude compound 67 which was used without further purification.

LCMS (ESI): m/z calculated for C$_{31}$H$_{27}$ClF$_3$N$_3$O$_7$: 645.2, found 644.2 (M−H).

68

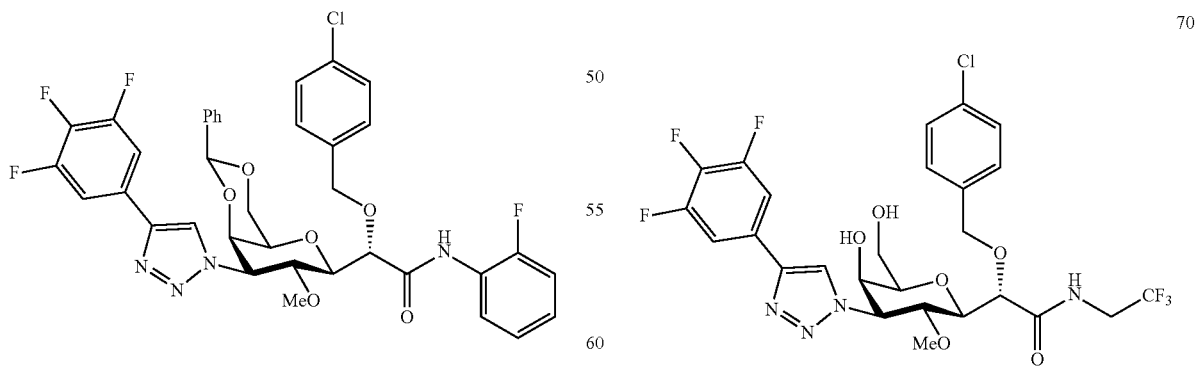

Compound 68: Compound 67 (50 mg, 0.08 mmol) was dissolved in DMF at room temperature. Diisopropylethylamine (24 mg, 0.24 mmol) was added followed by HATU (34 mg, 0.09 mmol) and then 2-fluoroaniline (13 mg, 0.12 mmol). The reaction mixture was stirred overnight at room temperature. The reaction mixture was diluted with dichloromethane, transferred to a separatory funnel, and washed with water. The organic phase was concentrated and purified by column chromatography to afford 28 mg compound 68 as a white solid (47% yield).

LCMS (ESI): m/z calculated for C$_{37}$H$_{31}$ClF$_4$N$_4$O$_6$: 738.2, found 739.2 (M+H).

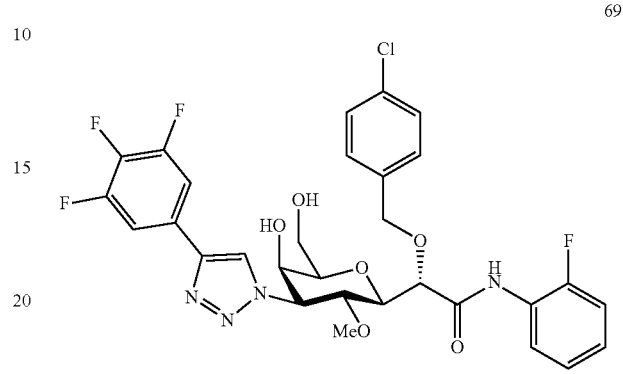

Compound 69: Compound 68 (28 mg, 0.04 mmol) was dissolved in methanol. Camphorsulfonic acid (2 mg, 0.009 mmol) was added and the reaction mixture was heated for 2 hours at 70° C. The reaction mixture was cooled to room temperature, neutralized by the addition of basic ion exchange resin, filtered, and concentrated. The residue was purified by flash chromatography to afford 18 mg of compound 69 as a white solid (75% yield)

$^1$H NMR (400 MHz, Methanol-d4) δ 8.64 (d, J=1.3 Hz, 1H), 7.60 (t, J=7.6 Hz, 2H), 7.43 (d, J=8.0 Hz, 2H), 7.32 (dd, J=8.2, 1.4 Hz, 2H), 7.19-7.01 (m, 3H), 4.90 (dt, J=10.7, 2.0 Hz, 1H), 4.73 (d, J=11.4 Hz, 1H), 4.57 (d, J=11.4 Hz, 1H), 4.31 (s, 11H), 4.24 (t, J=9.9 Hz, 1H), 4.08-3.96 (m, 1H), 3.77 (d, J=9.4 Hz, 1H), 3.61 (s, 3H), 2.94 (d, J=1.4 Hz, 3H). LCMS (ESI): mm/z calculated for C$_{30}$H$_{27}$ClF$_4$N$_4$O$_6$: 650.1, found 651.1 (M+H).

Example 28

Synthesis of Compound 70

70

Figure 6:
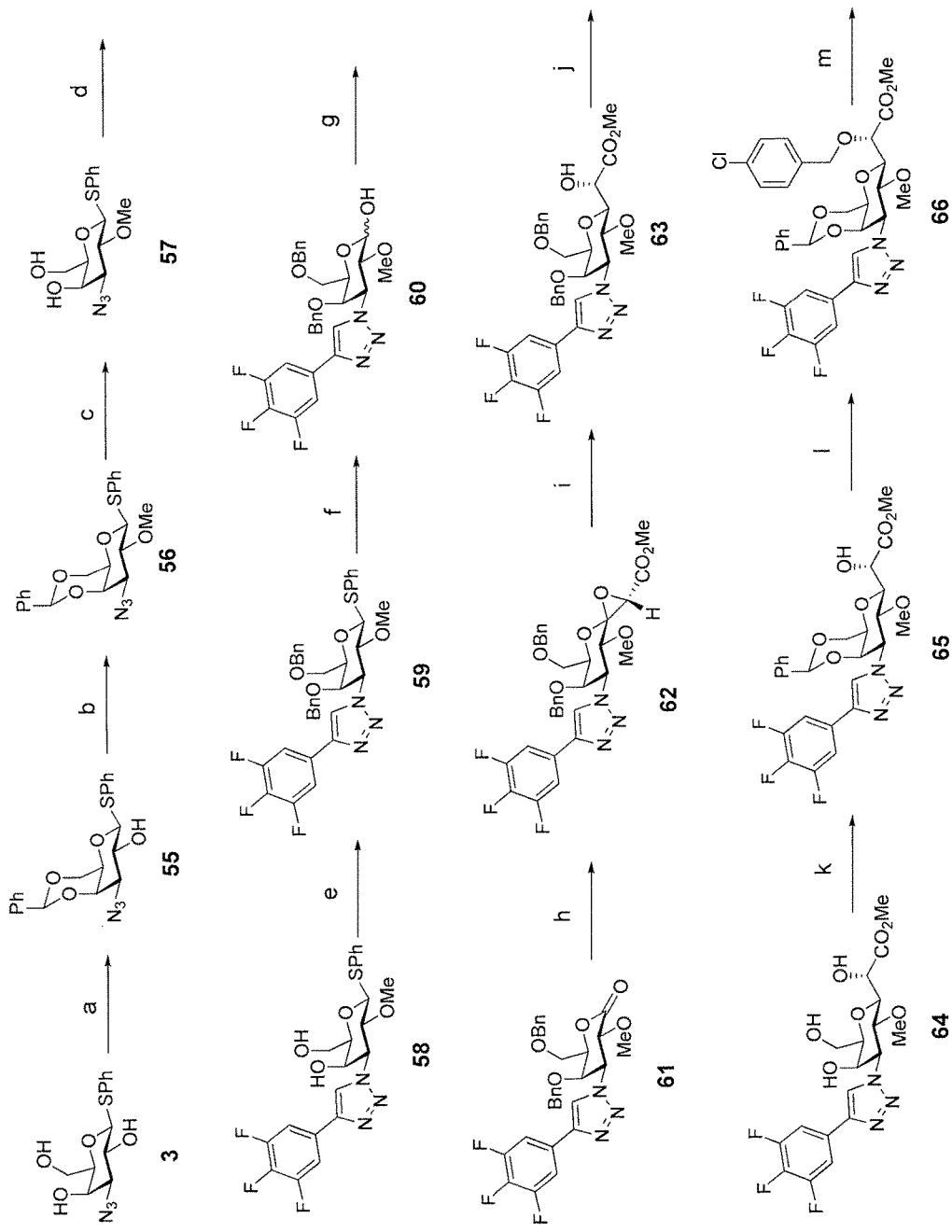
FIG. 6 is a diagram illustrating the synthesis of Compound 69.
Figure 6:
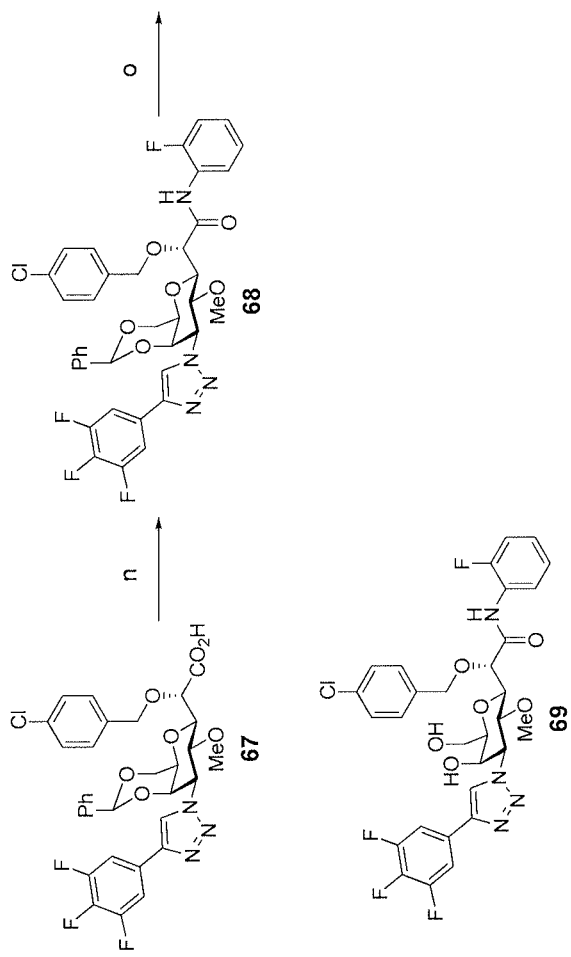

Compound 70: Compound 70 was prepared according to FIG. 6.

1H NMR (400 MHz, Methanol-d4) δ 8.60 (d, J=15 Hz, 1H), 7.65-7.53 (m, 2H), 7.44-7.35 (m, 2H), 7.34-7.24 (m, 2H), 4.85 (d, J=10.6 Hz, 1H), 4.63 (d, J=11.2 Hz, 1H), 4.41

(d, J=11.3 Hz, 1H), 4.26-4.14 (m, 2H), 4.02 (d, J=16.5 Hz, 2H), 3.77 (dq, J=17.6, 9.1 Hz, 1H), 3.59 (td, J=16.4, 14.7, 7.6 Hz, 4H), 2.87 (d, J=1.6 Hz, 3H). LCMS (ESI): m/z calculated for $C_{26}H_{25}ClFN_4O_6$: 638.1, found 637.1 (M–H).

Example 29

Prophetic Synthesis of Compound 71

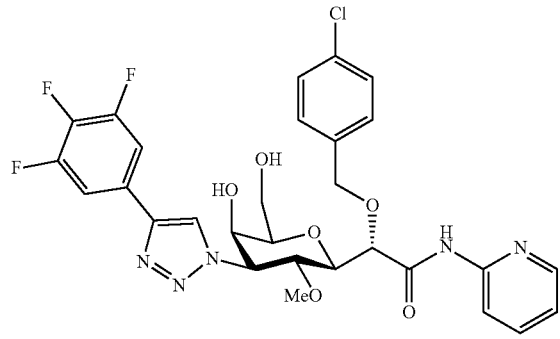

Compound 71: Compound 71 can be prepared according to FIG. 6 by replacing 2-fluoroaniline with 2-aminopyridine.

Example 30

Prophetic Synthesis of Compound 72

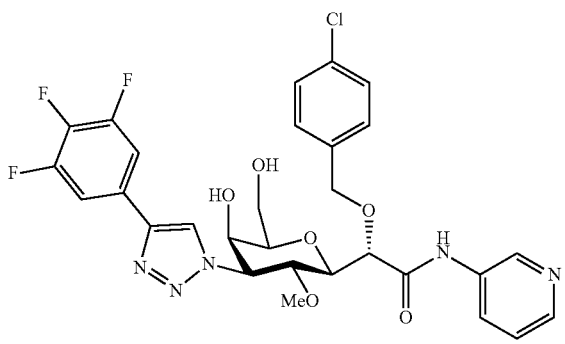

Compound 72: Compound 72 can be prepared according to FIG. 6 by replacing 2-fluoroaniline with 3-aminopyridine.

Example 31

Prophetic Synthesis of Compound 73

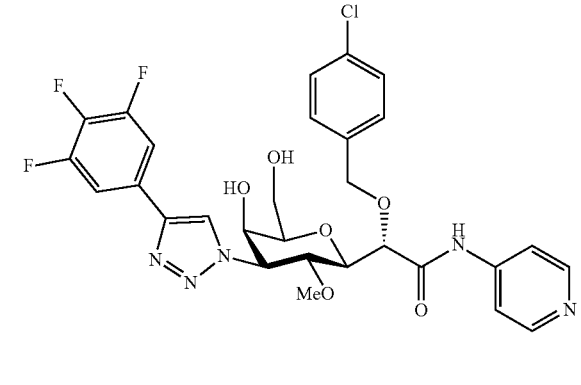

Compound 73: Compound 73 can be prepared according to FIG. 6 by replacing 2-fluoroaniline with 4-aminopyridine.

Example 32

Prophetic Synthesis of Compound 74

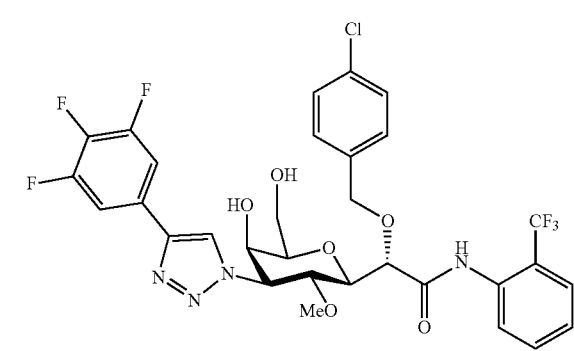

Compound 74: Compound 74 can be prepared according to FIG. 6 by replacing 2-fluoroaniline with 2-trifluoromethylaniline.

Example 33

Prophetic Synthesis of Compound 75

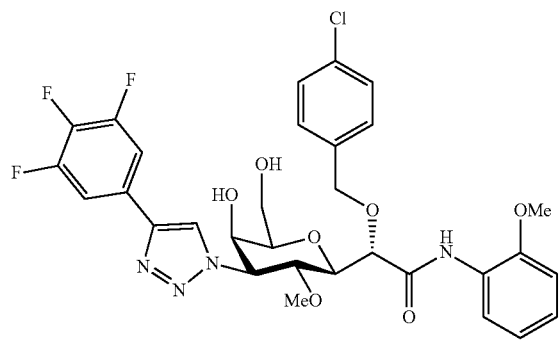

75

Compound 75: Compound 75 can be prepared according to FIG. 6 by replacing 2-fluoroaniline with 2-methoxyaniline.

Example 34

Prophetic Synthesis of Compound 76

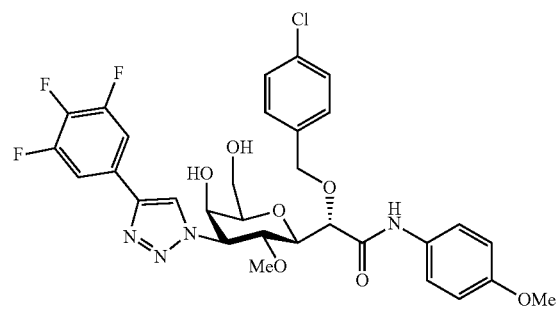

76

Compound 76: Compound 76 can be prepared according to FIG. 6 by replacing 2-fluoroaniline with 4-methoxyaniline.

Example 35

Prophetic Synthesis of Compound 77

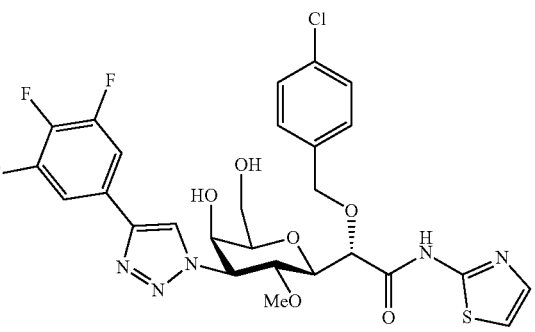

77

Compound 77: Compound 77 can be prepared according to FIG. 6 by replacing 2-fluoroaniline with 2-aminothiazole.

Example 36

Prophetic Synthesis of Compound 78

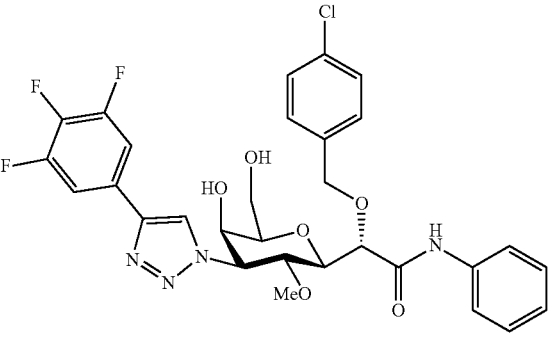

78

Compound 78: Compound 78 can be prepared according to FIG. 6 by replacing 2-fluoroaniline with aniline.

Example 37

Prophetic Synthesis of Compound 79

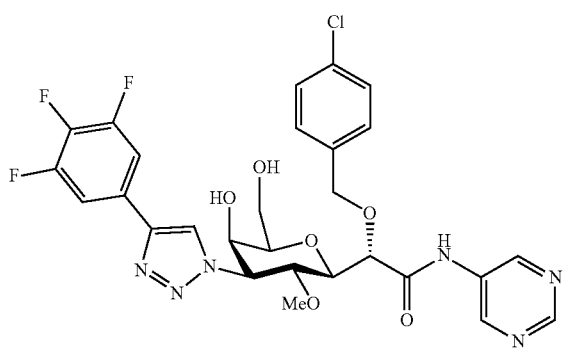

Compound 79: Compound 79 can be prepared according to FIG. 6 by replacing 2-fluoroaniline with 5-aminopyrimidine.

Example 38

Prophetic Synthesis of Compound 80

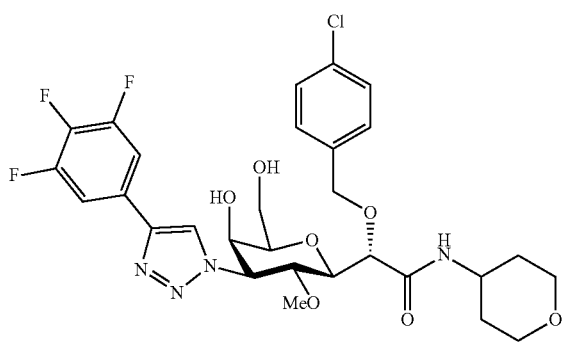

Compound 80: Compound 80 can be prepared according to FIG. 6 by replacing 2-fluoroaniline with 4-aminopyran.

Example 39

Galectin-3 Activity—ELISA Assay

Galectin-3 antagonists were evaluated for their ability to inhibit binding of galectin-3 to a Galβ1-3GlcNAc carbohydrate structure. The detailed protocol was as follows. A 1 ug/mL suspension of a Galβ1-3GlcNAcβ1-3Galβ1-4GcNAcβ-PAA-biotin polymer (Glycotech, catalog number 01-096) was prepared. A 100 uL aliquot of the polymer was added to the wells of a 96-well streptavidin-coated plate (R&D Systems, catalog number CP004). A 100 uL aliquot of IX Tris Buffered Saline (TBS, Sigma, catalog number T5912-10×) was added to control wells. The polymer was allowed to bind to the streptavidin-coated wells for 1.5 hours at room temperature. The contents of the wells were discarded and 200 uL of 1×TBS containing 1% bovine serum albumin (BSA) was added to each well as a blocking reagent and the plate was kept at room temperature for 30 minutes. The wells were washed three times with IX TBS containing 0.1% BSA. A serial dilution of test compounds was prepared in a separate V-bottom plate (Corning, catalog number 3897). A 75 uL aliquot of the highest concentration of the compound to be tested was added to the first well in a column of the V-bottom plate then 15 ul were serially transferred into 60 uL IX TBS through the remaining wells in the column to generate a 1 to 5 serial dilution. A 60 uL aliquot of 2 ug/mL galectin-3 (IBL, catalog number IBATGP0414) was added to each well in the V-bottom plate. A 100 uL aliquot of the galectin-3/test compound mixture was transferred from the V-bottom plate into the assay plate containing the Galβ1-3GlcNAc polymer. Four sets of control wells in the assay plate were prepared in duplicate containing 1) both Galβ1-3GlcNAc polymer and galectin-3, 2) neither the polymer nor galectin-3, 3) galectin-3 only, no polymer, or 4) polymer only, no galectin-3. The plate was gently rocked for 1.5 hours at room temperature. The wells were washed four times with TBS/0.1% BSA. A 100 uL aliquot of anti-galectin-3 antibody conjugated to horse radish peroxidase (R&D Systems, from DGAL30 kit) was added to each well and the plate was kept at room temperature for 1 hour. The wells were washed four times with TBS/0.1% BSA. A 100 uL aliquot of TMB substrate solution was added to each well. The TMB substrate solution was prepared by making a 1:1 mixture of TMB Peroxidase Substrate (KPL, catalog number 5120-0048) and Peroxidase Substrate Solution B (KPL, catalog number 5120-0037). The plate was kept at room temperature for 10 to 20 minutes. The color development was stopped by adding 100 uL 10% phosphoric acid (RICCA Chemical Co., catalog number 5850-16). The absorbance at 450 nm ($A_{450}$) was measured using a FlexStation 3 plate reader (Molecular Devices). Plots of $A_{450}$ versus test compound concentration and $IC_{50}$ determinations were made using GraphPad Prism 6.

| Galectin-3 Antagonist Activity | |
|---|---|
| Compound Number | IC50 (μM) |
| 13 | 3.48 |
| 16 | 0.53 |
| 17 | 2.56 |
| 18 | 0.67 |
| 19 | 0.32 |
| 20 | 1.52 |
| 21 | 1.94 |
| 24 | 1.72 |
| 25 | 1.08 |
| 26 | 0.35 |
| 27 | 2.09 |
| 28 | 0.69 |
| 31 | 0.18 |
| 32 | 2.81 |
| 33 | 1.64 |
| 29 | 4.60 |
| 30 | 4.98 |
| 34 | 0.85 |
| 35 | >100 |
| 36 | 3.86 |
| 40 | 2.61 |
| 41 | 9.58 |
| 42 | 2.06 |
| 69 | 0.23 |
| 70 | 0.72 |

What is claimed is:

1. At least one compound chosen from compounds of Formula (I):

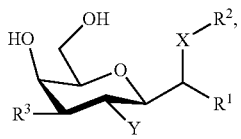

and pharmaceutically acceptable salts thereof, wherein $R^1$ is chosen from —CN, —CH$_2$CN, and —C(=O)Q groups, wherein Q is chosen from —OZ$^1$, —NHOH, —NHOCH$_3$, —NHCN, and —NZ$^1$Z$^2$ groups, wherein Z$^1$ and Z$^2$, which may be identical or different, are independently chosen from H, C$_{1-8}$ alkyl, C$_{2-12}$ heterocyclyl, C$_{6-18}$ aryl, and C$_{1-13}$ heteroaryl groups, wherein the C$_{2-12}$ heterocyclyl, C$_{6-18}$ aryl and C$_{1-13}$ heteroaryl groups are optionally substituted with one or more groups independently chosen from halo, C$_{1-8}$ alkyl, C$_{1-8}$ hydroxyalkyl, C$_{1-8}$ haloalkyl, C$_{6-18}$ aryl, —OT$^1$, —C(=O)OT$^1$, —C(=O)NT$^1$T$^2$, —CN, —ST$^1$, S(O)T$^1$, and —SO$_2$T$^1$ groups, wherein T$^1$ and T$^2$, which may be identical or different, are independently chosen from H, C$_{1-8}$ alkyl, and C$_{1-8}$ haloalkyl groups, or T$^1$ and T$^2$ join together along with the nitrogen atom to which they are attached to form a ring, or Z$^1$ and Z$^2$ join together along with the nitrogen atom to which they are attached to form a ring;

$R^2$ is chosen from H, C$_{1-8}$ alkyl, C$_{2-8}$ alkenyl, C$_{2-8}$ alkynyl, C$_{1-8}$ haloalkyl, C$_{2-8}$ haloalkenyl, C$_{2-8}$ haloalkynyl, C$_{4-16}$ cycloalkylalkyl, C$_{6-18}$ aryl, C$_{1-13}$ heteroaryl, C$_{7-19}$ arylalkyl, and C$_{2-14}$ heteroarylalkyl groups, wherein the C$_{1-8}$ alkyl, C$_{2-8}$ alkenyl, C$_{2-8}$ alkynyl, C$_{1-8}$ haloalkyl, C$_{2-8}$ haloalkenyl, C$_{2-8}$ haloalkynyl, C$_{4-16}$ cycloalkylalkyl, C$_{6-18}$ aryl, C$_{1-13}$ heteroaryl, C$_{7-19}$ arylalkyl, and C$_{2-14}$ heteroarylalkyl groups are optionally substituted with one or more groups independently chosen from halo, C$_{1-8}$ alkyl, C$_{1-8}$ hydroxyalkyl, C$_{1-8}$ haloalkyl, C$_{6-18}$ aryl, —OZ$^3$, —C(=O)OZ$^3$, —C(=O)NZ$^3$Z$^4$, and —SO$_2$Z$^3$ groups, wherein Z$^3$ and Z$^4$, which may be identical or different, are independently chosen from H, C$_{1-8}$ alkyl, and C$_{1-8}$ haloalkyl groups, or Z$^3$ and Z$^4$ join together along with the nitrogen atom to which they are attached to form a ring;

$R^3$ is chosen from C$_{6-18}$ aryl and C$_{1-13}$ heteroaryl groups, wherein the C$_{6-18}$ aryl and C$_{1-13}$ heteroaryl groups are optionally substituted with one or more groups independently chosen from R$^4$, C$_{1-8}$ alkyl, C$_{1-8}$ haloalkyl, —C(=O)OZ$^5$, and —C(=O)NZ$^5$Z$^6$ groups, wherein R$^4$ is independently chosen from C$_{6-18}$ aryl groups optionally substituted with one or more groups independently chosen from halo, C$_{1-8}$ alkyl, —OZ$^7$, —C(=O)OZ$^7$, and —C(=O)NZ$^7$Z$^8$ groups, wherein Z$^5$, Z$^6$, Z$^7$ and Z$^8$, which may be identical or different, are independently chosen from H and C$_{1-8}$ alkyl groups, or Z$^5$ and Z$^6$ join together along with the nitrogen atom to which they are attached to form a ring and/or Z$^7$ and Z$^8$ join together along with the nitrogen atom to which they are attached to form a ring;

X is chosen from —O—, —S—, —CH$_2$—, and —N(R$^5$)—, wherein R$^5$ is chosen from H, C$_{1-8}$ alkyl, C$_{2-8}$ alkenyl, C$_{2-8}$ alkynyl, C$_{1-8}$ haloalkyl, C$_{2-8}$ haloalkenyl, and C$_{2-8}$ haloalkynyl groups;

Y is chosen from H, halo, and —OZ$^9$ groups, wherein Z$^9$ is chosen from H and C$_{1-8}$ alkyl groups; and wherein each of Z$^1$, Z$^2$, Z$^3$, Z$^4$, Z$^5$, Z$^6$, Z$^7$, Z$^8$, and Z$^9$ is optionally substituted with one or more groups independently chosen from halo and —OR$^6$ groups, wherein R$^6$ is independently chosen from H and C$_{1-8}$ alkyl groups.

2. The at least one compound according to claim 1 chosen from compounds of Formula (IA):

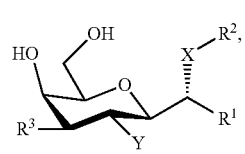

and pharmaceutically acceptable salts thereof.

3. The at least one compound according to claim 2 chosen from compounds of Formula (IA).

4. The at least one compound according to claim 2, wherein R$^1$ is chosen from —CN, —CH$_2$CN, and —C(=O)Q groups, wherein Q is chosen from —OZ$^1$, —NHOH, —NHOCH$_3$, —NHCN, and —NZ$^1$Z$^2$ groups, wherein Z$^1$ and Z$^2$, which may be identical or different, are independently chosen from H and C$_{1-8}$ alkyl groups, or Z$^1$ and Z$^2$ join together along with the nitrogen atom to which they are attached to form a ring.

5. The at least one compound according to claim 2, wherein R$^1$ is chosen from —C(=O)Q groups, wherein Q is chosen from —OZ$^1$, —NHOH, —NHOCH$_3$, —NHCN, and —NZ$^1$Z$^2$ groups, wherein Z$^1$ and Z$^2$, which may be identical or different, are independently chosen from H and C$_{1-8}$ alkyl groups, or Z$^1$ and Z$^2$ join together along with the nitrogen atom to which they are attached to form a ring.

6. The at least one compound according to claim 4, wherein Q is chosen from —OZ$^1$ and —NZ$^1$Z$^2$ groups.

7. The at least one compound according to claim 4, wherein Q is chosen from —OZ$^1$ groups, wherein Z$^1$ is chosen from H and C$_{1-6}$ alkyl groups.

8. The at least one compound according to claim 2, wherein R$^1$ is chosen from

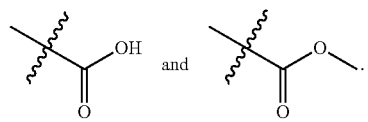

9. The at least one compound according to claim 4, wherein Q is chosen from —NZ$^1$Z$^2$ groups, wherein Z$^1$ and Z$^2$, which may be identical or different, are independently chosen from H and C$_{1-6}$ alkyl groups.

10. The at least one compound according to claim 2, wherein $R^1$ is chosen from

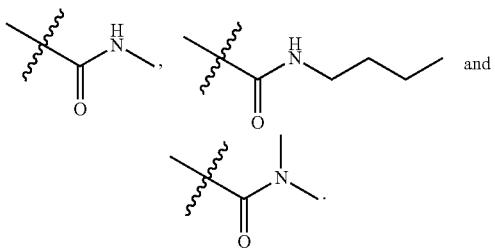

11. The at least one compound according to claim 2, wherein $R^1$ is chosen from —C(=O)Q groups, wherein Q is chosen from
- —$NZ^1Z^2$ groups, wherein $Z^1$ and $Z^2$, which may be identical or different, are independently chosen from H, $C_{1-8}$ alkyl, $C_{2-12}$ heterocyclyl, $C_{6-18}$ aryl, and $C_{1-13}$ heteroaryl groups.

12. The at least one compound according to claim 2, wherein $R^1$ is chosen from —C(=O)Q groups, wherein Q is chosen from
- —$NZ^1Z^2$ groups, wherein $Z^1$ is H and $Z^2$ is chosen from $C_{2-12}$ heterocyclyl, $C_{6-18}$ aryl, and $C_{1-13}$ heteroaryl groups.

13. The at least one compound according to claim 2, wherein $R^1$ is chosen from

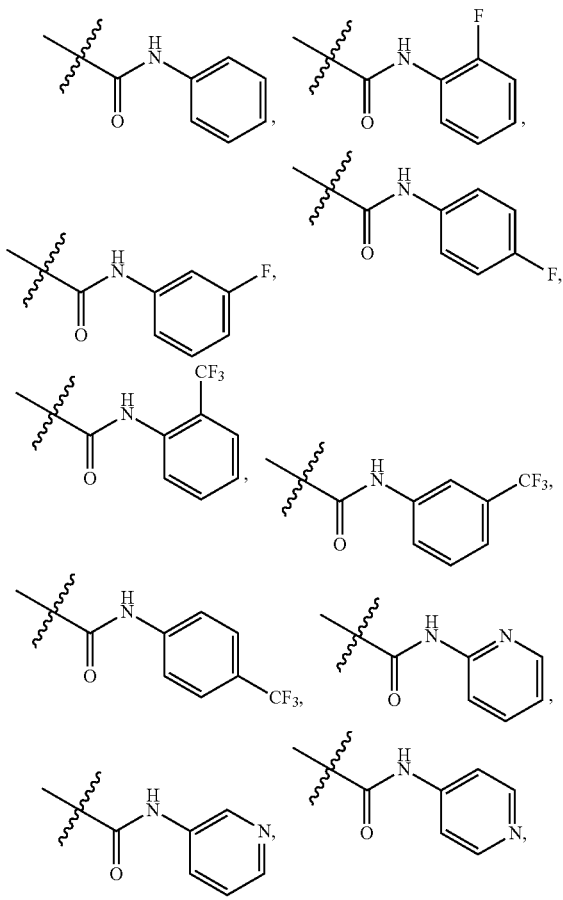

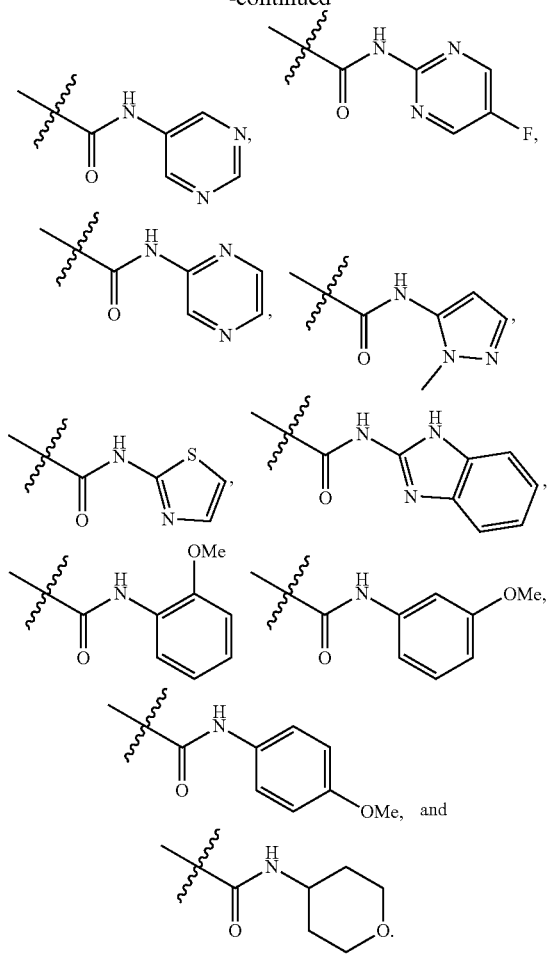

14. The at least one compound according to claim 2, wherein $R^2$ is chosen from H, $C_{1-8}$ alkyl, $C_{4-16}$ cycloalkylalkyl, $C_{7-19}$ arylalkyl, and $C_{2-14}$ heteroarylalkyl groups.

15. The at least one compound according to claim 14, wherein $R^2$ is H.

16. The at least one compound according to claim 14, wherein $R^2$ is chosen from $C_{1-8}$ alkyl and $C_{4-16}$ cycloalkylalkyl groups.

17. The at least one compound according to claim 14, wherein $R^2$ is chosen from Me and cyclopropylmethyl.

18. The at least one compound according to claim 14, wherein $R^2$ is chosen from $C_{7-19}$ arylalkyl and $C_{2-14}$ heteroarylalkyl groups.

19. The at least one compound according to claim 14, wherein $R^2$ is chosen from

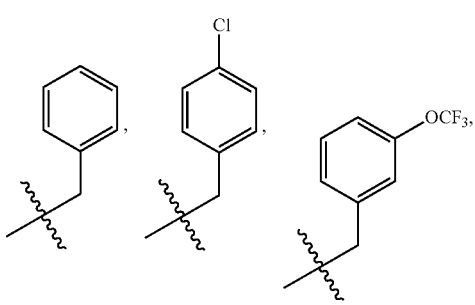

-continued

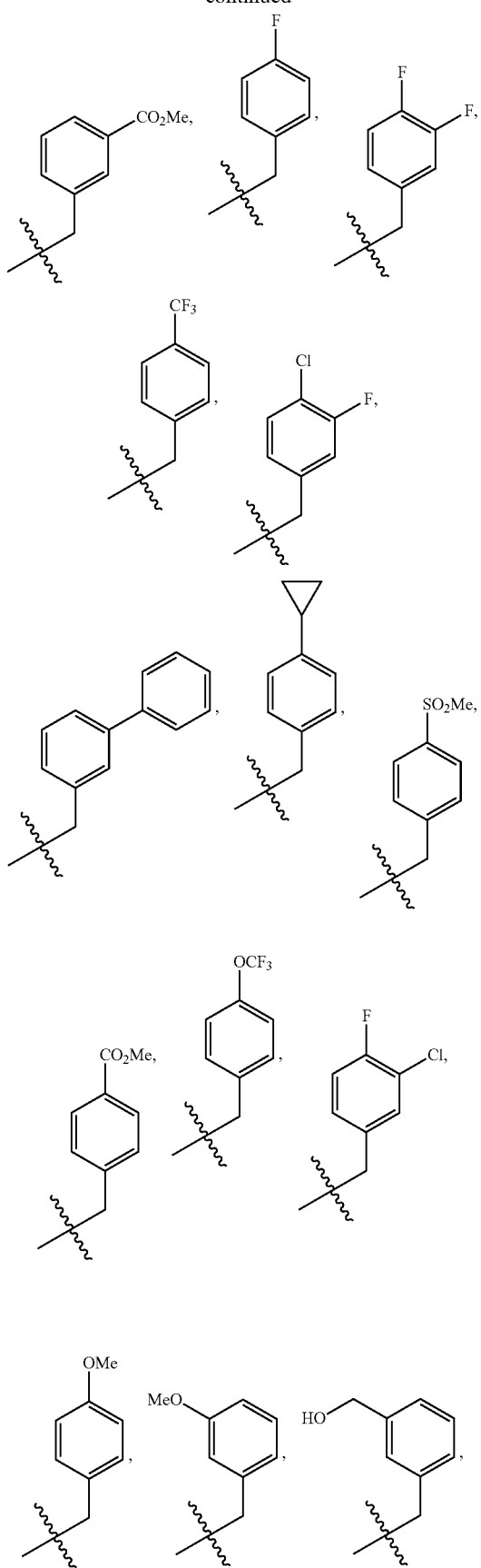

-continued

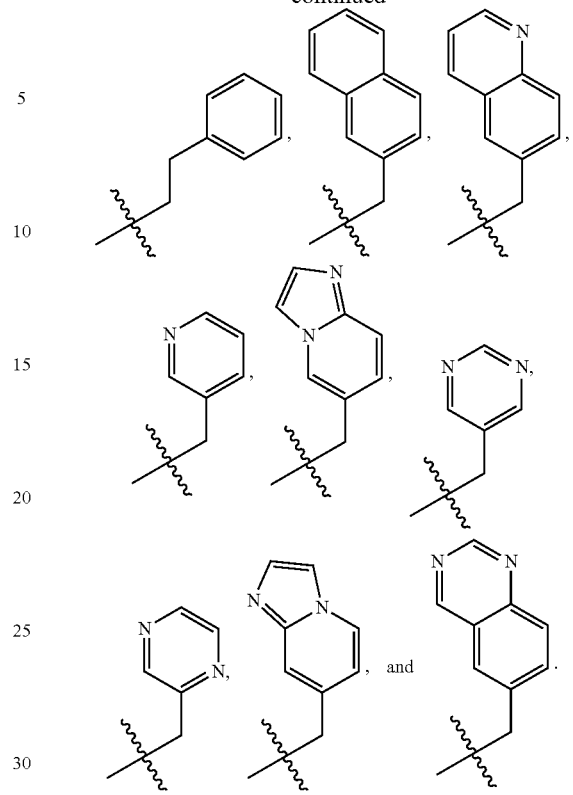

20. The at least one compound according to claim 2, wherein $R^3$ is chosen from $C_{1-13}$ heteroaryl groups.

21. The at least one compound according to claim 20, wherein $R^3$ is chosen from $C_{1-13}$ heteroaryl groups substituted with one or more groups independently chosen from $R^4$.

22. The at least one compound according to claim 20, wherein $R^3$ is chosen from

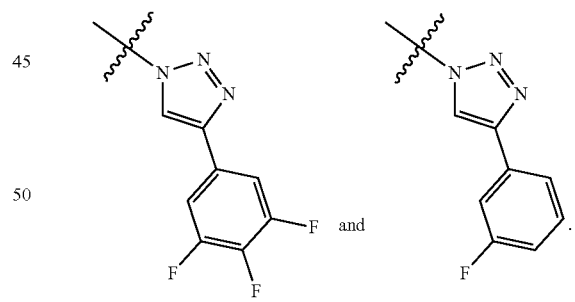

23. The at least one compound according to claim 2, wherein X is —O—.

24. The at least one compound according to claim 2, wherein X is —S—.

25. The at least one compound according to claim 2, wherein X is —CH$_2$—.

26. The at least one compound according to claim 2, wherein Y is H.

27. The at least one compound according to claim 2, wherein Y is chosen from halo groups.

28. The at least one compound according to claim 27, wherein Y is fluoro.

29. The at least one compound according to claim 2, wherein Y is chosen from —OZ$^9$ groups.

30. The at least one compound according to claim 29, wherein Y is —OH.

31. The at least one compound according to claim 29, wherein Y is —OMe.

32. A composition comprising the at least one compound of claim 2 and at least one additional pharmaceutically acceptable ingredient.

33. A method for treatment of at least one inflammatory disease, disorder, and/or condition, the method comprising administering to a subject in need thereof an effective amount of at least one compound of claim 2.

34. A method for treatment of cancer, the method comprising administering to a subject in need thereof an effective amount of at least one compound of claim 2.

35. The method according to claim 34, wherein the cancer is chosen from solid tumor cancers.

36. The method according to claim 34, wherein the cancer is chosen from bone cancers, colorectal cancers, and pancreatic cancers.

37. The method according to claim 34, wherein the cancer is chosen from liquid tumor cancers.

38. The method according to claim 34, wherein the cancer is chosen from acute myelogenous leukemia, acute lymphoblastic leukemia, chronic myelogenous leukemia, and multiple myeloma.

39. A method for treatment of cancer, the method comprising administering to a subject in need thereof (a) an effective amount of at least one compound of claim 2 and (b) at least one therapy chosen from (i) chemotherapy and (ii) radiotherapy.

40. A method for treatment of metastasis of cancer cells, the method comprising administering to a subject in need thereof an effective amount of at least one compound of claim 2.

41. A method for inhibiting infiltration of cancer cells into the liver, lymph nodes, lung, bone, and/or bone marrow, the method comprising administering to a subject in need thereof an effective amount of at least one compound of claim 2.

42. A method for enhancing hematopoietic stem cell survival, the method comprising administering to a subject in need thereof an effective amount of at least one compound of claim 2.

43. The method according to claim 42, wherein the subject has cancer and has received or will receive chemotherapy and/or radiotherapy.

44. A method for mobilizing cells from the bone marrow, the method comprising administering to a subject in need thereof an effective amount of at least one compound of claim 2.

45. The method according to claim 44, wherein the cells are chosen from hematopoietic cells and tumor cells.

46. A method for treatment of thrombosis, the method comprising administering to a subject in need thereof an effective amount of at least one compound of claim 2.

47. A method for treatment of at least one cardiovascular disease or complications associated therewith, the method comprising administering to a subject in need thereof an effective amount of at least one compound of claim 2.

48. The method according to claim 47, wherein the at least one cardiovascular disease is chosen from atherosclerosis and myocardial infarction.

49. A method of inhibiting rejection of a transplanted tissue in a subject, wherein said subject is a recipient of the transplanted tissue, the method comprising administering to a subject in need thereof an effective amount of at least one compound of claim 2.

50. A method for treatment of graft versus host disease or complications associated therewith, the method comprising administering to a subject in need thereof an effective amount of at least one compound of claim 2.

51. A method for treatment of pathological angiogenesis, the method comprising administering to a subject in need thereof an effective amount of at least one compound of claim 2.

52. The method according to claim 51, wherein the pathological angiogenesis occurs in the eye.

53. The method according to claim 51, wherein the pathological angiogenesis occurs in a subject with cancer.

54. A method for treatment of an epileptic syndrome, the method comprising administering to a subject in need thereof an effective amount of at least one compound of claim 2.

55. A method for treatment of neurodegeneration, the method comprising administering to a subject in need thereof an effective amount of at least one compound of claim 2.

56. The method according to claim 55, wherein the neurodegenerative disease is an α-synucleinopathy.

57. A method for treatment of fibrosis, the method comprising administering to a subject in need thereof an effective amount of at least one compound of claim 2.

58. The method according to claim 57, wherein the fibrosis is pulmonary fibrosis.

59. The method according to claim 57, wherein the fibrosis is cardiac fibrosis.

60. A method for treatment of liver disorders or complications associated therewith, the method comprising administering to a subject in need thereof an effective amount of at least one compound of claim 2.

61. The method according to claim 60, wherein the liver disorder is nonalcoholic steatohepatitis.

* * * * *